(12) United States Patent
Westin et al.

(10) Patent No.: US 10,338,083 B2
(45) Date of Patent: *Jul. 2, 2019

(54) PATHWAY SPECIFIC MARKERS FOR DIAGNOSING IRRITABLE BOWEL SYNDROME

(71) Applicant: Nestec S.A., Vevey (CH)

(72) Inventors: Stefan Westin, Carlsbad, CA (US); Fabiyola Selvaraj, San Diego, CA (US); Fred Princen, La Jolla, CA (US); Sharat Singh, Rancho Santa Fe, CA (US)

(73) Assignee: NESTEC S.A., Vevey (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/024,183

(22) Filed: Jun. 29, 2018

(65) Prior Publication Data

US 2018/0321259 A1 Nov. 8, 2018

Related U.S. Application Data

(63) Continuation of application No. 15/646,838, filed on Jul. 11, 2017, now Pat. No. 10,036,759, which is a continuation of application No. 14/938,729, filed on Nov. 11, 2015, now Pat. No. 9,739,786, which is a continuation of application No. PCT/IB2014/061636, filed on May 22, 2014.

(60) Provisional application No. 61/827,506, filed on May 24, 2013.

(51) Int. Cl.
| | |
|---|---|
| *G01N 33/68* | (2006.01) |
| *G01N 33/94* | (2006.01) |
| *C07K 16/12* | (2006.01) |
| *C07K 16/26* | (2006.01) |
| *C07D 495/04* | (2006.01) |
| *C07D 498/04* | (2006.01) |
| *C07D 519/00* | (2006.01) |
| *C07K 16/44* | (2006.01) |

(52) U.S. Cl.
CPC ....... *G01N 33/6893* (2013.01); *C07D 495/04* (2013.01); *C07D 498/04* (2013.01); *C07D 519/00* (2013.01); *C07K 16/12* (2013.01); *C07K 16/26* (2013.01); *C07K 16/44* (2013.01); *G01N 33/6812* (2013.01); *G01N 33/942* (2013.01); *C07K 2317/33* (2013.01); *G01N 2800/065* (2013.01); *G01N 2800/52* (2013.01)

(58) Field of Classification Search
None
See application file for complete search history.

(56) References Cited

U.S. PATENT DOCUMENTS

| 8,445,215 B1 * | 5/2013 | Wang | G01N 33/564 435/7.1 |
|---|---|---|---|
| 2006/0154276 A1 | 7/2006 | Lois et al. | |
| 2008/0085524 A1 | 4/2008 | Lois | |
| 2012/0315630 A1 | 12/2012 | Gong et al. | |
| 2013/0225439 A1 | 8/2013 | Princen et al. | |
| 2016/0130279 A1 | 5/2016 | Selvaraj et al. | |

FOREIGN PATENT DOCUMENTS

| WO | 2011/066458 A2 | 6/2011 |
|---|---|---|
| WO | 2014/053996 A2 | 4/2014 |

OTHER PUBLICATIONS

Chen et al. (Molecular & Cellular Proteomics 8.8 2009 p. 1765-1775 (Year: 2009).*
Camilleri, M. et al., "Measurement of serum 7α-hydroxy-4-cholesten-3-one (or 7αC4), a surrogate test for bile acid malabsorption in health, ileal disease and irritable bowel syndrome using liquid chromatography-tandem mass spectrometry," Neurogastroenterol. Motil., 21(7):734-e43, 2009.
Chauveau, J. et al., "Rapid and specific enzyme immunoassay of serotonin," Clinical Chemistry, 37(7):1178-1184, 1991.
Chien-Sheng, C. et al., "Identification of novel serological biomarkers for inflammatory bowel disease using *Escherichia coli* proteome chip," Molecular & Cellular Proteomics, 8(8):1765-76, 2009.
Huisman, H. et al,. "Studies on the immune response and preparation of antibodies against a large panel of conjugated neurotransmitters and biogenic amines: specific polyclonal antibody response and tolerance," Journal of Neurochemistry, 112(3):829-841, 2010.
Makosza, M. et al., "Synthesis of 1,3,4,5-tetrahydropyrrolo[4,3,2-de]quinolines via the vicarious nucleophilic substitution of hydrogen," Tetrahedron, 51(26):7263-7276, 1995.
Nichkova, M. et al., "Evaluation of a novel ELISA for serotonin: urinary serotonin as a potential biomarker for depression," Analytical and Bioanalytical Chemistry, 402(4):1593-1600, 2011.
Plevy, S. et al., "Combined serologic, genetic, and inflammatory markers can accurately differentiate non-IBD, Crohn's disease, and ulcerative colitis patients," Gastroenterology, 142(5, S1):S41, 2012.
Plevy, S. et al., "Combined serological, genetic, and inflammatory markers differentiate non-IBD, Crohn's disease, and ulcerative colitis patients," Inflammatory Bowel Diseases, 19(6):1139-48, 2013.
Todoroki, K. et al., "Online photocatalytic device for highly selective pre-column fluorescence derivatization of 5-hydroxyindoles with benzylamine," Analytica Chimica Acta, 555(1):14-19, 2006.
Yamagishi, Y. et al., "Ribosomal synthesis of cyclic peptides with a fluorogenic oxidative coupling reaction," Chembiochem, 10(9):1469-1472, 2009.

* cited by examiner

*Primary Examiner* — Changhwa J Cheu
(74) *Attorney, Agent, or Firm* — Kilpatrick Townsend & Stockton LLP

(57) ABSTRACT

The present invention provides methods for aiding in the diagnosis of irritable bowel syndrome (IBS) in an individual. In particular, the present invention is useful for determining whether the individual does not have either celiac disease or inflammatory bowel disease (IBD), and has IBS and/or a subtype thereof. Thus, the present invention provides an accurate diagnostic prediction of IBS and is useful for guiding treatment decisions.

15 Claims, 22 Drawing Sheets

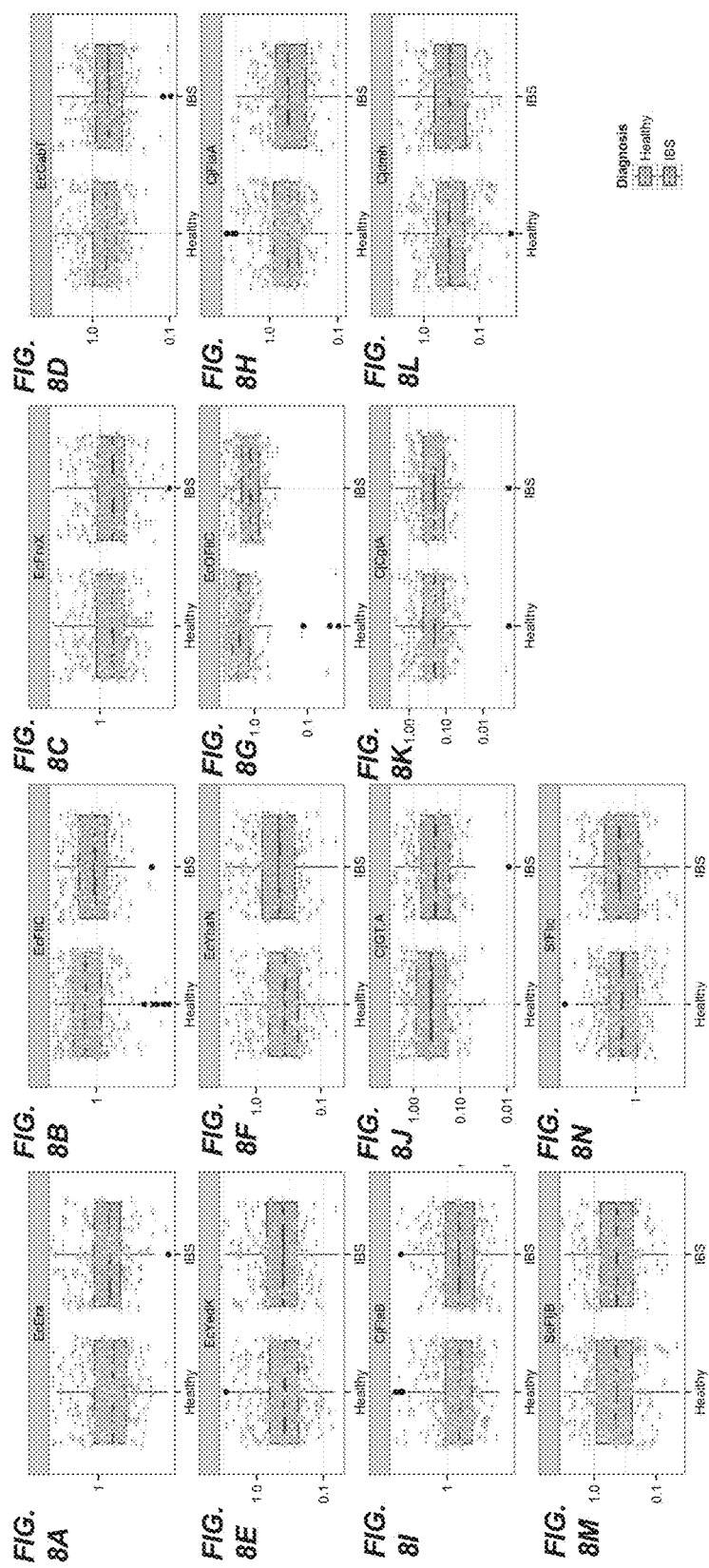

1) Logistic regressions including all of the markers.
   Lines represent βs (coefficients from regression/slope).
   Positive for IBS.
   Negative for healthy controls.
2) Quartile from healthy controls.
3) Calculate Microbiome Score per subject.

Weighted quartile sum score:
   $\Sigma \, \beta * \text{quartile}$ over all markers

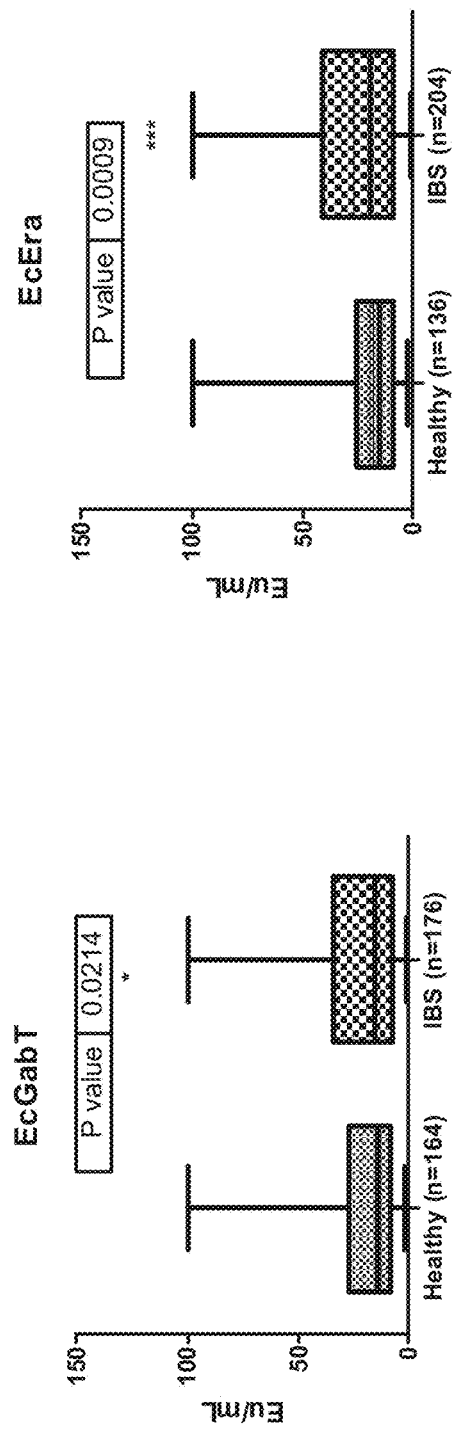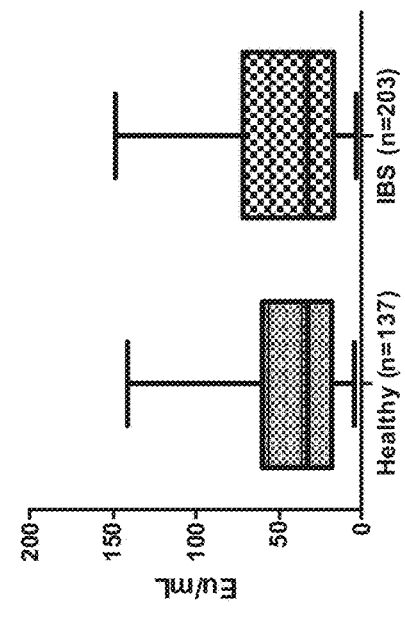
FIG. 13A  FIG. 13B  FIG. 13C

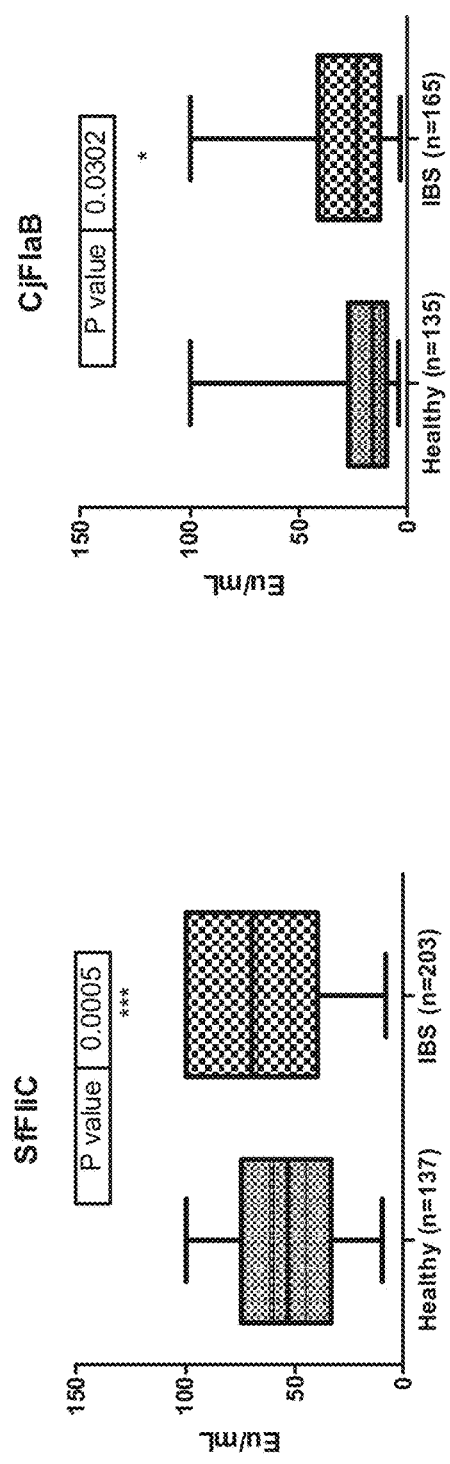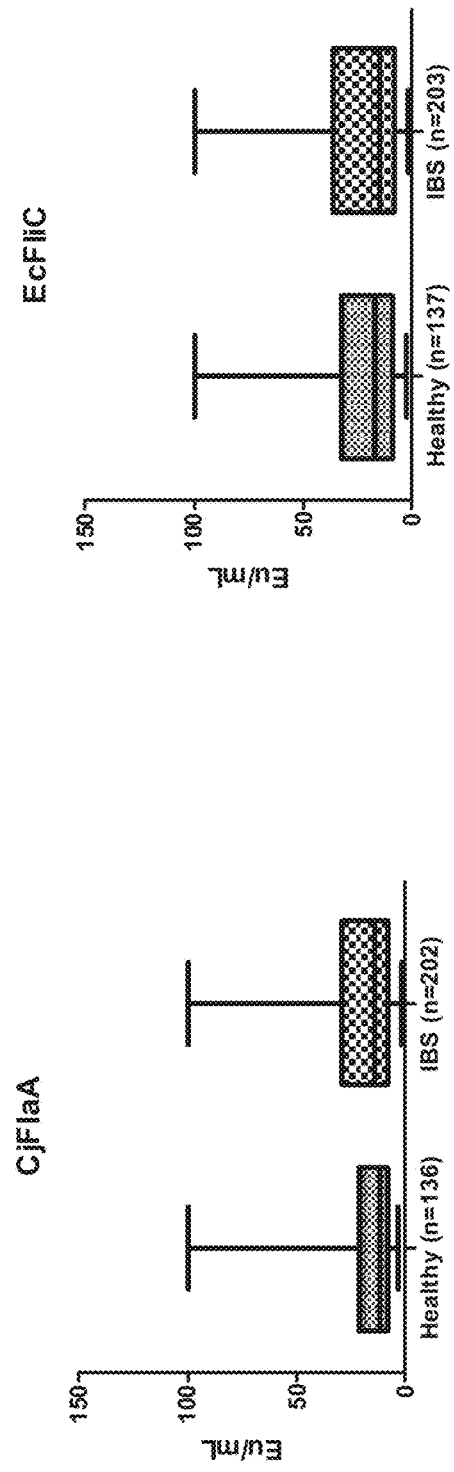

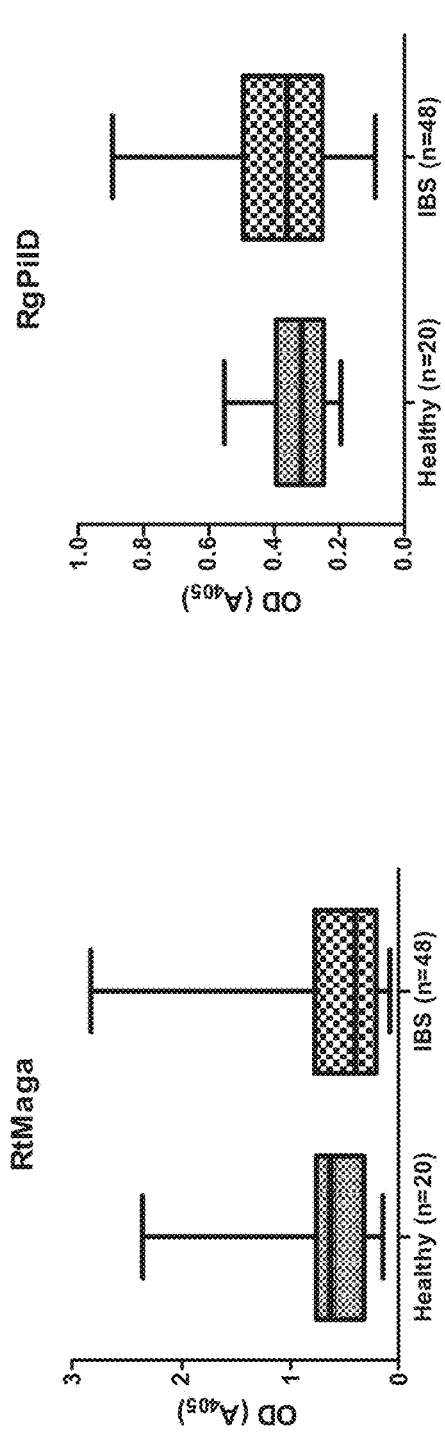
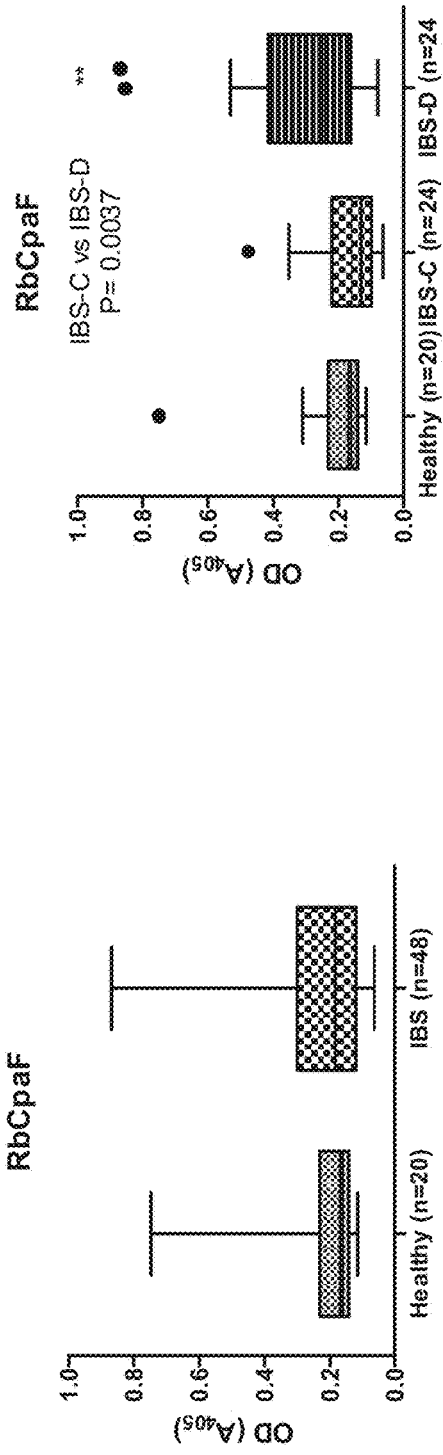

| | Number of subjects | Mean 5-HT in nM |
|---|---|---|
| Healthy | 73 | 33 ± 10 |
| IBS-D | 47 | 55 ± 10 |

| IBS-D | 5-HT in nM |
|---|---|
| Q1 | 38.55 |
| Q2 | 49.05 |
| Q3 | 64.9 |
| Q4 | 140.6 |

Q3, Q4: Indicates Serotonin dysfunction

*FIG. 15C*

PATHWAY SPECIFIC MARKERS FOR DIAGNOSING IRRITABLE BOWEL SYNDROME

CROSS-REFERENCES TO RELATED APPLICATIONS

The present application is a continuation of U.S. patent application Ser. No. 15/646,838, filed Jul. 11, 2017 (Allowed), which is a continuation of U.S. patent application Ser. No. 14/938,729, filed Nov. 11, 2015, which issued as U.S. Pat. No. 9,739,786, which is a continuation of International Patent Application No. PCT/IB2014/061636, filed May 22, 2014, which application claims priority to U.S. Provisional Application No. 61/827,506, filed May 24, 2013, the disclosures of which are hereby incorporated by reference in its entirety for all purposes. This application incorporates by reference PCT/IB2014/061634.

BACKGROUND OF THE INVENTION

Irritable bowel syndrome (IBS) is the most common of all gastrointestinal disorders, affecting 10-20% of the general population and accounting for more than 50% of all patients with digestive complaints. However, studies suggest that only about 10% to 50% of those afflicted with IBS actually seek medical attention. Patients with IBS present with disparate symptoms such as, for example, abdominal pain predominantly related to defecation, diarrhea, constipation or alternating diarrhea and constipation, abdominal distention, gas, and excessive mucus in the stool. More than 40% of IBS patients have symptoms so severe that they have to take time off from work, curtail their social life, avoid sexual intercourse, cancel appointments, stop traveling, take medication, and even stay confined to their house for fear of embarrassment. The estimated health care cost of IBS in the United States is $8 billion per year (Talley et al., *Gastroenterol.*, 109:1736-1741 (1995)).

IBS patients are classified into three groups according to their predominant bowel symptoms: constipation-predominant IBS (IBS-C), diarrhea-predominant IBS (IBS-D) and IBS with alternating symptoms of diarrhea and constipation (IBS-M), and unsubtyped IBS (IBS-U). In current clinical practice, diagnosis of IBS is based on the Rome III criteria and according to the symptoms presented by the patients plus the exclusion of other GI disorders. There are no specific biological, radiographic, endoscopic or physiological biomarkers that can be used to identify this disorder.

Irritable bowel syndrome is a heterogeneous gastrointestinal (GI) function disorder. There is increasing evidence pointing to the involvement of the immune system in its pathogenesis. GI infection may be a triggering factor for causing the onset of IBS symptoms. On the other hand, IBS is often described as a "brain-gut disorder". Alterations in GI motility and secretion mediated by dysregulation of the 5-HT signaling pathway may underlie the irregularities in bowel habits. Activation of mast cells in proximity to colonic nerves correlated with the abnormal pain experienced by patients with IBS. Mast cells are well known to be capable of producing and releasing a variety of inflammatory mediators upon activation. However, it is not clear how these different pathways communicate with each other and whether their interactions behave in the same manner in IBS patients as it is in healthy subjects.

The precise pathophysiology of IBS remains to be elucidated. While gut dysmotility and altered visceral perception are considered important contributors to symptom pathogenesis (Quigley, *Scand. J. Gastroenterol.*, 38(Suppl. 237): 1-8 (2003); Mayer et al., *Gastroenterol.*, 122:2032-2048 (2002)), this condition is viewed as a stress-related disorder characterized by disturbed brain-gut communication, enteric infection, intestinal inflammation, and/or altered microbiota (see, FIG. 1). Recently, roles for enteric infection and intestinal inflammation have also been proposed. Studies have documented the onset of IBS following bacteriologically confirmed gastroenteritis, while others have provided evidence of low-grade mucosal inflammation (Spiller et al., *Gut*, 47:804-811 (2000); Dunlop et al., *Gastroenterol.*, 125: 1651-1659 (2003); Cumberland et al., *Epidemiol. Infect.*, 130:453-460 (2003)) and immune activation (Gwee et al., *Gut*, 52:523-526 (2003); Pimentel et al., *Am. J. Gastroenterol.*, 95:3503-3506 (2000)) in IBS. The enteric flora (e.g., gut microbiome) has also been implicated, and a recent study demonstrated the efficacy of the probiotic organism *Bifidobacterium* in treating the disorder through modulation of immune activity (Simren et al., *Gut*, 62:159-176 (2013)).

There is a growing body of evidence supporting the role of antimicrobial antibodies, stress hormones, inflammatory cytokines, and mast cell markers in various intestinal diseases or disorders. For instance, the antimicrobial antibodies OmpC, Cbir1, FlaX and Fla2 have been proven to be valuable biomarkers of inflammatory bowel disease (IBD). Subsets of antibodies to *Escherichia coli* K12 proteins (e.g., Era, FocA, FrvX, GabT, YbaN, YcdG, YhgN, and YidX) can be used to distinguish between individuals with Crohn's Disease (CD) and healthy controls, and between individuals with CD and ulcerative colitis (Chen et al., *Mol. Cell Proteomics*, 8:1765-1776, (2009)). Individuals with post-infectious small intestine bacterial outgrowth (SIBO) associated with IBS which is often caused by infection from *Campylobacter jejuni* (*C. jejuni*, Cj), *Escherichia coli* (*E. coli*, Ec), *Salmonella enteritidis* (*S. enteritidis*, Se), *Shigella flexneri* (*S. flexneri*, Sf), may possess antibodies against flagellin proteins of the infecting bacteria (Spiller R and Garsed K., *Gastroenterology*, 136:1979-1988 (2009)).

Increased mast cell infiltration and activation in distal gut segments are associated with symptom onset and severity of IBS. These cells are also implicated in the elevated response of visceral afferent nerves to mucosal stimulus in IBS patients. Mast cell hyperplasia is commonly observed following infection by these bacteria in both post-infectious IBS and non-post-infectious IBS. Measurements of mast cell markers such as β-tryptase, histamine and prostaglandin E2 (PGE2) have important implications in the clinical diagnosis of IBS. Detailed methods of using mast cell markers to aid in the diagnosis of IBS are described in U.S. Pat. Nos. 8,114,616 and 8,709,733, the disclosures of which are hereby incorporated by reference in their entireties for all purposes.

IBS patients typically experience abnormal gut motility and visceral hypersensitivity mediated by the brain-gut axis and the gut microbiome (FIG. 1). In stress-sensitive disorders including IBS, stress hormones of the hypothalamic-pituitary-adrenal axis (HPA) axis, such as gut hormones, serotonin, adrenocorticotropin hormone (ACTH), cortisol, corticotropin-releasing hormone, and catecholamine are released, thus controlling the physiological function of, for example, the gut. Dysregulation of the brain-gut axis including the metabolite driven pathways, such as the tryptophan pathway, kynurenine pathway and serotonin pathway (FIG. 2) can adversely affect gastrointestinal function by decreasing motility and increasing pain or discomfort. Therapeutics drugs directed to the serotonin pathway are currently under investigation for the treatment of IBS. Dysregulation of intestinal bile acid secretion and absorption is also associated with IBS (FIG. 3). Some studies have also shown that gastrointestinal function is affected by the gut microbiome (FIG. 4). For instance, diet, antibiotics, pathogens, and the host's immune response can change the gut's microbiome community, which in turn, can alter intestinal function.

In view of the foregoing, there is a need in the art for methods for diagnosing IBS in an individual by monitoring the brain-gut-microbiome axis. The present invention satisfies this and other needs.

BRIEF SUMMARY OF THE INVENTION

In some aspects, provided herein is a method for aiding in the diagnosis of irritable bowel syndrome (IBS) and/or a clinical subtype thereof in a subject.
The method comprises:
 (a) detecting in a sample a panel of markers to rule-out a diagnosis of inflammatory bowel disease and celiacs disease (CD); and
 (b) detecting in the sample a panel of markers to rule-in a diagnosis of IBS.

In certain instances, the method comprises obtaining one or more of the following scores (a)-(h): (a) detecting in a sample obtained from said subject the presence or absence of an anti-gliadin IgA antibody, an anti-gliadin IgG antibody, an anti-tissue transglutaminase (tTG) antibody, and an anti-endomysial antibody to obtain a celiac disease (CD) score; (b) detecting in said sample the presence or level or genotype of at least each of the following markers to obtain an inflammatory bowel disease (IBD) score: (i) the presence or level of each of the serological markers ASCA-A, ASCA-G, ANCA, pANCA, anti-OmpC antibody, anti-CBir1 antibody, anti-FlaX antibody, and anti-A4-Fla2 antibody; (ii) the presence or level of each of the inflammation markers VEGF, ICAM, VCAM, SAA, and CRP; and (iii) the genotype of each of the genetic markers ATG16L1, ECM1, NKX2-3, and STAT3; (c) detecting in said sample the level (e.g., concentration) of at least one bacterial antigen antibody marker to obtain a microbiome score; (d) detecting in said sample the level (e.g., concentration) of at least one mast cell marker to obtain a mast cell score; (e) detecting in said sample the level (e.g., concentration) of at least one inflammatory cell marker to obtain an inflammatory score; (f) detecting in said sample the level (e.g., concentration) of at least one bile acid malabsorption (BAM) marker to obtain a BAM score; (g) detecting in said sample the level (e.g., concentration) of at least one kynurenine marker to obtain an oxidative stress score; (h) detecting in said sample the level (e.g., concentration) of at least one serotonin marker to obtain a serotonin score; (j) if said sample is a non-CD sample, then applying a random forest statistical analysis to said IBD score to obtain a decision whether the sample is an IBD sample or a non-IBD sample; (k) if said sample is a non-IBD sample, then applying a statistical algorithm to said microbiome score, said mast cell score, said inflammatory score, said BAM score, said oxidative stress score, and said serotonin score to obtain a disease score; and (l) determining a diagnosis of IBS in said subject based on a statistical algorithm that generates a probability of having IBS based the disease score and a diagnostic model comprising a microbiome score, mast cell score, an inflammatory score, a bile acid malabsorption score, an oxidative stress score, and a serotonin score from a retrospective cohort of patients.

In some embodiments, the at least one bacterial antigen antibody marker is selected from the group consisting of an anti-Fla1 antibody, anti-Fla2 antibody, anti-FlaA antibody, anti-FliC antibody, anti-FliC2 antibody, anti-FliC3 antibody, anti-YBaN1 antibody, anti-ECFliC antibody, anti-Ec0FliC antibody, anti-SeFljB antibody, anti-CjFlaA antibody, anti-CjFlaB antibody, anti-SfFliC antibody, anti-CjCgtA antibody, anti-Cjdmh antibody, anti-CjGT-A antibody, anti-EcYidX antibody, anti-EcEra antibody, anti-EcFrvX antibody, anti-EcGabT antibody, anti-EcYedK antibody, anti-EcYbaN antibody, anti-EcYhgN antibody, anti-RtMaga antibody, anti-RbCpaF antibody, anti-RgPilD antibody, anti-LaFrc antibody, anti-LaEno antibody, anti-LjEFTu antibody, anti-BfOmpa antibody, anti-PrOmpA antibody, anti-Cp10bA antibody, anti-CpSpA antibody, anti-EfSant antibody, anti-LmOsp antibody, anti-SfET-2 antibody, anti-Cpatox antibody, anti-Cpbtox antibody, anti-EcSta2 antibody, anti-Ec0Stx2A antibody, anti-CjcdtB/C antibody, anti-CdtcdA/B antibody, and combinations thereof.

In some embodiments, the at least one mast cell marker is selected from the group consisting of β-tryptase, histamine, prostaglandin E2 (PGE2), and combinations thereof.

In some embodiments, the at least one inflammatory marker is selected from the group consisting of CRP, ICAM, VCAM, SAA, GROα, and combinations thereof.

In some embodiments, the at least one bile acid malabsorption marker is selected from the group consisting of 7α-hydroxy-4-cholesten-3-one, FGF19, and a combination thereof.

In some embodiments, the at least one kynurenine marker is selected from the group consisting of kynurenine (K), kynurenic acid (KyA), anthranilic acid (AA), 3-hydroxykynurenine (3-HK), 3-hydroxyanthranilic acid (3-HAA), xanthurenic acid (XA), quinolinic acid (QA), tryptophan, 5-hydroxytryptophan (5-HTP), and combinations thereof.

In some embodiments, the at least one serotonin markers is selected from the group consisting of serotonin (5-HT), 5-hydroxyindoleacetic acid (5-HIAA), serotonin-O-sulfate, serotonin-O-phosphate, and combinations thereof.

In some embodiments, the diagnostic model is established using a retrospective cohort with known outcomes of IBS and healthy controls. In other embodiments, the diagnostic model is established using a retrospective cohort with known outcomes of a clinical subtype of IBS and healthy controls.

In some embodiments, the method further comprises classifying a diagnosis of IBS as IBS-constipation (IBS-C), IBS diarrhea (IBS-D), IBS-mixed (IBS-M), IBS-alternating (IBS-A), or post-infectious (IBS-PI).

In some embodiments, the level of said bacterial antigen antibody marker, said mast cell marker, said inflammatory cell marker, said BAM marker, said kynurenine marker or said serotonin marker is independently detected with a hybridization assay, amplification-based assay, immunoassay, immunohistochemical assay, or a mobility assay. In some instances, the hybridization assay comprises an ELISA or a CEER™ assay.

In some embodiments, the sample is selected from the group consisting of whole blood, plasma, serum, saliva, urine, stool, tears, any other bodily fluid, a tissue sample, and a cellular extract thereof. In some instances, the sample is serum.

In some embodiments, at least 1, 2, 3, 4, 5, or 6 of the following scores are measured: microbiome score, a mast cell score, an inflammatory score, a bile acid malabsorption score, an oxidative stress score, and a serotonin score.

In some aspects, provided herein is a method for aiding in the diagnosis of irritable bowel syndrome (IBS) and/or a clinical subtype thereof in a subject. The method comprises obtaining one or more of the following (a) through (f) scores: (a) detecting in a sample obtained from said subject the level of at least one bacterial antigen antibody marker to obtain a microbiome score; (b) detecting in said sample the level of at least one mast cell marker to obtain a mast cell score; (c) detecting in said sample the level of at least one inflammatory cell marker to obtain an inflammatory score; (d) detecting in said sample the level of at least one bile acid malabsorption (BAM) marker to obtain a BAM score; (e) detecting in said sample the level of at least one kynurenine marker to obtain an oxidative stress score; (f) detecting in said sample the level of at least one serotonin marker to obtain a serotonin score; (g) applying a statistical algorithm to said microbiome score, said mast cell score, said inflammatory score, said BAM score, said oxidative stress score, and said serotonin score to obtain a disease score; and (h) determining a diagnosis of IBS in said subject based on a statistical algorithm that generates a probability of having IBS based the disease score and a diagnostic model comprising a microbiome score, mast cell score, an inflammatory score, a bile acid malabsorption score, an oxidative stress score, and a serotonin score from a retrospective cohort.

In some embodiments, the at least one bacterial antigen antibody marker is selected from the group consisting of an anti-Fla1 antibody, anti-Fla2 antibody, anti-FlaA antibody, anti-FliC antibody, anti-FliC2 antibody, anti-FliC3 antibody, anti-YBaN1 antibody, anti-ECFliC antibody, anti-EcOFliC antibody, anti-SeFljB antibody, anti-CjFlaA antibody, anti-CjFlaB antibody, anti-SfFliC antibody, anti-CjCgtA antibody, anti-Cjdmh antibody, anti-CjGT-A antibody, anti-EcYidX antibody, anti-EcEra antibody, anti-EcFrvX antibody, anti-EcGabT antibody, anti-EcYedK antibody, anti-EcYbaN antibody, anti-EcYhgN antibody, anti-RtMaga antibody, anti-RbCpaF antibody, anti-RgPilD antibody, anti-LaFrc antibody, anti-LaEno antibody, anti-LjEFTu antibody, anti-BfOmpa antibody, anti-PrOmpA antibody, anti-Cp10bA antibody, anti-CpSpA antibody, anti-EfSant antibody, anti-LmOsp antibody, anti-SfET-2 antibody, anti-Cpatox antibody, anti-Cpbtox antibody, anti-EcSta2 antibody, anti-EcOStx2A antibody, anti-CjcdtB/C antibody, anti-CdtcdA/B antibody, and combinations thereof.

In some embodiments, the at least one mast cell marker is selected from the group consisting of β-tryptase, histamine, prostaglandin E2 (PGE2), and combinations thereof.

In some embodiments, the at least one inflammatory marker is selected from the group consisting of CRP, ICAM, VCAM, SAA, GROα, and combinations thereof.

In some embodiments, the at least one bile acid malabsorption marker is selected from the group consisting of 7α-hydroxy-4-cholesten-3-one, FGF19, and a combination thereof.

In some embodiments, the at least one kynurenine marker is selected from the group consisting of kynurenine (K), kynurenic acid (KyA), anthranilic acid (AA), 3-hydroxykynurenine (3-HK), 3-hydroxyanthranilic acid (3-HAA), xanthurenic acid (XA), quinolinic acid (QA), tryptophan, 5-hydroxytryptophan (5-HTP), and combinations thereof.

In some embodiments, the at least one serotonin markers is selected from the group consisting of serotonin (5-HT), 5-hydroxyindoleacetic acid (5-HIAA), serotonin-O-sulfate, serotonin-O-phosphate, and combinations thereof.

In some embodiments, the diagnostic model is established using a retrospective cohort with known outcomes of IBS and healthy controls. In other embodiments, the diagnostic model is established using a retrospective cohort with known outcomes of a clinical subtype of IBS and healthy controls.

In some embodiments, the method further comprises classifying a diagnosis of IBS as IBS-constipation (IBS-C), IBS diarrhea (IBS-D), IBS-mixed (IBS-M), IBS-alternating (IBS-A), or post-infectious (IBS-PI).

In some embodiments, at least 1, 2, 3, 4, 5, or 6 of the following scores are measured: microbiome score, a mast cell score, an inflammatory score, a bile acid malabsorption score, an oxidative stress score, and a serotonin score.

In some embodiments, the presence or absence or level of said bacterial antigen antibody marker, said mast cell marker, said inflammatory cell marker, said BAM marker, said kynurenine marker or said serotonin marker is independently detected with a hybridization assay, amplification-based assay, immunoassay, immunohistochemical assay, or a mobility assay. In some instances, the hybridization assay comprises an ELISA or a CEER™ assay.

Other objects, features, and advantages of the present invention will be apparent to one of skill in the art from the following detailed description and figures.

BRIEF DESCRIPTION OF THE DRAWINGS

FIG. 6A shows that bacterial antigen antibody markers and one inflammatory marker are predictive of IBS. FIG. 6B shows that bacterial antigen antibody markers, one inflammatory marker, and one mast cell marker are predictive of IBS.

FIGS. 8A-8N shows the levels of specific bacterial antigen antibody markers in healthy controls and IBS patients. The microbiome markers include EcEra (FIG. 8A), EcFliC (FIG. 8B), EcFrvX (FIG. 8C), EcGabT (FIG. 8D), EcYedK (FIG. 8E), EcYbaN (FIG. 8F), EcOFliC (FIG. 8G), CjFlaA (FIG. 8H), CjFlaB (FIG. 8I), CjGT-A (FIG. 8J), CjCgtA (FIG. 8K), Cjdmh (FIG. 8L), SeFljB (FIG. 8M), and SfFliC (FIG. 8N).

FIGS. 9A and 9B shows that the weights for each biomarker (e.g., EcEra and EcFliC) are determined from coefficients of the regression or slope between the disease cohort and the healthy cohort. The lines in FIGS. 9A and 9B represent βs. A positive slope indicates IBS and negative slope indicates healthy control. For each individual, the weighted quartile sum score is represented as Σβ* quartile over all markers, wherein β represents the coefficients form the regression or slope between the cohorts (FIG. 9C). The coefficients are adjusted for the presence of other markers. FIG. 9C shows an exemplary embodiment of the quartile analysis described herein.

FIGS. 13A-13K show the level of different bacterial antigen antibody markers in cohort #2 containing healthy controls and IBS patients including those with IBS-C and IBS-D. The markers shown are EcGabT (FIG. 13A), EcEra (FIG. 13B), EcOFliC (FIG. 13C), SfFliC (FIG. 13D), CjFlaB (FIG. 13E), CjFlaA (FIG. 13F), EcFliC (FIG. 13G), RtMaga (FIG. 13H), RtPilD (FIG. 13I), and RbCpaF (FIGS. 13J and 13K).

FIGS. 15A-15C show the level of serotonin in healthy controls and IBS patients as determined by HPLC. FIG. 15A shows a graph of serotonin levels. FIG. 15B shows a chromatogram of serotonin and serotonin metabolites. FIG. 15C provides a table of serotonin levels.

FIG. 16A shows a graph of serotonin levels in IBS-D patients. FIG. 16B provides a table of the results.

DETAILED DESCRIPTION OF THE INVENTION

I. Introduction

Diagnosing a patient as having irritable bowel syndrome can be challenging due to the similarity in symptoms between IBS and other intestinal diseases or disorders. Biomarker-based assays can provide rapid and accurate diagnostic methods to distinguish IBS from other diseases and disorders.

Although the precise pathophysiology of IBS remains to be elucidated. It is believed that IBS is caused, in part, by dysregulation of the host's microbiome in the gut and stress hormones. Studies have shown that the gastrointestinal microbiota can influence the host and results in mucosal inflammation and immune activation, and that cortisol levels can be high in women with IBS (Heitkemper et al., *Am J Gastroenterol*, 91(5):906-13 (1996)).

Observations supporting this theory include the finding that an increased number of mast cells can be found in the gastrointestinal mucosa of patients diagnosed with IBS (Guilarte, M. et al., *Gut* 56, 203-209 (2007); Walker, M. M. et al., *Pharmacol. Ther.*, 29, 765-773 (2009); Akbar, A. et al., *Gut* 57, 923-929 (2008); Barbara, G. et al., *Gastroenterology* 126, 693-702 (2004); Barbara, G. et al., *Gastroenterology* 132, 26-37 (2007); Cremon, C. et al., *Am. J. Gastroenterol.* 104, 392-400 (2009); and O'Sullivan, M. et al., *Neurogastroenterol. Motil.*, 12, 449-457 (2000)). Similarly, some studies have also found that levels of mediators released from these cells, including histamine and serine proteases (e.g., tryptase), are found in the colonic mucosa of IBS patients (Buhner et al., *Gastroenterology*, 137(4), (2009)); Barbara et al., *Gastroenterology*, 122(4), Suppl. 1: A-276, (2002)).

The human gastrointestinal microbiota includes at least 1,000 species of bacteria, and about $10^{14}$ individual bacterial cells from about 160 different species inhabit each individual's intestine (Qin et al., *Nature*, 464:59-65 (2010)). It has been theorized that the host's (e.g., individual's) genetic and immune composition as well as environmental factors influence the gastrointestinal microbiota, which in turn shapes the host's immunity and physiology within the gastrointestinal system. This theory suggests that a healthy individual (e.g., free of intestinal disorders or disease) maintains a symbiotic relationship with the microbiota colonizing his/her intestines, while an individual with IBS has an imbalance in this microbiota-immune interaction.

Figure 1:
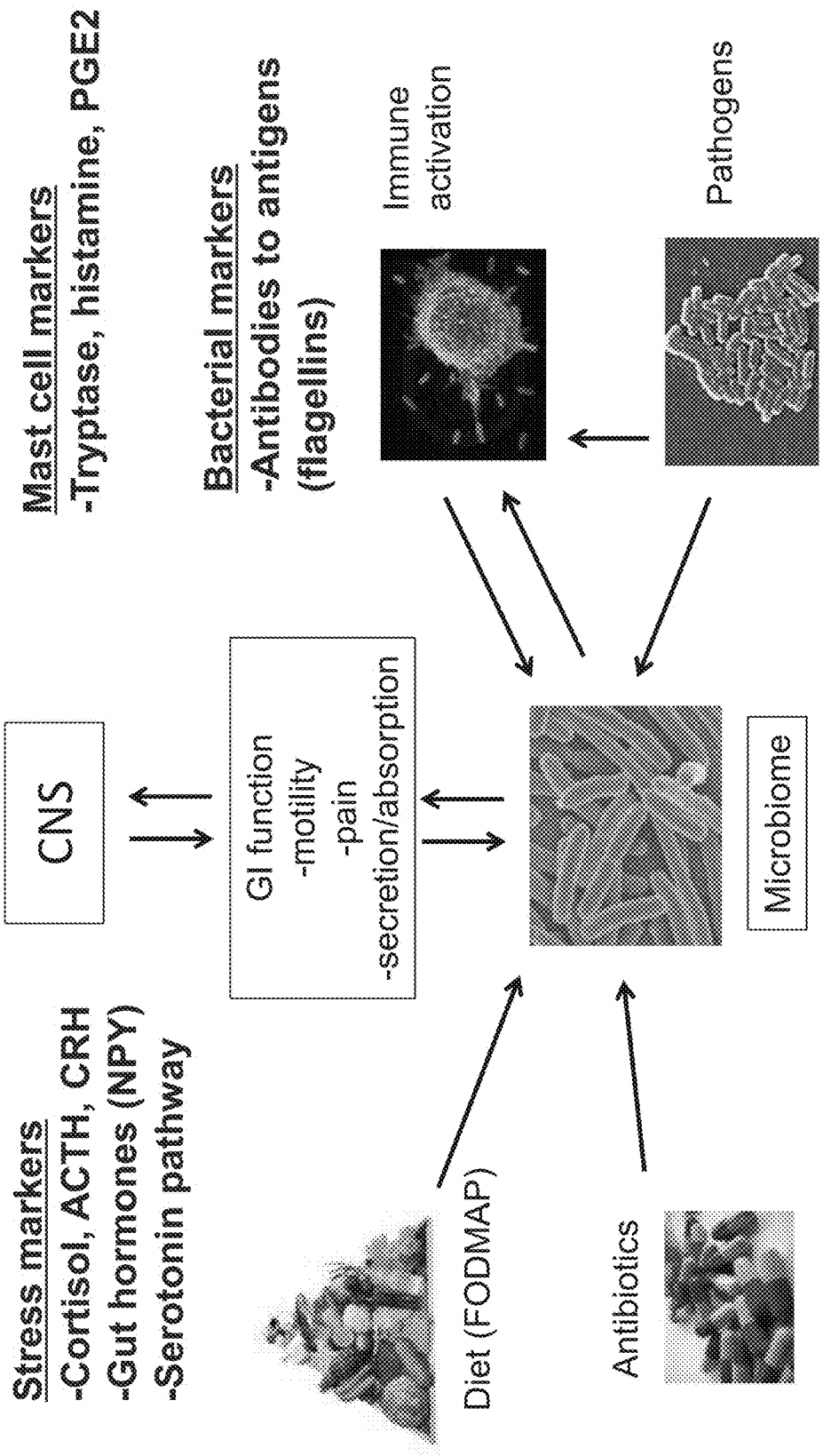
FIG. 1 illustrates the brain-gut-microbiome axis and the complex pathophysiology of IBS. It highlights some of the biomarkers described herein that can be used for the diagnosis of IBS and/or subtypes thereof.
Figure 2:
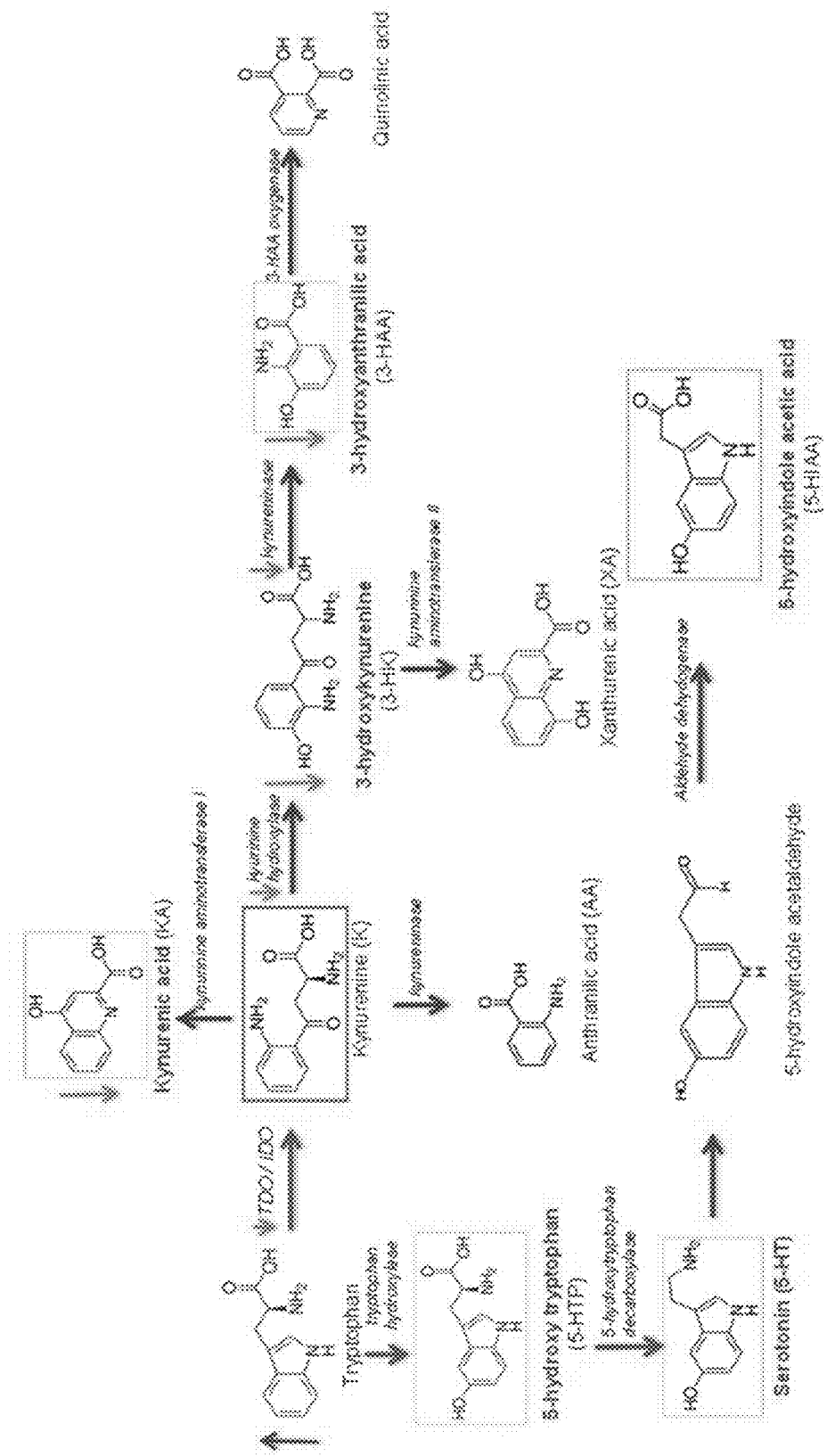
FIG. 2 shows metabolite driven pathways and enzymes that are dysregulated in IBS patients. In patients with IBS-D, tryptophan levels are increased while kynurenic acid (KA), 3-hydroxykynurenine (3-HK), and 3-hydroxyanthranilic acid (3-HAA) levels are decreased. In addition, the activity of the enzymes, such as tryptophan dioxygenase/indoleamine 2,3-dioxygenase (TDO/IDO), kynurenine hydroxylase, and kynureninase are lower (decreased).
Figure 3:
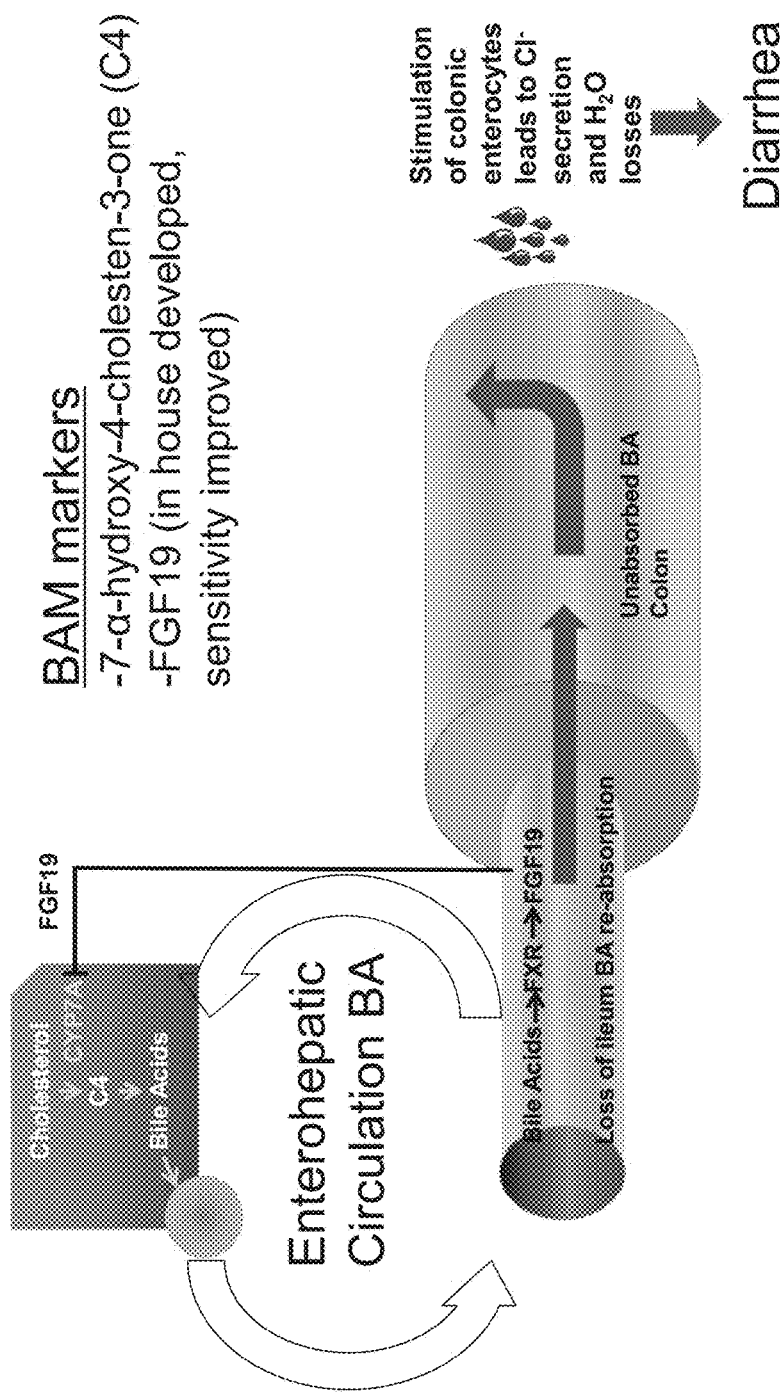
FIG. 3 shows a diagram of the intestinal bile acid secretion and absorption pathway.
Figure 4:
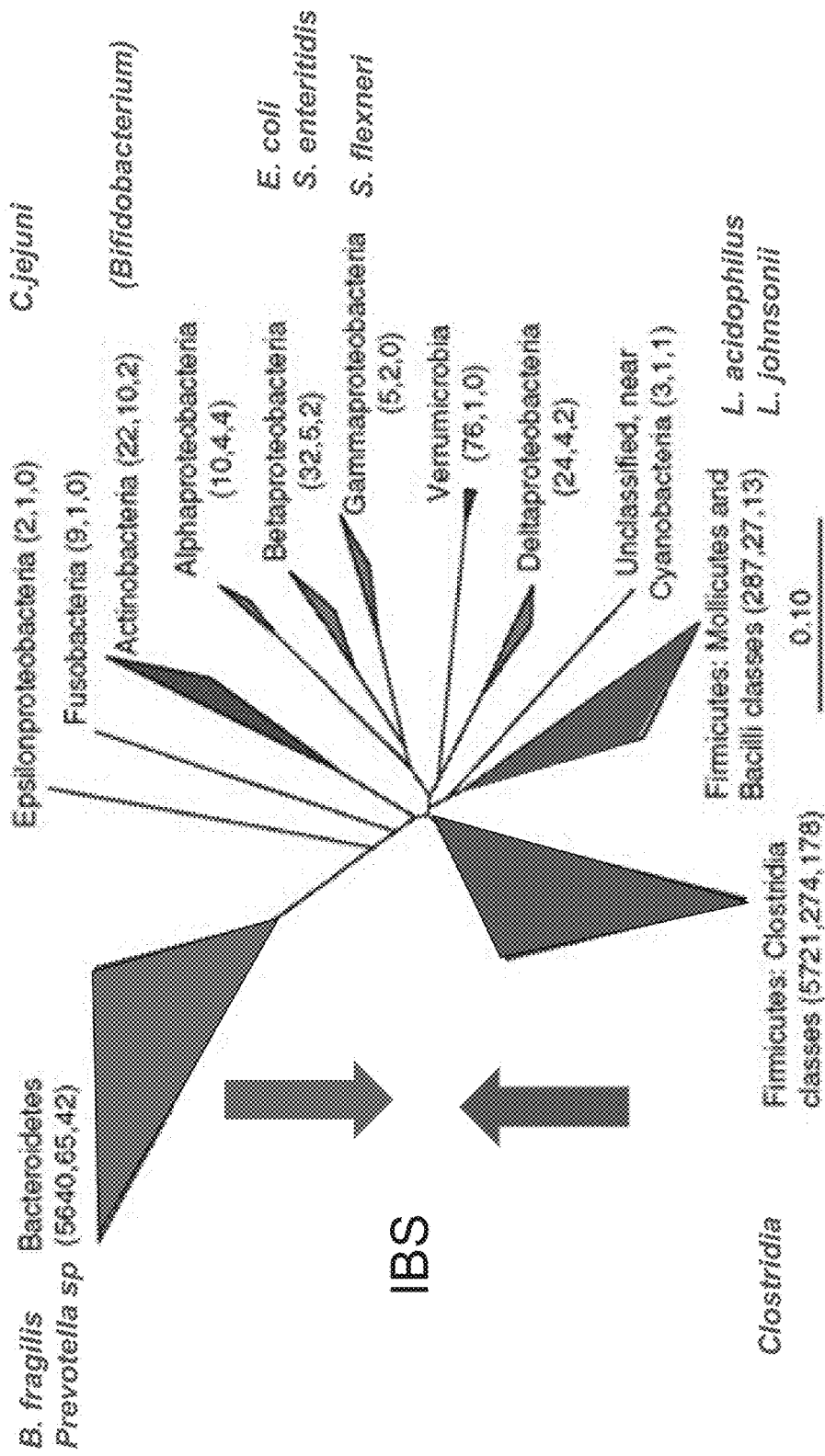
FIG. 4 illustrates the diversity of the gut microbiome.

The serotonin pathway plays a critical role in the regulation of gastrointestinal motility, secretion, and sensation. Imbalances in this pathway within the enteric nervous system have been associated with various disorders, such as IBS, functional dyspepsia, non-cardiac chest pain, autism, and gastric ulcer formation. Significant alterations of the tryptophan/serotonin/kynurenine metabolic and catabolic pathways (FIG. 2) have been implicated in IBS-D (Christmas et al., Nutrition Research, 2010, 30:678-688).

The present invention provides methods for diagnosing irritable bowel syndrome (IBS) in a subject. The methods include measuring the level of an array of celiac disease (CD) markers, IBD markers, microbiome markers, mast cell markers, inflammatory markers, bile acid malabsorption markers, kynurenine markers, and serotonin markers in a biological sample taken from the subject; generating a series of biomarker scores; and using an algorithm to determine whether the subject does not have CD or IBD and has an increased likelihood of having IBS compared to being a healthy control. The present invention also provides methods and assays for measuring the level of various biomarkers.

II. Definitions

As used herein, the following terms have the meanings ascribed to them unless specified otherwise.

The terms "irritable bowel syndrome" and "IBS" includes a group of functional bowel disorders characterized by one or more symptoms including, but not limited to, abdominal pain, abdominal discomfort, change in bowel pattern, loose or more frequent bowel movements, diarrhea, and constipation, typically in the absence of any apparent structural abnormality. There are at least three forms of IBS, depending on which symptom predominates: (1) diarrhea-predominant (IBS-D); (2) constipation-predominant (IBS-C); and (3) IBS with alternating stool pattern (IBS-A). IBS can also occur in the form of a mixture of symptoms (IBS-M). There are also various clinical subtypes of IBS, such as post-infectious IBS (IBS-PI).

The terms "celiac disease" and "CD" refer to a disorder of the intestinal mucosa that is typically associated with villous atrophy, crypt hyperplasia, and/or inflammation of the mucosal lining of the small intestine. In addition to the malabsorption of nutrients, individuals with Celiac disease are at risk for mineral deficiency, vitamin deficiency, osteoporosis, autoimmune diseases, and intestinal malignancies (e.g., lymphoma and carcinoma). Without being bound by any particular theory, it is thought that exposure to proteins such as gluten (e.g., glutenin and prolamine proteins which are present in wheat, rye, barley, oats, millet, triticale, spelt, and kamut), in the appropriate genetic and environmental context, is responsible for causing Celiac disease.

The term "inflammatory bowel disease" or "IBD" includes gastrointestinal disorders such as, e.g., Crohn's disease (CD), ulcerative colitis (UC), indeterminate colitis (IC), and IBD that is inconclusive for CD vs. UC ("Inconclusive"). Inflammatory bowel diseases (e.g., CD, UC, IC, and Inconclusive) are distinguished from all other disorders, syndromes, and abnormalities of the gastroenterological tract, including irritable bowel syndrome (IBS). Detailed descriptions of methods for diagnosis IBS are found in, e.g., U.S. Pat. Nos. 7,873,479 and 8,715,943, the contents are hereby incorporated by reference in their entirety for all purposes.

The terms "microbiota," "microflora" and "microbiome" refer to the community of living microorganisms that typically inhabits a bodily organ or part. Members of the gastrointestinal microbiota include, but are not limited to, microorganisms of the phyla of Firmicutes, Bacteroidetes, Proteobacteria, Epsilonproteobacteria, Fusobacteria, Alphaproteobacteria, Betaproteobacteria, Gammaproteobacteria, Verrumicrobia, Deltaproteobacteria, Unclassified near cyanobacteria, and Actinobacteria; microorganisms of the *Bacteroides*, *Prevotella* or *Ruminococcus* genera; microorganisms of the *Bifidobacteria*, *Enterobacteraceae*, *Lactobacillus*, *Veillonella*, *Bacteoides*, *Streptococcus*, *Actinomycinaea*, *Helicobacter*, *Peptostreptococcus*, *Collinsella*, *Clostridium*, *Enterococcus*, *Coprococcus*, *Coprobacillus*, *Proteobacteria*, *Lactobacillus*, *Ruminococus*, *Eubacterium*, *Dorea*, *Acinetobacter*, and *Escherichia coli* species; microorganisms of the *Ruminococcus torques*, *R. torques*-like, *Collinsella aerofaciens*-like, *Clostridium cocleatum*, *Eubacterium rectale*, *Clostridium coccoides*, *Rhinobatos productus* types. In some instances, the gastrointestinal microbiota includes the mucosa-associated microbiota, which is located at the surface or apical end of the gastrointestinal tract, and luminal-associated microbiota, which is found in the lumen of the gastrointestinal tract.

The term "biomarker" or "marker" includes any diagnostic marker such as a biochemical marker, serological marker, genetic marker, microbial marker or other clinical or echographic characteristic that can be used to classify a sample from an individual as an IBS sample or to rule out one or more diseases or disorders associated with IBS-like symptoms in a sample from an individual. The term "biomarker" or "marker" also encompasses any classification marker such as an antibody marker, biochemical marker, serological marker, genetic marker, hormonal marker, microbial marker, or other clinical or echographic characteristic that can be used to classify IBS into one of its various forms or clinical subtypes. Non-limiting examples of diagnostic markers suitable for use in the present invention are described below and include antibodies against bacterial antigens, bacterial antigens, flagellins, cytokines, growth factors, stress hormones, anti-neutrophil antibodies, anti-*Saccharomyces cerevisiae* antibodies, antimicrobial antibodies, anti-tissue transglutaminase (tTG) antibodies, lipocalins, matrix metalloproteinases (MMPs), tissue inhibitor of metalloproteinases (TIMPs), alpha-globulins, actin-severing proteins, S100 proteins, fibrinopeptides, calcitonin gene-related peptide (CGRP), tachykinins, ghrelin, neurotensin, serotonin, corticotropin-releasing hormone (CRH), serine proteases (e.g., β-tryptase, elastase), prostaglandin (e.g., PGE2), histamine, C-reactive protein (CRP), lactoferrin, anti-lactoferrin antibodies, calprotectin, hemoglobin, NOD2/CARD15, serotonin reuptake transporter (SERT), tryptophan hydroxylase-1, 5-hydroxytryptamine (5-HT), lactulose, and the like. In preferred embodiments, diagnostic markers suitable for use in the present invention are described herein and include, without limitation, an antibody that binds to a microbiota antigen selected from the group consisting of *E. coli* FliC, *S. flexneri* FliC, *C. jejuni* FlaA, *C. jejuni* FlaB, *E. coli* O157:H7 FliC, *E. coli* FrvX, *E. coli* GabT, *C. jejuni* 81-045, *C. jejuni* 81-128, and *C. jejuni* 81-008, *E. coli* Era, *E. coli* FocA, *E. coli* FrvX, *E. coli* GabT, *E. coli* YbaN, *E. coli* YcdG, *E. coli* YhgN, *E. coli* YedK, *E. coli* YidX, *L. acidophilus* Frc, *L. acidophilus* Eno, *L. johnsonii* EFTu, *B. fragilis* OmpA, *Prevotella* OmpA, *C. perfringens* 10bA, *C. perfringens* SpA, *E. faecalis* Sant, *L. monocytogenes* Osp, and mixtures thereof. Examples of classification markers include, without limitation, leptin, SERT, tryptophan hydroxylase-1,5-HT, antrum mucosal protein 8, keratin-8, claudin-8, zonulin, corticotropin releasing hormone receptor-1 (CRHR1), corticotropin releasing hormone receptor-2 (CRHR2), β-tryptase, histamine, prostaglandin E2 (PGE2) and the like. In some embodiments, diagnostic markers can be used to classify IBS into one of its various forms or clinical subtypes. In other embodiments, classification markers can be used to classify a sample as an IBS sample or to rule out one or more diseases or disorders associated with IBS-like symptoms. One skilled in the art will know of additional diagnostic and classification markers suitable for use in the present invention.

The term "estimate" refers to the estimated partial correlation coefficient of a logistic regression model.

The "biological sample" includes any biological specimen obtained from an individual. Suitable samples for use in the present invention include, without limitation, whole blood, plasma, serum, saliva, urine, stool (i.e., feces), tears, and any other bodily fluid, or a tissue sample (i.e., biopsy) such as a small intestine or colon sample, and cellular extracts thereof (e.g., red blood cellular extract). In a preferred embodiment, the sample is a blood, plasma, or serum sample. In a more preferred embodiment, the sample is a serum sample. In certain instances, the term "sample" includes, but is not limited to blood, body tissue, blood serum, lymph fluid, lymph node tissue, spleen tissue, bone marrow, or an immunoglobulin enriched fraction derived from one or more of these tissues. The use of samples such as serum, saliva, and urine is well known in the art (see, e.g., Hashida et al., *J. Clin. Lab. Anal.*, 11:267-86 (1997)). One skilled in the art will appreciate that samples such as serum and blood samples can be diluted prior to the analysis of marker levels.

The term "individual," "subject," or "patient" typically refers to humans, but also to other animals including, e.g., other primates, rodents, canines, felines, equines, ovines, porcines, and the like.

The term "classifying" includes "to associate" or "to categorize" a sample with a disease state. In certain instances, "classifying" is based on statistical evidence, empirical evidence, or both. In certain embodiments, the methods and systems of classifying use a so-called training set of samples having known disease states. Once established, the training data set serves as a basis, model, or template against which the features of an unknown sample are compared, in order to classify the unknown disease state of the sample. In certain instances, classifying the sample is akin to diagnosing the disease state of the sample. In certain other instances, classifying the sample is akin to differentiating the disease state of the sample from another disease state.

As used herein, the term "score" or "profile" includes any set of data that represents the distinctive features or characteristics associated with a disease or disorder such as IBS. The term encompasses a "disease score" or "diagnostic score" that analyzes one or more diagnostic markers in a sample. For example, a "disease score" can include a set of data that represents the presence or level of one or more diagnostic markers associated with IBS.

In some embodiments, a panel for measuring one or more of the diagnostic markers and/or diagnostic model described above can be constructed and used for classifying the sample as an IBS sample or non-IBS sample. One skilled in the art will appreciate that the presence or level of a plurality of diagnostic markers can be determined simultaneously or sequentially, using, for example, an aliquot or dilution of the individual's sample. In certain instances, the level of a particular diagnostic marker in the individual's sample is considered to be elevated when it is at least about 10%, 15%, 20%, 25%, 50%, 75%, 100%, 125%, 150%, 175%, 200%, 250%, 300%, 350%, 400%, 450%, 500%, 600%, 700%, 800%, 900%, or 1000% greater than the level of the same marker in a comparative sample (e.g., a normal, GI control, IBD, and/or celiac disease sample) or population of samples (e.g., greater than a median level of the same marker in a comparative population of normal, GI control, IBD, and/or celiac disease samples). In certain other instances, the level of a particular diagnostic marker in the individual's sample is considered to be lowered when it is at least about 5%, 10%, 15%, 20%, 25%, 30%, 35%, 40%, 45%, 50%, 55%, 60%, 65%, 70%, 75%, 80%, 85%, 90%, or 95% less than the level of the same marker in a comparative sample (e.g., a normal, GI control, IBD, and/or celiac disease sample) or population of samples (e.g., less than a median level of the same marker in a comparative population of normal, GI control, IBD, and/or celiac disease samples).

As used herein, the term "substantially the same amino acid sequence" includes an amino acid sequence that is similar, but not identical to, the naturally-occurring amino acid sequence. For example, an amino acid sequence that has substantially the same amino acid sequence as a naturally-occurring peptide, polypeptide, or protein can have one or more modifications such as amino acid additions, deletions, or substitutions relative to the amino acid sequence of the naturally-occurring peptide, polypeptide, or protein, provided that the modified sequence retains substantially at least one biological activity of the naturally-occurring peptide, polypeptide, or protein such as immunoreactivity. Comparison for substantial similarity between amino acid sequences is usually performed with sequences between about 6 and 100 residues, preferably between about 10 and 100 residues, and more preferably between about 25 and 35 residues. A particularly useful modification of a peptide, polypeptide, or protein of the present invention, or a fragment thereof, is a modification that confers, for example, increased stability. Incorporation of one or more D-amino acids is a modification useful in increasing stability of a polypeptide or polypeptide fragment. Similarly, deletion or substitution of lysine residues can increase stability by protecting the polypeptide or polypeptide fragment against degradation.

The terms "complex," "immuno-complex," "conjugate," and "immunoconjugate" include, but are not limited to, peptide or antigen bound (e.g., by non-covalent means) to an antibody or an antibody fragment.

The term "monitoring the progression or regression of IBS" includes the use of the methods, systems, and code of the present invention to determine the disease state (e.g., presence or severity of IBS) of an individual. In some embodiments, the methods, systems, and code of the present invention can be used to predict the progression of IBS, e.g., by determining a likelihood for IBS to progress either rapidly or slowly in an individual based on an analysis of diagnostic markers and/or the identification or IBS-related symptoms. In other embodiments, the methods, systems, and code of the present invention can be used to predict the regression of IBS, e.g., by determining a likelihood for IBS to regress either rapidly or slowly in an individual based on an analysis of diagnostic markers and/or the identification or IBS-related symptoms.

The term "bacterial antigen antibody marker score, "bacterial antigen antibody score," "microbiome marker score," or "microbiome score" includes the level of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, or more markers of an individual, wherein the markers can be a bacterial antigen antibody marker, such as, but not limited to, an antibody that recognizes (e.g., specifically bind to, forms a complex) with a bacterial antigen, such as Fla1, Fla2, FlaA, FliC, FliC2, FliC3, YBaN1, ECFliC, Ec0FliC, SeFljB, CjFlaA, CjFlaB, SfFliC, CjCgtA, Cjdmh, CjGT-A, EcYidX, EcEra, EcFrvX, EcGabT, EcYedK, EcYbaN, EcYhgN, RtMaga, RbCpaF, RgPilD, LaFrc, LaEno, LjEFTu, BfOmpa, PrOmpA, Cp10bA, CpSpA, EfSant, LmOsp, SfET-2, Cpatox, Cpbtox, EcSta2, Ec0Stx2A, CjcdtB/C, CdtcdA/B, and the like. A statistical analysis can transform the level of the bacterial antigen antibody marker(s) into a bacterial antigen antibody marker profile. In some instances, a statistical analysis is a quartile score and the quartile score for each of the markers can be summed to generate a quartile sum score. In one aspect, a statistical process comprising a single learning statistical classifier system is applied to the data set of the bacterial antigen antibody marker profile to produce a statistically derived decision classifying a sample as an IBS sample or a non-IBS sample (e.g., healthy control sample) based upon the bacterial antigen antibody marker profile, wherein the bacterial antigen antibody marker profile indicates the level of at least one bacterial antigen antibody marker.

The term "mast cell marker score" or "mast cell score" includes the level of 1, 2, 3, 4, 5, 6, 7, 8, 9, 10, or more markers of an individual, wherein the markers can be a mast cell marker, such as, but not limited to β-tryptase, histamine, and prostaglandin E2. A statistical analysis transforms the level of the mast cell marker(s) into a mast cell marker score. In some instances, a statistical analysis is a quartile score and the quartile score for each of the markers can be summed to generate a quartile sum score. In one aspect, a statistical analysis comprises a single learning statistical classifier system is applied to the data set of the mast cell marker score to produce a statistically derived decision classifying a sample as an IBS sample or a non-IBS sample based upon the mast cell marker wherein the mast cell marker score indicates the level of at least one mast cell marker.

The term "inflammatory cell marker score," "inflammatory marker score" or "inflammatory score" includes the level of 1, 2, 3, 4, 5, 6, 7, 8, 9, 10, 11, 12, 13, 14, 15, 16, 17, 18, 19, 20 or more marker of an individual, wherein the marker can be an inflammatory cell marker, such as, but not limited CRP, ICAM, VCAM, SAA, GROα, and combinations thereof. A statistical analysis transforms the level of the inflammatory cell marker(s) into an inflammatory score. In some instances, a statistical analysis is a quartile score and the quartile score for each of the markers can be summed to generate a quartile sum score. In one aspect, a statistical analysis comprises a single learning statistical classifier system is applied to the data set of the inflammatory cell marker score to produce a statistically derived decision classifying a sample as an IBS sample or a non-IBS sample based upon the inflammatory cell marker wherein the inflammatory score indicates the level of at least one inflammatory cell marker.

The term "kynurenine marker score," "kynurenine score," or "oxidative stress score" includes the level of 1, 2, 3, 4, 5, 6, 7, 8, 9, 10, 11, 12, 13, 14, 15, 16, 17, 18, 19, 20 or more markers of an individual, wherein the markers can be a kynurenine cell marker, such as, but not limited kynurenine (K), kynurenic acid (KyA), anthranilic acid (AA), 3-hydroxykynurenine (3-HK), 3-hydroxyanthranilic acid (3-HAA), xanthurenic acid (XA), quinolinic acid (QA), tryptophan, 5-hydroxytryptophan (5-HTP), and a combination thereof. A statistical analysis transforms the level of the kynurenine marker(s) into a kynurenine score. In some instances, a statistical analysis is a quartile score and the quartile score for each of the markers can be summed to generate a quartile sum score. In one aspect, a statistical analysis comprises a single learning statistical classifier system is applied to the data set of the kynurenine marker score to produce a statistically derived decision classifying a sample as an IBS sample or a non-IBS sample based upon the kynurenine marker wherein the kynurenine score indicates the level of at least one kynurenine marker.

The term "serotonin marker score" or "serotonin score" includes the level of 1, 2, 3, 4, 5, 6, 7, 8, 9, 10, 11, 12, 13, 14, 15, 16, 17, 18, 19, 20 or more markers of an individual, wherein the markers can be a serotonin marker, such as, but not limited serotonin (5-HT) and 5-hydroxyindoleacetic acid (5-HIAA), serotonin-O-sulfate, serotonin-O-phosphate, and combinations thereof. A statistical analysis transforms the level of the serotonin marker(s) into a serotonin score. In some instances, a statistical analysis is a quartile score and the quartile score for each of the markers can be summed to generate a quartile sum score. In one aspect, a statistical analysis comprises a single learning statistical classifier system is applied to the data set of the serotonin marker score to produce a statistically derived decision classifying a sample as an IBS sample or a non-IBS sample based upon the serotonin marker wherein the serotonin score indicates the level of at least one serotonin marker.

The term "inflammatory bowel disease marker score," "inflammatory bowel disease score," "IBD marker score" or "IBD score" includes the level of 1, 2, 3, 4, 5, 6, 7, 8, 9, 10, 11, 12, 13, 14, 15, 16, 17, 18, 19, 20 or more markers of an individual, wherein the markers can be an IBD marker, such as, but not limited, an anti-neutrophil cytoplasmic antibody (ANCA), an anti-*Saccharomyces cerevisiae* immunoglobulin G (ASCA-IgA), an anti-*Saccharomyces cerevisiae* immunoglobulin G (ASCA-IgG), an anti-outer membrane protein C (anti-OmpC) antibody, an anti-flagellin antibody, a perinuclear anti-neutrophil cytoplasmic antibody (pANCA), an anti-Fla2 antibody, an anti-FlaX antibody, an anti-CBir antibody, ICAM-1, VCAM-1, VEGF, CRP, SAA, and combinations thereof. A statistical analysis transforms the level of the IBD marker(s) into an IBD score. Additional genetic markers of IBD include ATG16L1, ECM1, NKX2-3, STAT3, and SNPs thereof. In some instances, a statistical analysis is a quartile score and the quartile score for each of the markers can be summed to generate a quartile sum score. In one aspect, a statistical analysis comprises a single learning statistical classifier system is applied to the data set of the IBD marker score to produce a statistically derived decision classifying a sample as an IBD sample or a non-IBD sample based upon the IBD marker wherein the IBD score indicates the level of at least one IBD marker.

The term "bile acid malabsorption marker score," "bile acid malabsorption score" or "BAM score" includes the level of 1, 2 or more markers of an individual, wherein the markers can be a BAM marker, such as, but not limited 7-α-hydroxy-4-cholesten-3-one and FGF19. A statistical analysis transforms the level of the BAM marker(s) into a BAM score. In some instances, a statistical analysis is a quartile score and the quartile score for each of the markers can be summed to generate a quartile sum score. In one aspect, a statistical analysis comprises a single learning statistical classifier system is applied to the data set of the BAM marker score to produce a statistically derived decision classifying a sample as an IBS sample or a non-IBS sample based upon the BAM marker wherein the BAM score indicates the level of at least one BAM marker.

The term "celiac disease marker score," "celiac disease score," "CD marker score" or "CD score" includes the level of 1, 2, 3, 4, 5, 6, 7, 8, 9, 10, 11, 12, 13, 14, 15, 16, 17, 18, 19, 20 or more markers of an individual, wherein the markers can be a CD marker, such as, but not limited an anti-gliadin IgA antibody, an anti-gliadin IgG antibody, an anti-tissue transglutaminase (tTG) antibody, an anti-endomysial antibody, and combinations thereof. A statistical analysis transforms the level of the CD marker(s) into an CD score. In some instances, a statistical analysis is a quartile score and the quartile score for each of the markers can be summed to generate a quartile sum score. In one aspect, a statistical analysis comprises a single learning statistical classifier system is applied to the data set of the CD marker score to produce a statistically derived decision classifying a sample as a CD sample or a non-CD sample based upon the CD marker wherein the CD score indicates the level of at least one CD marker.

In quartile analysis, there are three numbers (values) that divide a range of data into four equal parts. The first quartile (also called the "lower quartile") is the number below which lies the 25 percent of the bottom data. The second quartile (the "median quartile") divides the range in the middle and has 50 percent of the data below it. The third quartile (also called the "upper quartile") has 75 percent of the data below it and the top 25 percent of the data above it. As a non-limiting example, quartile analysis can be applied to the concentration level of a marker such as an antibody or other protein marker described herein, such that a marker level in the first quartile (<25%) is assigned a value of 1, a marker level in the second quartile (25-50%) is assigned a value of 2, a marker level in the third quartile (51%-<75%) is assigned a value of 3, and a marker level in the fourth quartile (75%-100%) is assigned a value of 4.

As used herein, "quartile sum score" or "QSS" includes the sum of quartile scores for all of the markers of interest. As a non-limiting example, a quartile sum score for a panel of 6 markers may range from 6-24, wherein each of the individual markers is assigned a quartile score of 1-4 based upon the presence or absence of the marker, or the level of the marker.

The terms "statistical algorithm" or "statistical analysis" include a learning statistical classifier system. In some instances, the learning statistical classifier system is selected from the group consisting of a random forest, classification and regression tree, boosted tree, neural network, support vector machine, general chi-squared automatic interaction detector model, interactive tree, multiadaptive regression spline, machine learning classifier, and combinations thereof. In certain instances, the statistical algorithm comprises a single learning statistical classifier system. In other embodiments, the statistical algorithm comprises a combination of at least two learning statistical classifier systems. In some instances, the at least two learning statistical classifier systems are applied in tandem. Non-limiting examples of statistical algorithms and analysis suitable for use in the invention are described in U.S. Patent Publication No. 2011/0045476, the disclosure of which is hereby incorporated by reference in its entirety for all purposes.

The term "diagnostic model" includes a kynurenine score, mast cell score, serotonin score, bile acid malabsorption score, microbiome score, inflammatory score, and combinations thereof. In a preferred aspect, a retrospective analysis is done on a cohort of known disease outcomes with known complications and surgical procedures performed, as well as healthy controls. In one aspect, a regression analysis (e.g., logistic regression) can be performed on the level of one or more kynurenine markers, one or more mast cell markers, one or more serotonin markers, one or more bile acid malabsorption markers, one or more microbiome markers, and/or one or more inflammatory markers, to develop a diagnostic model.

III. Description of the Embodiments

A. Methods for Aiding in the Diagnosis of Irritable Bowel Syndrome

In one aspect, the present invention provides methods of aiding in the diagnosis of irritable bowel syndrome (IBS) in a subject.

Figure 5:
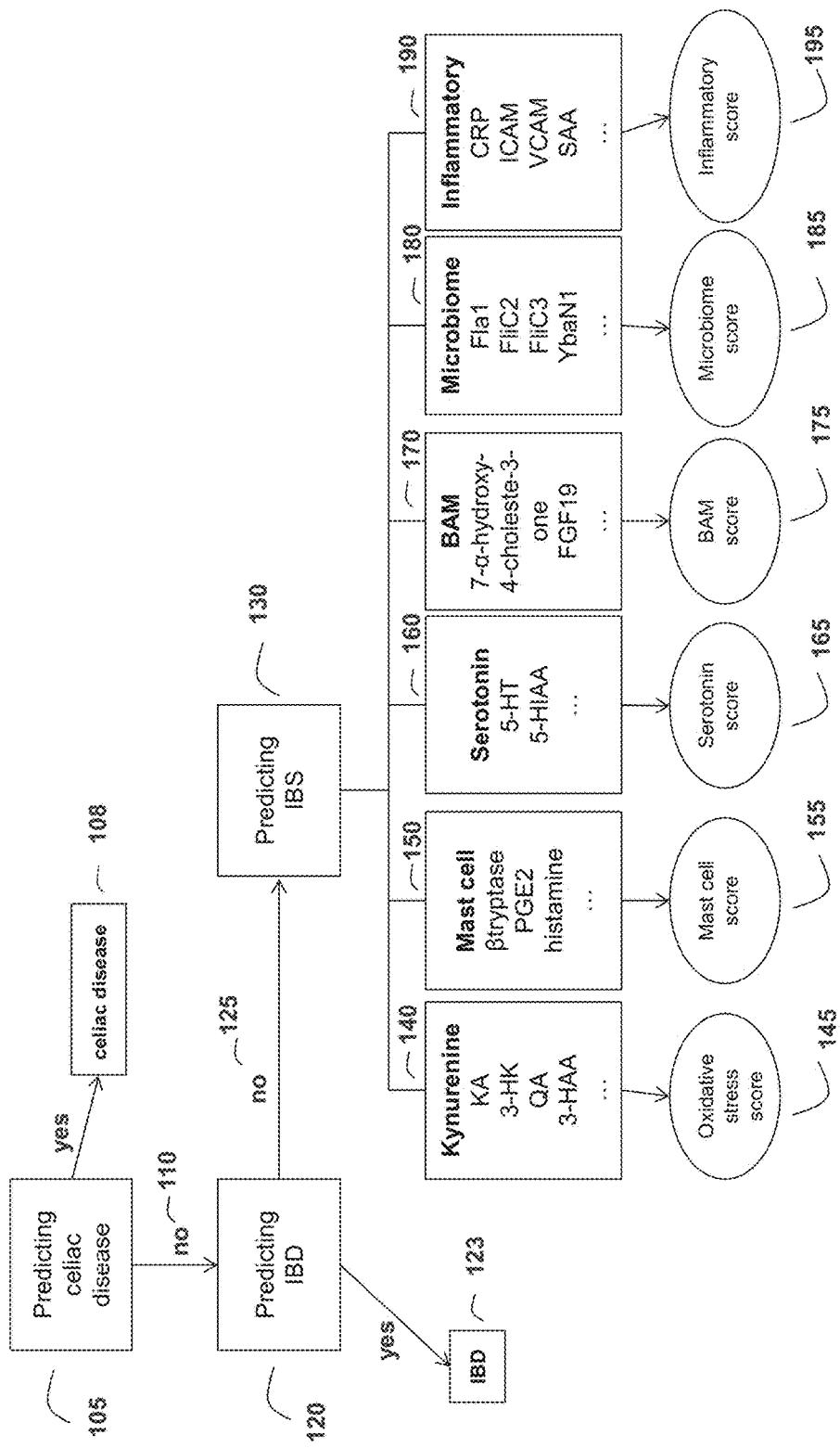
FIG. 5 illustrates an exemplary embodiment of the method of the present invention.

FIG. 5 illustrates a flowchart for an exemplary embodiment of an IBS diagnostic assay of the present invention. In certain embodiments, the diagnostic assay applies the measurements of celiac disease (CD) markers and computes a celiac disease score based on a first statistical algorithm for predicting CD vs. non-CD (105). The statistical model determines if the patient has CD. If the celiac disease score compared to a control score predicts that the patient is non-CD (110), the sample proceeds to the next step of the method. This step applies the measurements of inflammatory bowel disease (IBD) markers and computes an IBD score based on a second statistical algorithm for predicting IBD vs. non-IBD (120). If the patient's IBD score compared to a control score predicts that the patient is non-IBD (125), the sample proceeds to the next step of the assay which is used to predict IBS from non-IBS (130). This step applies the combination of the patient's microbiome score (185), mast cell score (155), inflammatory score (195), bile acid malabsorption score (175), oxidative stress score (145), and serotonin score (165) that are based on measurements of bacterial antigen antibody markers (180), mast cell markers (150), inflammatory markers (190), bile acid malabsorption markers (170), kynurenine markers (140), and serotonin markers (160), respectively, to compute a disease score for predicting IBS vs. non-IBS. If the patient's disease score is less than the cut-off, the algorithm predicts that the patient is non-IBS. If the patient's disease score is greater than the cut-off, the patient is predicted to have IBS.

In some embodiments, the method provided herein comprises: (a) measuring the level of an array of celiac disease (CD) markers in a biological sample taken from the subject; (b) applying a statistical analysis to the measured level of the array of CD markers to generate a CD score; (c) determining that the subject has CD based on the CD score compared to that of a control cohort such as patients with CD.

In some embodiments, CD marker is selected from the group consisting of an anti-gliadin IgA antibody, an anti-gliadin IgG antibody, an anti-tissue transglutaminase (tTG) antibody, an anti-endomysial antibody, and combinations thereof. In some embodiments, the statistical analysis transforms the level of the array of CD markers into an CD score. In some embodiments, the CD score includes an empirically derived profile that is based upon an analysis of a plurality of CD markers. In one aspect, the concentration of markers or their measured concentration values are transformed into an index by an algorithm resident on a computer. In certain aspects, the score is a synthetic or human derived output, profile, or cut off value(s), which expresses the biological data in numerical terms. The score can be used to determine or make or aid in making a clinical decision. In some embodiments, the statistical analysis includes applying a quartile analysis to the CD markers to about obtain a quartile sum score (QSS) for the subject by converting the presence of level of the CD markers into a quartile score, and summing the quartile score for each marker.

In some embodiments, the method comprises: (a) measuring the level of an array of inflammatory bowel disease (IBD) markers in a biological sample taken from the subject; (b) applying a statistical analysis to the measured level of the array of IBD markers to generate a IBD score; and (c) determining that the subject has IBD based on the IBD score compared to that of a control cohort such as patients with IBD.

In some embodiments, IBD marker is selected from the group consisting of an anti-neutrophil cytoplasmic antibody (ANCA), an anti-*Saccharomyces cerevisiae* immunoglobulin G (ASCA-IgA), an anti-*Saccharomyces cerevisiae* immunoglobulin G (ASCA-IgG), an anti-outer membrane protein C (anti-OmpC) antibody, an anti-flagellin antibody, a perinuclear anti-neutrophil cytoplasmic antibody (pANCA), an anti-Fla2 antibody, an anti-FlaX antibody, an anti-CBir antibody, ICAM-1, VCAM-1, VEGF, CRP, SAA, and combinations thereof. In some embodiments, the statistical analysis transforms the level of the array of IBD markers into an IBD score. In some embodiments, the IBD score includes an empirically derived profile that is based upon an analysis of a plurality of IBD markers. In one aspect, the concentration of markers or their measured concentration values are transformed into an index by an algorithm resident on a computer. In certain aspects, the score is a synthetic or human derived output, profile, or cut off value(s), which expresses the biological data in numerical terms. The score can be used to determine or make or aid in making a clinical decision. In some embodiments, the statistical analysis includes applying a quartile analysis to the IBD markers to about obtain a quartile sum score (QSS) for the subject by converting the presence of level of the IBD markers into a quartile score, and summing the quartile score for each marker.

In some embodiments, the method comprises: (a) measuring the level of an array of bacterial antigen antibody markers in a biological sample taken from the subject; and (b) applying a statistical analysis to the measured level of the array of bacterial antigen antibody markers to generate a bacterial antigen antibody marker score. In some embodiments, the bacterial antigen antibody marker is an antibody against a bacterial antigen, wherein the bacterial antigen is selected from the group consisting of Fla1, Fla2, FlaA, FliC, FliC2, FliC3, YBaN1, ECFliC, Ec0FliC, SeFljB, CjFlaA, CjFlaB, SfFliC, CjCgtA, Cjdmh, CjGT-A, EcYidX, EcEra, EcFrvX, EcGabT, EcYedK, EcYbaN, EcYhgN, RtMaga, RbCpaF, RgPilD, LaFrc, LaEno, LjEFTu, BfOmpa, PrOmpA, Cp10bA, CpSpA, EfSant, LmOsp, SfET-2, Cpatox, Cpbtox, EcSta2, Ec0Stx2A, CjcdtB/C, CdtcdA/B, and combinations thereof. In some embodiments, the statistical analysis transforms the level of the array of bacterial antigen antibody markers into a microbiome score. In some embodiments, the microbiome score includes an empirically derived profile that is based upon an analysis of a plurality of bacterial antigen antibody markers. In one aspect, the concentration of markers or their measured concentration values are transformed into an index by an algorithm resident on a computer. In certain aspects, the score is a synthetic or human derived output, profile, or cut off value(s), which expresses the biological data in numerical terms. The score can be used to determine or make or aid in making a clinical decision. In some embodiments, the statistical analysis includes applying a quartile analysis to the bacterial antigen antibody markers to about obtain a quartile sum score (QSS) for the subject by converting the presence of level of the bacterial antigen antibody markers into a quartile score, and summing the quartile score for each marker.

In some embodiments, the diagnostic model comprises a microbiome score. In some embodiments, the diagnostic model is established using a retrospective cohort with known outcomes of a clinical subtype of IBS and healthy controls. In some embodiments, the microbiome score is derived by applying logistic regression analysis to the level of one or more bacterial antigen antibody markers determined in the retrospective cohort.

In some embodiments, the method comprises: (a) measuring the level of an array of mast cell markers in a biological sample taken from the subject; and (b) applying a statistical analysis to the measured level of the array of mast cell markers to generate a mast cell marker score. In some embodiments, the mast cell marker is selected from the group consisting of β-tryptase, histamine, prostaglandin E2, and combinations thereof. In some embodiments, the statistical analysis transforms the level of the array of mast cell markers into a mast cell score. In some embodiments, the mast cell score includes an empirically derived profile that is based upon an analysis of a plurality of mast cell markers. In one aspect, the concentration of markers or their measured concentration values are transformed into an index by an algorithm resident on a computer. In certain aspects, the score is a synthetic or human derived output, profile, or cut off value(s), which expresses the biological data in numerical terms. The score can be used to determine or make or aid in making a clinical decision. A mast cell score can be measured multiple times over the course of time. In one aspect, the algorithm can be trained with known samples and thereafter validated with samples of known identity. In some embodiments, the statistical analysis includes applying a quartile analysis to the mast cell markers to about obtain a quartile sum score (QSS) for the subject by converting the presence of level of the mast cell markers into a quartile score, and summing the quartile score for each marker.

In some embodiments, the diagnostic model comprises a mast cell score. In some embodiments, the diagnostic model is established using a retrospective cohort with known outcomes of a clinical subtype of IBS and healthy controls.

In some embodiments, the mast cell score is derived by applying logistic regression analysis to the level of one or more mast cell markers determined in the retrospective cohort.

In some embodiments, the method comprises: (a) measuring the level of an array of inflammatory markers in a biological sample taken from the subject; and (b) applying a statistical analysis to the measured level of the array of inflammatory markers to generate a inflammatory score. In some embodiments, inflammatory marker is selected from the group consisting of BDNF, EGF, VEGF, amphiregulin, NGAL, TWEAK, GRO-α, IL-1β, IL-8, TIMP1, CRP, SAA, ICAM-1, VCAM-1, and combinations thereof. In some embodiments, the statistical analysis transforms the level of the array of inflammatory markers into an inflammatory score. In some embodiments, the inflammatory score includes an empirically derived profile that is based upon an analysis of a plurality of inflammatory markers. In one aspect, the concentration of markers or their measured concentration values are transformed into an index by an algorithm resident on a computer. In certain aspects, the score is a synthetic or human derived output, profile, or cut off value(s), which expresses the biological data in numerical terms. The score can be used to determine or make or aid in making a clinical decision. An inflammatory score can be measured multiple times over the course of time. In one aspect, the algorithm can be trained with known samples and thereafter validated with samples of known identity. In some embodiments, the statistical analysis includes applying a quartile analysis to the inflammatory markers to about obtain a quartile sum score (QSS) for the subject by converting the presence of level of the inflammatory markers into a quartile score, and summing the quartile score for each marker.

In some embodiments, the diagnostic model comprises an inflammatory score. In some embodiments, the diagnostic model is established using a retrospective cohort with known outcomes of a clinical subtype of IBS and healthy controls. In some embodiments, the inflammatory score is derived by applying logistic regression analysis to the level of one or more inflammatory markers determined in the retrospective cohort.

In some embodiments, the method comprises: (a) measuring the level of an array of kynurenine markers in a biological sample taken from the subject; and (b) applying a statistical analysis to the measured level of the array of kynurenine markers to generate a kynurenine score (e.g., oxidative stress score). In some embodiments, kynurenine marker is selected from the group consisting of kynurenine (K), kynurenic acid (KyA), anthranilic acid (AA), 3-hydroxykynurenine (3-HK), 3-hydroxyanthranilic acid (3-HAA), xanthurenic acid (XA), quinolinic acid (QA), tryptophan, 5-hydroxytryptophan (5-HTP), and combinations thereof. In some embodiments, the statistical analysis transforms the level of the array of kynurenine markers into a kynurenine score. In some embodiments, the kynurenine score includes an empirically derived profile that is based upon an analysis of a plurality of kynurenine markers. In one aspect, the concentration of markers or their measured concentration values are transformed into an index by an algorithm resident on a computer. In certain aspects, the score is a synthetic or human derived output, profile, or cut off value(s), which expresses the biological data in numerical terms. The score can be used to determine or make or aid in making a clinical decision. A kynurenine score can be measured multiple times over the course of time. In one aspect, the algorithm can be trained with known samples and thereafter validated with samples of known identity. In some embodiments, the statistical analysis includes applying a quartile analysis to the kynurenine markers to about obtain a quartile sum score (QSS) for the subject by converting the presence of level of the kynurenine markers into a quartile score, and summing the quartile score for each marker.

In some embodiments, the diagnostic model comprises a kynurenine score. In some embodiments, the diagnostic model is established using a retrospective cohort with known outcomes of a clinical subtype of IBS and healthy controls. In some embodiments, the kynurenine score is derived by applying logistic regression analysis to the level of one or more kynurenine markers determined in the retrospective cohort.

In some embodiments, the method comprises: (a) measuring the level of an array of serotonin markers in a biological sample taken from the subject; and (b) applying a statistical analysis to the measured level of the array of serotonin markers to generate a serotonin score. In some embodiments, serotonin marker is selected from the group consisting of serotonin (5-HT), 5-hydroxyindoleacetic acid (5-HIAA), serotonin-O-sulfate, serotonin-O-phosphate and combinations thereof. In some embodiments, the statistical analysis transforms the level of the array of serotonin markers into a serotonin score. In some embodiments, the serotonin score includes an empirically derived profile that is based upon an analysis of a plurality of serotonin markers. In one aspect, the concentration of markers or their measured concentration values are transformed into an index by an algorithm resident on a computer. In certain aspects, the score is a synthetic or human derived output, profile, or cut off value(s), which expresses the biological data in numerical terms. The score can be used to determine or make or aid in making a clinical decision. A serotonin score can be measured multiple times over the course of time. In one aspect, the algorithm can be trained with known samples and thereafter validated with samples of known identity. In some embodiments, the statistical analysis includes applying a quartile analysis to the serotonin markers to about obtain a quartile sum score (QSS) for the subject by converting the presence of level of the serotonin markers into a quartile score, and summing the quartile score for each marker.

In some embodiments, the diagnostic model comprises a serotonin score. In some embodiments, the diagnostic model is established using a retrospective cohort with known outcomes of a clinical subtype of IBS and healthy controls. In some embodiments, the serotonin score is derived by applying logistic regression analysis to the level of one or more serotonin markers determined in the retrospective cohort.

In some embodiments, the method comprises: (a) measuring the level of an array of bile acid malabsorption (BAM) markers in a biological sample taken from the subject; and (b) applying a statistical analysis to the measured level of the array of BAM markers to generate a BAM score. In some embodiments, BAM marker is selected from the group consisting of 7α-hydroxy-4-cholesten-3-one, FGF19, and combinations thereof. In some embodiments, the statistical analysis transforms the level of the array of BAM markers into a serotonin score. In some embodiments, the BAM score includes an empirically derived profile that is based upon an analysis of a plurality of BAM markers. In one aspect, the concentration of markers or their measured concentration values are transformed into an index by an algorithm resident on a computer. In certain aspects, the score is a synthetic or human derived output, profile, or cut off value(s), which expresses the biological data in numerical terms. The score can be used to determine or make or aid in making a clinical decision. A BAM score can be measured multiple times over the course of time. In one aspect, the algorithm can be trained with known samples and thereafter validated with samples of known identity. In some embodiments, the statistical analysis includes applying a quartile analysis to the BAM markers to about obtain a quartile sum score (QSS) for the subject by converting the presence of level of the BAM markers into a quartile score, and summing the quartile score for each marker.

In some embodiments, the diagnostic model comprises a BAM score. In some embodiments, the diagnostic model is established using a retrospective cohort with known outcomes of a clinical subtype of IBS and healthy controls. In some embodiments, the BAM score is derived by applying logistic regression analysis to the level of one or more BAM markers determined in the retrospective cohort.

In some embodiments, a disease score is generated for the subject by using an algorithm that integrates the subject's microbiome score, mast cell score, inflammatory score, BAM score, kynurenine score and serotonin score. The subject's disease score can be compared to a diagnostic model to determine whether the subject has an increased likelihood of having IBS compared to being a healthy control.

In some embodiments, the diagnostic model is based on a combination of the microbiome score, mast cell score, inflammatory score, bile acid malabsorption score, kynurenine score, and serotonin score from a retrospective cohort of patients with known IBS outcomes and healthy controls. For instance, the diagnostic model can represent the disease scores for a retrospective cohort of patients with known IBS outcomes and healthy controls. In some embodiments, the diagnostic model comprises a logistic regression model.

In some embodiments, the diagnostic model comprises a IBS diagnostic cut-off value wherein a disease score that is higher than the cut-off value indicates that the subject has IBS and/or a subtype of IBS. In other instances, a disease score that is lower than the cut-off value can indicate that the subject does not have IBS.

The sample used for detecting or determining the level of at least one biomarker is typically whole blood, plasma, serum, saliva, urine, stool (i.e., feces), tears, and any other bodily fluid, or a tissue sample (i.e., biopsy) such as a small intestine or colon sample. Preferably, the sample is serum, whole blood, plasma, stool, urine, or a tissue biopsy. In certain instances, the methods of the present invention further comprise obtaining the sample from the individual prior to detecting or determining the level of at least one biomarker in the sample. In a preferred embodiment, the additional biomarker is detected from a blood or serum sample. In other embodiments, the biomarker is detected from a saliva sample, a urine sample, a stool sample or a biopsy from the bowel of the subject.

B. Bacterial Antigen Antibody Markers (e.g., Microbiome Markers)

As used herein, the term "bacterial antigen antibody" refers to an antibody that specifically binds to a bacterial antigen or an antigenic fragment thereof, such as an antibacterial antigen antibody. Without being bound to any particular theory, individuals with IBS or other disorders involving the gastrointestinal microbiota can develop antibacterial antigen antibodies.

In one aspect, the present invention provides methods for aiding in the diagnosis of IBS and/or subtypes of IBS by detecting the level of at least one bacterial antigen antibody marker in a sample. The bacterial antigen antibody marker includes antibodies that specifically bind to a bacterial antigen including, but not limited to, Fla1, Fla2, FlaA, FliC, FliC2, FliC3, YBaN1, ECFliC, Ec0FliC, SeFljB, CjFlaA, CjFlaB, SfFliC, CjCgtA, Cjdmh, CjGT-A, EcYidX, EcEra, EcFrvX, EcGabT, EcYedK, EcYbaN, EcYhgN, RtMaga, RbCpaF, RgPilD, LaFrc, LaEno, LjEFTu, BfOmpa, PrOmpA, Cp10bA, CpSpA, EfSant, LmOsp, SfET-2, Cpatox, Cpbtox, EcSta2, Ec0Stx2A, CjcdtB/C, CdtcdA/B, and a combination thereof.

In some embodiments, the method comprises measuring the level of at least one bacterial antigen antibody markers in a biological sample taken from the subject. In some instance, any 1-tuple, 2-tuple, 3-tuple, 4-tuple, 5-tuple, 6-tuple, 7-tuple, 8-tuple, 9-tuple, 10-tuple, 11-tuple, 12-tuple, 13-tuple, 15-tuple 16-tuple, 17-tuple, 18-tuple, 19-tuple, 20-tuple, 21-tuple, 22-tuple, 23-tuple, 24-tuple, 25-tuple, 26-tuple, 27-tuple, 28-tuple, 29-tuple, 30-tuple, 31-tuple, 32-tuple, 33-tuple, 34-tuple or 35-tuple for the bacterial antigen antibodies can be measured.

In some embodiments, the level of at least one bacterial antigen antibody marker, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 or more bacterial antigen antibody markers are increased in an individual with IBS compared to a healthy control. In other embodiments, the level of at least one bacterial antigen antibody marker, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 or more bacterial antigen antibody markers are decreased in an individual with IBS compared to a healthy control. In some embodiments, the level of an array of bacterial antigen antibody markers is dysregulated in a sample taken from an individual with IBS compared to one from a healthy control.

In some embodiments, the method comprises: a) contacting a biological sample from the subject with a bacterial antigen polypeptide or an antigenic fragment thereof under conditions suitable to transform the bacterial antigen antibody present in the sample into a complex comprising the bacterial antigen antibody and the bacterial antigen polypeptide or fragment thereof; and (b) determining the level of the complex, thereby determining the level of the bacterial antigen present in the sample. In some embodiments, the method further comprises: (c) comparing the level of the bacterial antigen antibody present in the sample to a control level of the bacterial antigen antibody, wherein the level of the bacterial antigen antibody is indicative of an increased likelihood of the subject having IBS.

The bacterial antigen polypeptide or fragment thereof selectively binds to the bacterial antigen antibody to be measured. For example, the level of an antibody against bacteria flagellin (e.g., SfFliC) can be measured using the flagellin polypeptide or an antigenic fragment thereof.

In a specific embodiment, the invention provides a method to aid in the diagnosis of IBS, the method comprises: (a) contacting a sample having a bacterial antigen antibody contained therein under conditions suitable to transform the bacterial antigen antibody into a complex comprising the bacterial antigen and the captured anti-bacterial antigen antibody; (b) contacting the complex with an enzyme labeled indicator antibody to transform the complex into a labeled complex; (c) contacting the labeled complex with a substrate for the enzyme; and (d) detecting the presence or level of the bacterial antigen antibody in the sample.

In certain other embodiments, the level of at least one bacterial antigen antibody marker is determined using an immunoassay (e.g., ELISA) or an immunohistochemical assay. A non-limiting example of an immunoassay suitable for use in the methods of the present invention includes an enzyme-linked immunosorbent assay (ELISA). Examples of immunohistochemical assays suitable for use in the methods of the present invention include, but are not limited to, immunofluorescence assays such as direct fluorescent antibody assays, indirect fluorescent antibody (IFA) assays, anticomplement immunofluorescence assays, and avidin-biotin immunofluorescence assays. Other types of immunohistochemical assays include immunoperoxidase assays. Suitable ELISA kits for determining the presence of level of a bacterial antigen in a serum, plasma, saliva, or urine sample, are available from e.g., Antigenix America Inc. (Huntington station, NY), Promega (Madison, Wis.), R&D Systems, Inc. (Minneapolis, Minn.), Life Technologies (Carlsbad, Calif.), CHEMICON International, Inc. (Temecula, Calif.), Neogen Corp. (Lexington, Ky.), PeproTech (Rocky Hill, N.J.), Alpco Diagnostics (Salem, N.H.), Pierce Biotechnology, Inc. (Rockford, Ill.), and/or Abazyme (Needham, Mass.).

In one aspect, the present invention provides an assay for the detection of a bacterial antigen antibody marker in a sample, the method comprising the steps of: (a) coating a solid phase surface with a bacterial antigen or antigenic fragment thereof; (b) contacting the solid phase surface with a sample under conditions suitable to transform the bacterial antigen antibody present in the sample into a complex comprising the bacterial antigen and the bacterial antigen antibody; (c) contacting the bacterial antigen and the bacterial antigen antibody with a detecting antibody under conditions suitable to form a ternary complex; and (d) contacting the ternary complex with a luminescent or chemiluminescent substrate.

In one embodiment, the detecting antibody is conjugated to alkaline phosphatase. In other embodiments, the detecting antibody is not conjugated to an enzyme and the method further comprises the steps of (i) contacting the ternary complex with a third antibody conjugated to alkaline phosphatase under conditions suitable to form a quaternary complex and (ii) contacting the quaternary complex with a luminescent or chemiluminescent substrate.

Any suitable antibody pair may be used for the capture and detecting antibodies in a sandwich ELISA. One of skill in the art will know and appreciate how to select an appropriate antibody pair for the assay. Generally, two antibodies are selected that bind to the target of interest, e.g., β-tryptase, at different epitopes such that the binding of the first (capture) antibody does not interfere with the second (detecting) antibody. In certain embodiments, the detecting antibody will be conjugated to an enzyme, for example, alkaline phosphatase, to aid in the detection of the complex. In other embodiments, a secondary antibody conjugated to an enzyme (e.g., alkaline phosphatase), which binds to the detecting antibody, may be used in the assay.

Generally, the complex will be detected by the use of a luminescent substrate, for example, a luminescent substrate found in a kit such as Ultra LITE (NAG Research Laboratories); SensoLyte (AnaSpec); SuperSignal ELISA Femto Maximum Sensitivity Substrate (Thermo Scientific); SuperSignal ELISA Pico Chemiluminescent Substrate (Thermo Scientific); or CPSD (disodium 3-(4-methoxyspiro{1,2-dioxetane-3,2'-(5'-chloro)tricyclo[3.3.1.13,7]decan}-4-yl) phenyl phosphate; Tropix, Inc).

The amino acid sequence of an antigenic fragment of a bacterial antigen can be identified by predicting the immunogenic sites in silico using software algorithms such as EMBOSS. For instance, the hydrophilicity, accessibility and flexibility properties of a series of peptide fragments of an antigen protein are accessed to determine the peptide fragments that are predicted to be the most antigenic (e.g., have the highest antigenic score).

In certain embodiments, a variety of bacterial antigens are particularly useful in the methods of the present invention for aiding in the diagnosis of IBS. Non-limiting examples of bacterial antigens include flagellin polypeptides or fragments thereof, and other polypeptides or fragments thereof that are expressed by the gastrointestinal microbiota. Microbial flagellin is a protein found in bacterial flagellum that arrange itself in a hollow cylinder to form the filament. Flagellin polypeptides or fragments thereof are typically expressed by bacteria including *Clostridium, Lachnospiraceae bacterium* A4, *E. coli* K12, *E. coli* O157:H7, *Shigella flexneri, Campylobacter jejuni,* and *Salmonella enteritidis*.

The presence of anti-flagellin antibody in a sample from an individual can be determined using a flagellin protein or a fragment thereof such as an immunoreactive fragment thereof. Suitable flagellin antigens useful in determining anti-flagellin antibody levels in a sample include, without limitation, a flagellin protein such as CBir-1, FliC, FljB, flagellin, flagellin X (Fla-X), flagellin A (FlaA), flagellin B (FlaB), flagellin 2 (Fla2), fragments thereof, and combinations thereof, a flagellin polypeptide having substantially the same amino acid sequence as the flagellin protein, or a fragment thereof such as an immunoreactive fragment thereof. As used herein, a flagellin polypeptide generally describes polypeptides having an amino acid sequence with greater than about 50% identity, preferably greater than about 60% identity, more preferably greater than about 70% identity, still more preferably greater than about 80%, 85%, 90%, 95%, 96%, 97%, 98%, or 99% amino acid sequence identity with a naturally-occurring flagellin protein, with the amino acid identity determined using a sequence alignment program such as CLUSTALW. Such flagellin antigens can be prepared, e.g., by purification from bacterium such as *Helicobacter Bilis, Helicobacter mustelae, Helicobacter pylori, Lachnospiraceae bacterium* A4, *Shigella flexneri, Escherichia coli, Salmonella enteritidis, Campylobacter jejuni, Butyrivibrio fibrisolvens*, and bacterium found in the cecum, by recombinant expression of a nucleic acid encoding a flagellin antigen, by synthetic means such as solution or solid phase peptide synthesis.

Non-limiting examples of bacterial antigens are presented in Table 1.

TABLE 1

Bacteria antigens

| Antigen | Grouping | Phyla | Strain | UniProt |
| --- | --- | --- | --- | --- |
| EcFliC | Infectious | Proteobacteria | *E. coli* | P04949 |
| EcOFliC | Infectious | Proteobacteria | *E. coli* H7:O157 | Q7AD06 |
| SeFljB | Infectious | Proteobacteria | *S. enterotidis* | B5R0Z9 |
| CjFlaA | Infectious | Proteobacteria | *C. jejuni* | Q2M5R2 |
| CjFlaB | Infectious | Proteobacteria | *C. jejuni* | A1W0V5 |
| SfFliC | Infectious | Proteobacteria | *S. flexneri* | Q08860 |
| CjCgtA | Infectious | Proteobacteria | *C. jejuni* | Q50FZ3 |
| Cjdmh | Infectious | Proteobacteria | *C. jejuni* | Q50FQ7 |
| CjGT-A | Infectious | Proteobacteria | *C. jejuni* | Q50FX0 |
| EcYidX | Commensal | Proteobacteria | *E. coli* | P0ADM6 |
| EcEra | Commensal | Proteobacteria | *E. coli* | U6NG20 |
| EcFrvX | Commensal | Proteobacteria | *E. coli* | P32153 |
| EcGabT | Commensal | Proteobacteria | *E. coli* | P22256 |
| EcYedK | Commensal | Proteobacteria | *E. coli* | P76318 |
| EcYbaN | Commensal | Proteobacteria | *E. coli* | P0AAR5 |
| EcYhgN | Commensal | Proteobacteria | *E. coli* | P67143 |
| RtMaga | Mucin-degr. | Firmicutes | *R. torques* | D4M4S6 |
| RbCpaF | Mucin-degr. | Firmicutes | *R. bromii* | D4L5L7 |
| RgPilD | Mucin-degr. | Firmicutes | *R. gnavus* | A7B5T4 |
| LaFrc | Commensal | Firmicutes | *L. acidophilus* | R4JZC5 |
| LaEno | Commensal | Firmicutes | *L. acidophilus* | Q5FKM6 |
| LjEFTu | Commensal | Firmicutes | *L. johnsonii* | Q74JU6 |
| BfOmpA | Commensal | Bacteriodetes | *B. fragilis* | Q64VP7 |
| PrOmpA | Commensal | Bacteriodetes | *Prevotella* spp. | C9PT48 |
| Cp10bA | Commensal | Firmicutes | *C. perfringens* | B1V1I2 |
| CpSpA | Commensal | Firmicutes | *C. perfringens* | Q5DWA9 |
| EfSant | Commensal | Firmicutes | *E. faecalis* | C7W575 |
| LmOsp | Commensal | Firmicutes | *L. monocytogenes* | B8DFK3 |
| SfET-2 | Toxins | Proteobacteria | *S. flexneri* | Q7BEN0 |
| Cpatox | Toxins | Firmicutes | *C. perfringens* | Q3HR45 |
| Cpbtox | Toxins | Firmicutes | *C. perfringens* | B1R976 |
| EcSta2 | Toxins | Proteobacteria | *E. coli* | Q2WE95 |
| Ec0Stx2A | Toxins | Proteobacteria | *E. coli* H7:0157 | B6ZXF5 |
| CjcdtB/C | Toxins | Proteobacteria | *C. jejuni* | Q46101/ Q46102 |
| CdtcdA/B | Toxins | Firmicutes | *C. difficile* | P16154/ P18177 |

The term "EcFliC" refers to a flagellin of *Escherichia coli* strain K12 that is immunoreactive with an anti-FliC antibody. Suitable EcFliC antigens useful in determining anti-FliC antibody levels in a sample include, without limitation, a FliC protein of *Escherichia coli* strain K12, a FliC polypeptide having substantially the same amino acid sequence as the FliC protein of *Escherichia coli* strain K12, or a fragment thereof such as an immunoreactive fragment thereof. A FliC polypeptide of *Escherichia coli* strain K12 generally describes polypeptides having an amino acid sequence with greater than about 50% identity, preferably greater than about 60% identity, more preferably greater than about 70% identity, still more preferably greater than about 80%, 85%, 90%, 95%, 96%, 97%, 98%, or 99% amino acid sequence identity with a FliC protein of *Escherichia coli* strain K12, with the amino acid identity determined using a sequence alignment program such as CLUSTALW. Such antigens can be prepared, for example, by purification from enteric bacteria such as *E. coli*, by recombinant expression of a nucleic acid encoding a FliC peptide such as NCBI Accession No. AAA23950.1, by synthetic means such as solution or solid phase peptide synthesis.

The term "EcOFliC" refers to a flagellin of *Escherichia coli* strain O157:H7 that is immunoreactive with an anti-FliC antibody. Suitable FliC antigens useful in determining anti-FliC antibody levels in a sample include, without limitation, a FliC protein, a FliC polypeptide having substantially the same amino acid sequence as the FliC protein, or a fragment thereof such as an immunoreactive fragment thereof. A FliC polypeptide generally describes polypeptides having an amino acid sequence with greater than about 50% identity, preferably greater than about 60% identity, more preferably greater than about 70% identity, still more preferably greater than about 80%, 85%, 90%, 95%, 96%, 97%, 98%, or 99% amino acid sequence identity with a FliC protein, with the amino acid identity determined using a sequence alignment program such as CLUSTALW. Such antigens can be prepared, for example, by purification from enteric bacteria such as *E. coli* strain O157:H7, by recombinant expression of a nucleic acid encoding a FliC peptide such as NCBI Accession No. BAB36085.1, by synthetic means such as solution or solid phase peptide synthesis.

The term "SeFljB" refers to a flagellin protein of *Salmonella enteritidis* that is immunoreactive with an anti-Fljb antibody. Suitable SeFljB antigens useful in determining anti-Fljb antibody levels in a sample include, without limitation, a Fljb protein, a Fljb polypeptide having substantially the same amino acid sequence as the Fljb protein, or a fragment thereof such as an immunoreactive fragment thereof. A Fljb polypeptide generally describes polypeptides having an amino acid sequence with greater than about 50% identity, preferably greater than about 60% identity, more preferably greater than about 70% identity, still more preferably greater than about 80%, 85%, 90%, 95%, 96%, 97%, 98%, or 99% amino acid sequence identity with a Fljb protein, with the amino acid identity determined using a sequence alignment program such as CLUSTALW. Such antigens can be prepared, for example, by purification from enteric bacteria such as *S. enteritidis*, by recombinant expression of a nucleic acid encoding a Fljb peptide such as Uniprot No. B5R0Z9, by synthetic means such as solution or solid phase peptide synthesis.

The term "CjFlaA" refers to a flagellin subunit of the *Campylobacter jejuni* that is immunoreactive with an anti-FlaA antibody. Suitable CjFlaA antigens useful in determining anti-FlaA antibody levels in a sample include, without limitation, a FlaA protein, a FlaA polypeptide having substantially the same amino acid sequence as the FlaA protein, or a fragment thereof such as an immunoreactive fragment thereof. A FlaA polypeptide generally describes polypeptides having an amino acid sequence with greater than about 50% identity, preferably greater than about 60% identity, more preferably greater than about 70% identity, still more preferably greater than about 80%, 85%, 90%, 95%, 96%, 97%, 98%, or 99% amino acid sequence identity with a FlaA protein, with the amino acid identity determined using a sequence alignment program such as CLUSTALW. Such antigens can be prepared, for example, by purification from enteric bacteria such as *Campylobacter jejuni*, by recombinant expression of a nucleic acid encoding a FlaA peptide such as NCBI Accession No. ABC69276.1, by synthetic means such as solution or solid phase peptide synthesis.

The term "CjFlaB" refers to a flagellin B of the *Campylobacter jejuni* that is immunoreactive with an anti-FlaB antibody. Suitable CjFlaB antigens useful in determining anti-FlaB antibody levels in a sample include, without limitation, a FlaB protein, a FlaB polypeptide having substantially the same amino acid sequence as the FlaB protein, or a fragment thereof such as an immunoreactive fragment thereof. A FlaB polypeptide generally describes polypeptides having an amino acid sequence with greater than about 50% identity, preferably greater than about 60% identity, more preferably greater than about 70% identity, still more preferably greater than about 80%, 85%, 90%, 95%, 96%, 97%, 98%, or 99% amino acid sequence identity with a FlaB protein, with the amino acid identity determined using a sequence alignment program such as CLUSTALW. Such antigens can be prepared, for example, by purification from enteric bacteria such as *Campylobacter jejuni*, by recombinant expression of a nucleic acid encoding a FlaB peptide such as NCBI Accession EAQ72883.1, by synthetic means such as solution or solid phase peptide synthesis.

The term "SfFliC" refers to a flagellin of *Shigella flexneri* that is immunoreactive with an anti-FliC antibody. Suitable SfFliC antigens useful in determining anti-FliC antibody levels in a sample include, without limitation, a FliC protein, a FliC polypeptide having substantially the same amino acid sequence as the FliC protein, or a fragment thereof such as an immunoreactive fragment thereof. A FliC polypeptide generally describes polypeptides having an amino acid sequence with greater than about 50% identity, preferably greater than about 60% identity, more preferably greater than about 70% identity, still more preferably greater than about 80%, 85%, 90%, 95%, 96%, 97%, 98%, or 99% amino acid sequence identity with a FliC protein, with the amino acid identity determined using a sequence alignment program such as CLUSTALW. Such antigens can be prepared, for example, by purification from enteric bacteria such as *Shigella flexneri*, by recombinant expression of a nucleic acid encoding a FliC peptide such as NCBI Accession No. BAA04093.1, by synthetic means such as solution or solid phase peptide synthesis. One skilled in the art will appreciate that *Shigella flexneri* FliC is also known as flagellar filament structural protein, flagellin, and H-antigen.

The term "Cj81-045" or "CjGT-A" refers to a *Campylobacter jejuni* membrane protein that is immunoreactive with an anti-Cj81-045 (CjGT-A) antibody. Suitable Cj81-045 (CjGT-A) antigens useful in determining anti-Cj81-045 (-CjGT-A) antibody levels in a sample include, without limitation, a Cj81-045 (CjGT-A) protein, a Cj81-045 (CjGT-A)polypeptide having substantially the same amino acid sequence as the Cj81-045 (CjGT-A) protein, or a fragment thereof such as an immunoreactive fragment thereof. A Cj81-045 (CjGT-A) polypeptide generally describes polypeptides having an amino acid sequence with greater than about 50% identity, preferably greater than about 60% identity, more preferably greater than about 70% identity, still more preferably greater than about 80%, 85%, 90%, 95%, 96%, 97%, 98%, or 99% amino acid sequence identity with a Cj81-045 (CjGT-A) protein, with the amino acid identity determined using a sequence alignment program such as CLUSTALW. Such antigens can be prepared, for example, by purification from enteric bacteria such as *Campylobacter jejuni*, by recombinant expression of a nucleic acid encoding a Cj81-045 (CjGT-A) peptide such as NCBI Accession AAW56124.1, by synthetic means such as solution or solid phase peptide synthesis.

The term "Cj81-128" or "Cjdmh" refers to a *Campylobacter jejuni* membrane protein that is immunoreactive with an anti-Cj81-128 (-Cjdmh) antibody. Suitable Cj81-128 (Cjdmh) antigens useful in determining anti-Cj81-128 (-Cjdmh) antibody levels in a sample include, without limitation, a Cj81-128 (Cjdmh) protein, a Cj81-128 (Cjdmh) polypeptide having substantially the same amino acid sequence as the Cj81-128 (Cjdmh) protein, or a fragment thereof such as an immunoreactive fragment thereof. A Cj81-128 (Cjdmh) polypeptide generally describes polypeptides having an amino acid sequence with greater than about 50% identity, preferably greater than about 60% identity, more preferably greater than about 70% identity, still more preferably greater than about 80%, 85%, 90%, 95%, 96%, 97%, 98%, or 99% amino acid sequence identity with a Cj81-128 (Cjdmh) protein, with the amino acid identity determined using a sequence alignment program such as CLUSTALW. Such antigens can be prepared, for example, by purification from enteric bacteria such as *Campylobacter jejuni*, by recombinant expression of a nucleic acid encoding a Cj81-128 (Cjdmh) peptide such as NCBI Accession AAW56187.1, by synthetic means such as solution or solid phase peptide synthesis.

The term "Cj81-008" or "CjCgtA" refers to a beta-1,4-N-acetylgalactosaminyltransferase of *Campylobacter jejuni* that is immunoreactive with an anti-Cj81-008 (-CjCgtA) antibody. Suitable Cj81-008 (CjCgtA) antigens useful in determining anti-Cj81-008 (-CjCgtA) antibody levels in a sample include, without limitation, a Cj81-008 (CjCgtA)

protein, a Cj81-008 (CjCgtA) polypeptide having substantially the same amino acid sequence as the Cj81-008 (CjCgtA) protein, or a fragment thereof such as an immunoreactive fragment thereof. A Cj81-008 (CjCgtA) polypeptide generally describes polypeptides having an amino acid sequence with greater than about 50% identity, preferably greater than about 60% identity, more preferably greater than about 70% identity, still more preferably greater than about 80%, 85%, 90%, 95%, 96%, 97%, 98%, or 99% amino acid sequence identity with a Cj81-008 (CjCgtA) protein, with the amino acid identity determined using a sequence alignment program such as CLUSTALW. Such antigens can be prepared, for example, by purification from enteric bacteria such as *Campylobacter jejuni*, by recombinant expression of a nucleic acid encoding a Cj81-008 (CjCgtA) peptide such as NCBI Accession AAW56101.1, by synthetic means such as solution or solid phase peptide synthesis.

The term "EcYidX" refers to a putative replicase of the *Escherichia coli* strain K12 that is immunoreactive with an anti-YidX antibody. YidX is predicted to be a lipoprotein C. Suitable YidX antigens useful in determining anti-YidX antibody levels in a sample include, without limitation, a YidX protein of the *E. coli* strain K12, a YidX polypeptide having substantially the same amino acid sequence as the YidX protein, or a fragment thereof such as an immunoreactive fragment thereof. A YidX polypeptide generally describes polypeptides having an amino acid sequence with greater than about 50% identity, preferably greater than about 60% identity, more preferably greater than about 70% identity, still more preferably greater than about 80%, 85%, 90%, 95%, 96%, 97%, 98%, or 99% amino acid sequence identity with a YidX protein of the *E. coli* strain K12, with the amino acid identity determined using a sequence alignment program such as CLUSTALW. Such antigens can be prepared, for example, by purification from enteric bacteria such as *E. coli*, by recombinant expression of a nucleic acid encoding a YidX peptide such as NCBI Accession No. AAT48200.1, by synthetic means such as solution or solid phase peptide synthesis. One skilled in the art will appreciate that YidX is also known as predicted lipoprotein C.

The term "EcEra" refers to a Ras-like membrane-associated, ribosome-binding GTPase of the *Escherichia coli* strain K12 that is immunoreactive with an anti-Era antibody. Suitable EcEra antigens useful in determining anti-Era antibody levels in a sample include, without limitation, an Era protein of the *Escherichia coli* strain K12, an Era polypeptide having substantially the same amino acid sequence as the Era protein of the *E. coli* strain K12, or a fragment thereof such as an immunoreactive fragment thereof. An Era polypeptide of the *E. coli* strain K12 generally describes polypeptides having an amino acid sequence with greater than about 50% identity, preferably greater than about 60% identity, more preferably greater than about 70% identity, still more preferably greater than about 80%, 85%, 90%, 95%, 96%, 97%, 98%, or 99% amino acid sequence identity with an Era protein of the *E. coli* strain K12, with the amino acid identity determined using a sequence alignment program such as CLUSTALW. Such antigens can be prepared, for example, by purification from enteric bacteria such as *E. coli* strain K12, by recombinant expression of a nucleic acid encoding an Era peptide such as NCBI Accession No. AAA03242.1, by synthetic means such as solution or solid phase peptide synthesis. One skilled in the art will appreciate that Era is also known as membrane-associated 16S rRNA-binding GTPase, B2566, SdgE and RbaA.

The term "EcFrvX" refers to a fry operon protein of the *Escherichia coli* strain K12 that is immunoreactive with an anti-FrvX antibody. FrvX is predicted to be an endo-1,4-beta-glucanase. Suitable EcFrvX antigens useful in determining anti-FrvX antibody levels in a sample include, without limitation, a FrvX protein of the *E. coli* strain K12, a FrvX polypeptide having substantially the same amino acid sequence as the FrvX protein of the *E. coli* strain K12, or a fragment thereof such as an immunoreactive fragment thereof. A FrvX polypeptide of the *E. coli* train K12 generally describes polypeptides having an amino acid sequence with greater than about 50% identity, preferably greater than about 60% identity, more preferably greater than about 70% identity, still more preferably greater than about 80%, 85%, 90%, 95%, 96%, 97%, 98%, or 99% amino acid sequence identity with a FrvX protein of the *E. coli* strain K12, with the amino acid identity determined using a sequence alignment program such as CLUSTALW. Such antigens can be prepared, for example, by purification from enteric bacteria such as *E. coli*, by recombinant expression of a nucleic acid encoding a FrvX peptide such as NCBI Accession No. AAB03031.1, by synthetic means such as solution or solid phase peptide synthesis.

The term "EcGabT" refers to a PLP-dependent 4-aminobutyrate aminotransferase of the *Escherichia coli* strain K12 that is immunoreactive with an anti-GabT antibody. Suitable EcGabT antigens useful in determining anti-GabT antibody levels in a sample include, without limitation, a GabT protein of the *E. coli* strain K12, a GabT polypeptide having substantially the same amino acid sequence as the GabT protein of the *Escherichia coli* strain K12, or a fragment thereof such as an immunoreactive fragment thereof. A GabT polypeptide generally describes polypeptides having an amino acid sequence with greater than about 50% identity, preferably greater than about 60% identity, more preferably greater than about 70% identity, still more preferably greater than about 80%, 85%, 90%, 95%, 96%, 97%, 98%, or 99% amino acid sequence identity with a GabT protein of the *E. coli* strain K12, with the amino acid identity determined using a sequence alignment program such as CLUSTALW. Such antigens can be prepared, for example, by purification from enteric bacteria such as *E. coli*, by recombinant expression of a nucleic acid encoding a GabT peptide such as NCBI Accession No. AAC36832.1, by synthetic means such as solution or solid phase peptide synthesis, or by using phage display. One skilled in the art will appreciate that GabT is also known as (S)-3-amino-2-methylpropionate transaminase, GABA aminotransferase, GABA-AT, Gamma-amino-N-butyrate transaminase, and glutamate:succinic semialdehyde transaminase L-AIBAT.

The term "EcYedK" refers to a *Escherichia coli* strain K12 predicted protein that is that is immunoreactive with an anti-YedK antibody. Suitable EcYedK antigens useful in determining anti-YedK antibody levels in a sample include, without limitation, a YedK protein of the *E. coli* strain K12, a YedK polypeptide having substantially the same amino acid sequence as the YedK protein of the *E. coli* strain K12, or a fragment thereof such as an immunoreactive fragment thereof. A YedK polypeptide generally describes polypeptides having an amino acid sequence with greater than about 50% identity, preferably greater than about 60% identity, more preferably greater than about 70% identity, still more preferably greater than about 80%, 85%, 90%, 95%, 96%, 97%, 98%, or 99% amino acid sequence identity with a YedK protein of the *E. coli* strain K12, with the amino acid identity determined using a sequence alignment program such as CLUSTALW. Such antigens can be prepared, for example, by purification from enteric bacteria such as *E. coli*, by recombinant expression of a nucleic acid encoding a YedK peptide such as NCBI Accession No. AA48139, by synthetic means such as solution or solid phase peptide synthesis, or by using phage display.

The term "EcYbaN" refers to a *Escherichia coli* strain K12 inner membrane protein YbaN and that is immunoreactive with an anti-YbaN antibody. Suitable EcYbaN antigens useful in determining anti-YbaN antibody levels in a sample include, without limitation, a YbaN protein of the *E. coli* strain K12, a YbaN polypeptide having substantially the same amino acid sequence as the YbaN protein of the *E. coli* strain K12, or a fragment thereof such as an immunoreactive fragment thereof. A YbaN polypeptide generally describes polypeptides having an amino acid sequence with greater than about 50% identity, preferably greater than about 60% identity, more preferably greater than about 70% identity, still more preferably greater than about 80%, 85%, 90%, 95%, 96%, 97%, 98%, or 99% amino acid sequence identity with a YbaN protein of the *E. coli* strain K12, with the amino acid identity determined using a sequence alignment program such as CLUSTALW. Such antigens can be prepared, for example, by purification from enteric bacteria such as *E. coli*, by recombinant expression of a nucleic acid encoding a YbaN peptide such as Uniprot No. P0AAR5, by synthetic means such as solution or solid phase peptide synthesis, or by using phage display.

The term "EcYhgN" refers to a *Escherichia coli* strain K12 membrane protein that is predicted to function as an antibiotic transporter and that is immunoreactive with an anti-YhgN antibody. Suitable EcYhgN antigens useful in determining anti-YhgN antibody levels in a sample include, without limitation, a YhgN protein of the *E. coli* strain K12, a YhgN polypeptide having substantially the same amino acid sequence as the YhgN protein of the *E. coli* strain K12, or a fragment thereof such as an immunoreactive fragment thereof. A YhgN polypeptide generally describes polypeptides having an amino acid sequence with greater than about 50% identity, preferably greater than about 60% identity, more preferably greater than about 70% identity, still more preferably greater than about 80%, 85%, 90%, 95%, 96%, 97%, 98%, or 99% amino acid sequence identity with a YhgN protein of the *E. coli* strain K12, with the amino acid identity determined using a sequence alignment program such as CLUSTALW. Such antigens can be prepared, for example, by purification from enteric bacteria such as *E. coli*, by recombinant expression of a nucleic acid encoding a YhgN peptide such as NCBI Accession No. AAA58232.1, by synthetic means such as solution or solid phase peptide synthesis, or by using phage display. One skilled in the art will appreciate that YhgN is also known as predicted antibiotic transporter.

The term "RtMaga" refers to a *Ruminococcus torques* mannosyl-glycoprotein endo-beta-N-acetylglucosaminidase and that is immunoreactive with an anti-Maga antibody. Suitable RtMaga antigens useful in determining anti-Maga antibody levels in a sample include, without limitation, a Maga protein of the *Ruminococcus torques*, a Maga polypeptide having substantially the same amino acid sequence as the Maga protein of the *Ruminococcus torques*, or a fragment thereof such as an immunoreactive fragment thereof. A Maga polypeptide generally describes polypeptides having an amino acid sequence with greater than about 50% identity, preferably greater than about 60% identity, more preferably greater than about 70% identity, still more preferably greater than about 80%, 85%, 90%, 95%, 96%, 97%, 98%, or 99% amino acid sequence identity with a Maga protein of the *Ruminococcus torques*, with the amino acid identity determined using a sequence alignment program such as CLUSTALW. Such antigens can be prepared, for example, by purification from enteric bacteria such as *Ruminococcus torques*, by recombinant expression of a nucleic acid encoding a Maga peptide such as Uniprot No. D4M4S6, by synthetic means such as solution or solid phase peptide synthesis, or by using phage display.

The term "RtCpaF" refers to a *Ruminococcus bromii* Flp pilus assembly protein, ATPase CpF and that is immunoreactive with an anti-CpaF antibody. Suitable RbCpaF antigens useful in determining anti-CpaF antibody levels in a sample include, without limitation, a CpaF protein of the *Ruminococcus bromii*, a CpaF polypeptide having substantially the same amino acid sequence as the CpaF protein of the *Ruminococcus bromii*, or a fragment thereof such as an immunoreactive fragment thereof. A CpaF polypeptide generally describes polypeptides having an amino acid sequence with greater than about 50% identity, preferably greater than about 60% identity, more preferably greater than about 70% identity, still more preferably greater than about 80%, 85%, 90%, 95%, 96%, 97%, 98%, or 99% amino acid sequence identity with a CpaF protein of the *Ruminococcus bromii*, with the amino acid identity determined using a sequence alignment program such as CLUSTALW. Such antigens can be prepared, for example, by purification from enteric bacteria such as *R. bromii*, by recombinant expression of a nucleic acid encoding a CpaF peptide such as Uniprot No. D4L5L7, by synthetic means such as solution or solid phase peptide synthesis, or by using phage display.

The term "RtPilD" refers to a *Ruminococcus gnavus* pilin isopeptide linkage domain protein and that is immunoreactive with an anti-PilD antibody. Suitable RgPilD antigens useful in determining anti-PilD antibody levels in a sample include, without limitation, a PilD protein of the *Ruminococcus gnavus*, a PilD polypeptide having substantially the same amino acid sequence as the PilD protein of the *Ruminococcus gnavus*, or a fragment thereof such as an immunoreactive fragment thereof. A PilD polypeptide generally describes polypeptides having an amino acid sequence with greater than about 50% identity, preferably greater than about 60% identity, more preferably greater than about 70% identity, still more preferably greater than about 80%, 85%, 90%, 95%, 96%, 97%, 98%, or 99% amino acid sequence identity with a PilD protein of the *Ruminococcus gnavus*, with the amino acid identity determined using a sequence alignment program such as CLUSTALW. Such antigens can be prepared, for example, by purification from enteric bacteria such as *R. gnavus*, by recombinant expression of a nucleic acid encoding a PilD peptide such as Uniprot No. A7B5T4, by synthetic means such as solution or solid phase peptide synthesis, or by using phage display.

The term "LaFrc" refers to a protein of the *Lactobacillus acidophilus* that is immunoreactive with an anti-Frc antibody. Frc is predicted to be a formyl CoA transferase. Suitable Frc antigens useful in determining anti-Frc antibody levels in a sample include, without limitation, a Frc protein of the *L. acidophilus*, a Frc polypeptide having substantially the same amino acid sequence as the Frc protein of the *L. acidophilus*, or a fragment thereof such as an immunoreactive fragment thereof. A Frc polypeptide of the *L. acidophilus* generally describes polypeptides having an amino acid sequence with greater than about 50% identity, preferably greater than about 60% identity, more preferably greater than about 70% identity, still more preferably greater than about 80%, 85%, 90%, 95%, 96%, 97%, 98%, or 99% amino acid sequence identity with a Frc protein of the *L. acidophilus*, with the amino acid identity determined using a sequence alignment program such as CLUSTALW.

Such antigens can be prepared, for example, by purification from enteric bacteria such as *L. acidophilus*, by recombinant expression of a nucleic acid encoding a Frc peptide such as NCBI Ref. Seq. No. YP_193317 or UniProt. No. Q5FLY8, by synthetic means such as solution or solid phase peptide synthesis.

The term "LaEno" refers to a protein of the *Lactobacillus acidophilus* that is immunoreactive with an anti-Eno antibody. Eno is predicted to be a phosphopyruvate hydratase (enolase). Suitable LaEno antigens useful in determining anti-Eno antibody levels in a sample include, without limitation, an Eno protein of the *L. acidophilus*, an Eno polypeptide having substantially the same amino acid sequence as the Eno protein of the *L. acidophilus*, or a fragment thereof such as an immunoreactive fragment thereof. An Eno polypeptide of the *L. acidophilus* generally describes polypeptides having an amino acid sequence with greater than about 50% identity, preferably greater than about 60% identity, more preferably greater than about 70% identity, still more preferably greater than about 80%, 85%, 90%, 95%, 96%, 97%, 98%, or 99% amino acid sequence identity with a Eno protein of the *L. acidophilus*, with the amino acid identity determined using a sequence alignment program such as CLUSTALW. Such antigens can be prepared, for example, by purification from enteric bacteria such as *L. acidophilus*, by recombinant expression of a nucleic acid encoding an Eno peptide such as NCBI Ref. Seq. No. YP_193779 or UniProt. No. Q5FKM6, by synthetic means such as solution or solid phase peptide synthesis.

The term "LjEFTu" refers to a protein of the *Lactobacillus johnsonii* that is immunoreactive with an anti-EFTu antibody. EFTu is predicted to be an elongation factor Tu. Suitable EFTu antigens useful in determining anti-EFTu antibody levels in a sample include, without limitation, an EFTu protein of the *L. johnsonii*, an EFTu polypeptide having substantially the same amino acid sequence as the EFTu protein of the *L. acidophilus*, or a fragment thereof such as an immunoreactive fragment thereof. An EFTu polypeptide of the *L. johnsonii* generally describes polypeptides having an amino acid sequence with greater than about 50% identity, preferably greater than about 60% identity, more preferably greater than about 70% identity, still more preferably greater than about 80%, 85%, 90%, 95%, 96%, 97%, 98%, or 99% amino acid sequence identity with an EFTu protein of the *L. johnsonii*, with the amino acid identity determined using a sequence alignment program such as CLUSTALW. Such antigens can be prepared, for example, by purification from enteric bacteria such as *L. johnsonii*, by recombinant expression of a nucleic acid encoding an EFTu peptide such as NCBI Ref. Seq. No. NP_964865 or UniProt. No. Q74JU6, by synthetic means such as solution or solid phase peptide synthesis.

The term "BfOmpA" refers to a protein of the *Bacteroides fragilis* that is immunoreactive with an anti-OmpA antibody. OmpA is predicted to be a major outer membrane protein A. Suitable OmpA antigens useful in determining anti-OmpA antibody levels in a sample include, without limitation, an OmpA protein of the *B. fragilis*, an OmpA polypeptide having substantially the same amino acid sequence as the OmpA protein of the *B. fragilis*, or a fragment thereof such as an immunoreactive fragment thereof. An OmpA polypeptide of the *B. fragilis* generally describes polypeptides having an amino acid sequence with greater than about 50% identity, preferably greater than about 60% identity, more preferably greater than about 70% identity, still more preferably greater than about 80%, 85%, 90%, 95%, 96%, 97%, 98%, or 99% amino acid sequence identity with an OmpA protein of the *B. fragilis*, with the amino acid identity determined using a sequence alignment program such as CLUSTALW. Such antigens can be prepared, for example, by purification from enteric bacteria such as *B. fragilis*, by recombinant expression of a nucleic acid encoding an OmpA peptide such as NCBI Ref. Seq. No. YP_098863 or UniProt. No. Q64VP7, by synthetic means such as solution or solid phase peptide synthesis.

The term "PrOmpA" refers to a protein of the *Prevotella* species, e.g., *Prevotella* sp. oral taxon 472 str. F0295, that is immunoreactive with an anti-OmpA antibody. OmpA is predicted to be a immunoreactive antigen PG33 or major outer membrane protein A. Suitable OmpA antigens useful in determining anti-OmpA antibody levels in a sample include, without limitation, an OmpA protein of the *Prevotella* sp., an OmpA polypeptide having substantially the same amino acid sequence as the OmpA protein of the *Prevotella* sp., or a fragment thereof such as an immunoreactive fragment thereof. An OmpA polypeptide of the *Prevotella* sp. generally describes polypeptides having an amino acid sequence with greater than about 50% identity, preferably greater than about 60% identity, more preferably greater than about 70% identity, still more preferably greater than about 80%, 85%, 90%, 95%, 96%, 97%, 98%, or 99% amino acid sequence identity with an OmpA protein of the *Prevotella* sp., with the amino acid identity determined using a sequence alignment program such as CLUSTALW. Such antigens can be prepared, for example, by purification from enteric bacteria such as *Prevotella* sp., by recombinant expression of a nucleic acid encoding an OmpA peptide such as NCBI GenBank Accession No. EEX54413 or UniProt. No. C9PT48, by synthetic means such as solution or solid phase peptide synthesis.

The term "Cp10bA" refers to a protein of the *Clostridia perfringens* that is immunoreactive with an anti-10bA antibody. 10bA is predicted to be a 10b antigen. Suitable 10bA antigens useful in determining anti-10bA antibody levels in a sample include, without limitation, a 10bA protein of the *C. perfringens*, a 10bA polypeptide having substantially the same amino acid sequence as the 10bA protein of the *C. perfringens*, or a fragment thereof such as an immunoreactive fragment thereof. A 10bA polypeptide of the *C. perfringens* generally describes polypeptides having an amino acid sequence with greater than about 50% identity, preferably greater than about 60% identity, more preferably greater than about 70% identity, still more preferably greater than about 80%, 85%, 90%, 95%, 96%, 97%, 98%, or 99% amino acid sequence identity with a 10bA protein of the *C. perfringens*, with the amino acid identity determined using a sequence alignment program such as CLUSTALW. Such antigens can be prepared, for example, by purification from enteric bacteria such as *C. perfringens*, by recombinant expression of a nucleic acid encoding a 10bA peptide such as NCBI GenBank Accession No. EDT72304 or UniProt. No. B1V1I2, by synthetic means such as solution or solid phase peptide synthesis.

The term "CpSpA" refers to a protein of the *Clostridia perfringens* that is immunoreactive with an anti-SpA antibody. SpA is predicted to be a surface protective antigen SpA homolog. Suitable SpA antigens useful in determining anti-SpA antibody levels in a sample include, without limitation, a SpA protein of the *C. perfringens*, a SpA polypeptide having substantially the same amino acid sequence as the SpA protein of the *C. perfringens*, or a fragment thereof such as an immunoreactive fragment thereof. A SpA polypeptide of the *C. perfringens* generally describes polypeptides having an amino acid sequence with greater than about 50% identity, preferably greater than about 60% identity, more preferably greater than about 70% identity, still more preferably greater than about 80%, 85%, 90%, 95%, 96%, 97%, 98%, or 99% amino acid sequence identity with a SpA protein of the *C. perfringens*, with the amino acid identity determined using a sequence alignment program such as CLUSTALW. Such antigens can be prepared, for example, by purification from enteric bacteria such as *C. perfringens*, by recombinant expression of a nucleic acid encoding a SpA peptide such as NCBI Ref. Seq. No. YP_209686 or UniProt. No. Q5DWA9, by synthetic means such as solution or solid phase peptide synthesis.

The term "EfSant" refers to a protein of the *Enterococcus faecalis* that is immunoreactive with an anti-Sant antibody. Sant is predicted to be a surface antigen. Suitable Sant antigens useful in determining anti-Sant antibody levels in a sample include, without limitation, a Sant protein of the *E. faecalis*, a Sant polypeptide having substantially the same amino acid sequence as the Sant protein of the *E. faecalis*, or a fragment thereof such as an immunoreactive fragment thereof. A Sant polypeptide of the *E. faecalis* generally describes polypeptides having an amino acid sequence with greater than about 50% identity, preferably greater than about 60% identity, more preferably greater than about 70% identity, still more preferably greater than about 80%, 85%, 90%, 95%, 96%, 97%, 98%, or 99% amino acid sequence identity with a Sant protein of the *E. faecalis*, with the amino acid identity determined using a sequence alignment program such as CLUSTALW. Such antigens can be prepared, for example, by purification from enteric bacteria such as *E. faecalis*, by recombinant expression of a nucleic acid encoding a Sant peptide such as NCBI GenBank Accession No. EEU72780 or UniProt. No. C7W575, by synthetic means such as solution or solid phase peptide synthesis.

The term "LmOsp" refers to a protein of the *Listeria monocytogenes* that is immunoreactive with an anti-Osp antibody. Osp is predicted to be an outer surface antigen. Suitable Osp antigens useful in determining anti-Osp antibody levels in a sample include, without limitation, an Osp protein of the *L. monocytogenes*, an Osp polypeptide having substantially the same amino acid sequence as the Osp protein of the *L. monocytogenes*, or a fragment thereof such as an immunoreactive fragment thereof. An Osp polypeptide of the *L. monocytogenes* generally describes polypeptides having an amino acid sequence with greater than about 50% identity, preferably greater than about 60% identity, more preferably greater than about 70% identity, still more preferably greater than about 80%, 85%, 90%, 95%, 96%, 97%, 98%, or 99% amino acid sequence identity with an Osp protein of the *L. monocytogenes*, with the amino acid identity determined using a sequence alignment program such as CLUSTALW. Such antigens can be prepared, for example, by purification from enteric bacteria such as *L. monocytogenes*, by recombinant expression of a nucleic acid encoding an Osp peptide such as NCBI Ref. Seq. No. YP_002349810 or UniProt. No. B8DFK3, by synthetic means such as solution or solid phase peptide synthesis.

The term "SfET-2" refers to a protein of the *S. flexneri* that is immunoreactive with an anti-enterotoxin ET-2 antibody. ET-2 is predicted to be an enterotoxin. Suitable ET-2 antigens useful in determining anti-ET-2 antibody levels in a sample include, without limitation, an ET-2 protein of the *S. flexneri*, an ET-2 polypeptide having substantially the same amino acid sequence as the ET-2 protein of the *S. flexneri*, or a fragment thereof such as an immunoreactive fragment thereof. An ET-2 polypeptide of the *S. flexneri* generally describes polypeptides having an amino acid sequence with greater than about 50% identity, preferably greater than about 60% identity, more preferably greater than about 70% identity, still more preferably greater than about 80%, 85%, 90%, 95%, 96%, 97%, 98%, or 99% amino acid sequence identity with an ET-2 protein of the *S. flexneri*, with the amino acid identity determined using a sequence alignment program such as CLUSTALW. Such antigens can be prepared, for example, by purification from enteric bacteria such *S. flexneri*, by recombinant expression of a nucleic acid encoding an ET-2 peptide such as UniProt. No. Q7BEN0, by synthetic means such as solution or solid phase peptide synthesis.

The term "Cpatox" refers to a protein of the *C. perfringens* that is immunoreactive with an anti-alpha toxin antibody. αtox is predicted to be an alpha toxin. Suitable αtox antigens useful in determining anti-αtox antibody levels in a sample include, without limitation, an αtox protein of the *C. perfringens*, an αtox polypeptide having substantially the same amino acid sequence as the αtox protein of the *C. perfringens*, or a fragment thereof such as an immunoreactive fragment thereof. An αtox polypeptide of the *C. perfringens* generally describes polypeptides having an amino acid sequence with greater than about 50% identity, preferably greater than about 60% identity, more preferably greater than about 70% identity, still more preferably greater than about 80%, 85%, 90%, 95%, 96%, 97%, 98%, or 99% amino acid sequence identity with an αtox protein of the *C. perfringens*, with the amino acid identity determined using a sequence alignment program such as CLUSTALW. Such antigens can be prepared, for example, by purification from enteric bacteria such *C. perfringens*, by recombinant expression of a nucleic acid encoding an αtox peptide such as UniProt. No. Q3HR45, by synthetic means such as solution or solid phase peptide synthesis.

The term "Cpbtox" refers to a protein of the *C. perfringens* that is immunoreactive with an anti-beta2 toxin antibody. βtox is predicted to be a beta toxin. Suitable βtox antigens useful in determining anti-βtox antibody levels in a sample include, without limitation, a βtox protein of the *C. perfringens*, an βtox polypeptide having substantially the same amino acid sequence as the βtox protein of the *C. perfringens*, or a fragment thereof such as an immunoreactive fragment thereof. A βtox polypeptide of the *C. perfringens* generally describes polypeptides having an amino acid sequence with greater than about 50% identity, preferably greater than about 60% identity, more preferably greater than about 70% identity, still more preferably greater than about 80%, 85%, 90%, 95%, 96%, 97%, 98%, or 99% amino acid sequence identity with an βtox protein of the *C. perfringens*, with the amino acid identity determined using a sequence alignment program such as CLUSTALW. Such antigens can be prepared, for example, by purification from enteric bacteria such *C. perfringens*, by recombinant expression of a nucleic acid encoding an βtox peptide such as UniProt. No. B1R976, by synthetic means such as solution or solid phase peptide synthesis.

The term "EcSta2" refers to a protein of the *E. coli* that is immunoreactive with an anti-heat stable toxin Sta2 antibody. Sta2 is predicted to be a heat-stable toxin. Suitable Sta2 antigens useful in determining anti-Sta2 antibody levels in a sample include, without limitation, a Sta2 protein of the *E. coli*, a Sta2 polypeptide having substantially the same amino acid sequence as the Sta2 protein of the *E. coli*, or a fragment thereof such as an immunoreactive fragment thereof. A Sta2 polypeptide of the *E. coli* generally describes polypeptides having an amino acid sequence with greater than about 50% identity, preferably greater than about 60% identity, more preferably greater than about 70% identity, still more preferably greater than about 80%, 85%, 90%, 95%, 96%, 97%, 98%, or 99% amino acid sequence identity with a Sta2 protein of the *E. coli*, with the amino acid identity determined using a sequence alignment program such as CLUSTALW. Such antigens can be prepared, for example, by purification from enteric bacteria such *E. coli*, by recombinant expression of a nucleic acid encoding a Sta2 peptide such as UniProt. No. Q2WE95, by synthetic means such as solution or solid phase peptide synthesis.

The term "EcOStx2a" refers to a protein of the *E. coli* H7:O157 that is immunoreactive with an anti-Stx2a antibody. Stx2a is predicted to be a Shiga toxin subunit A. Suitable Stx2a antigens useful in determining anti-Stx2a antibody levels in a sample include, without limitation, a Stx2a protein of the *E. coli* H7:O157, a Stx2a polypeptide having substantially the same amino acid sequence as the Stx2a protein of the *E. coli*, or a fragment thereof such as an immunoreactive fragment thereof. A Stx2a polypeptide of the *E. coli* H7:O157 generally describes polypeptides having an amino acid sequence with greater than about 50% identity, preferably greater than about 60% identity, more preferably greater than about 70% identity, still more preferably greater than about 80%, 85%, 90%, 95%, 96%, 97%, 98%, or 99% amino acid sequence identity with a Stx2a protein of the *E. coli* H7:O157, with the amino acid identity determined using a sequence alignment program such as CLUSTALW. Such antigens can be prepared, for example, by purification from enteric bacteria such *E. coli* H7:O157, by recombinant expression of a nucleic acid encoding a Stx2a peptide such as UniProt. No. B6ZXF5, by synthetic means such as solution or solid phase peptide synthesis.

The term “CjCdtB/C” refers to a protein of the *Campylobacter jejuni* that is immunoreactive with an anti-CdtB/C antibody. CdtB is predicted to be a cytolethal distending toxin subunit B and CdtC is predicted to be a cytolethal distending toxin subunit C. Suitable CdtB/C antigens useful in determining anti-CdtB/C antibody levels in a sample include, without limitation, a CdtB/C protein of the *C. jejuni*, a CdtB/C polypeptide having substantially the same amino acid sequence as the CdtB/C a protein of the *C. jejuni*, or a fragment thereof such as an immunoreactive fragment thereof. A CdtB/C polypeptide of the *C. jejuni* generally describes polypeptides having an amino acid sequence with greater than about 50% identity, preferably greater than about 60% identity, more preferably greater than about 70% identity, still more preferably greater than about 80%, 85%, 90%, 95%, 96%, 97%, 98%, or 99% amino acid sequence identity with a CdtB/C protein of the *C. jejuni*, with the amino acid identity determined using a sequence alignment program such as CLUSTALW. Such antigens can be prepared, for example, by purification from enteric bacteria such *C. jejuni*, by recombinant expression of a nucleic acid encoding a CdtB/C peptide such as UniProt. Nos. Q46101 and Q46102, by synthetic means such as solution or solid phase peptide synthesis.

The term “CjCdA/B” refers to a protein of the *Clostridium difficile* that is immunoreactive with an anti-toxinA/B antibody. CdA is predicted to be toxinA and CdB is predicted to be toxin B. Suitable CdA/B antigens useful in determining anti-CdA/B antibody levels in a sample include, without limitation, a CdA/B protein of the *C. difficile*, a CdA/B polypeptide having substantially the same amino acid sequence as the CdA/B a protein of the *C. difficile*, or a fragment thereof such as an immunoreactive fragment thereof. A CdA/B polypeptide of the *C. difficile* generally describes polypeptides having an amino acid sequence with greater than about 50% identity, preferably greater than about 60% identity, more preferably greater than about 70% identity, still more preferably greater than about 80%, 85%, 90%, 95%, 96%, 97%, 98%, or 99% amino acid sequence identity with a CdA/B protein of the *C. difficile*, with the amino acid identity determined using a sequence alignment program such as CLUSTALW. Such antigens can be prepared, for example, by purification from enteric bacteria such *C. difficile*, by recombinant expression of a nucleic acid encoding a CdA/B peptide such as UniProt. Nos. P16154 and P18177, by synthetic means such as solution or solid phase peptide synthesis.

In some embodiments, the method comprises determining the level of at least one bacterial antigen antibody marker, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or 35 markers by measuring the level of antibody against the bacterial antigen present in a sample from an individual. In some instances, if an individual possessing at least one bacterial antigen antibody at a level that is higher or lower than a healthy control, it is indicative of the individual having IBS. The presence or level of the bacterial antigen antibody in the individual can be correlated to the level of the disease.

In some embodiments, the level of at least one antibody against a commensal bacterial antigen in a patient sample indicates that the patient has IBS, wherein the commensal bacterial antigen is selected from the group consisting of LaFrc, LaEno, LjEFTu, BfOmpA, PrOmpA, Cp10bA, CpSpA, EfSant, LmOsp, and combinations thereof. If it is determined that the level of an antibody against a bacterial antigen from the bacterial class *Bacteroides fragilis* or *Prevotella* sp. is reduced in a sample taken from an individual, compared to the level from a normal control sample, then the individual is diagnosed as having IBS. If it is determined that the level of an antibody against a bacterial antigen from the bacterial class selected from the group consisting of *Clostridia perfringens, Enterococcus, Listeria* and other Firmicutes classes is higher in an individual’s sample compared to a healthy control sample, then the individual is diagnosed as having IBS.

In some embodiments, subjects with a lower level of antibodies against Bacteriodetes class bacteria compared to healthy controls are more likely to have IBS. In contrast, subjects with a higher level of antibodies against Clostridia, Mollicutes and/or Bacilli class bacteria compared to healthy control may be more likely to have IBS.

In other embodiments, the method provided herein is used to determine that a subject with an increased level (e.g., amount, concentration, ratio) of antibodies to a Firmicutes antigen such as a LaFrc, LaEno, LjEfTu, Cp10ba, CpSpaA, EfSant, and LmOsp antigen, over an Bacteriodetes antigen, such as a BfOmpA and PrOmpA antigen, is predicted that the subject has an increased likelihood of having IBS.

C. Mast Cell Markers

1. β-Tryptase

In one aspect, a method for aiding in the diagnosis of irritable bowel syndrome (IBS) in a subject is provided, the method comprises: a) determining the level of β-tryptase present in a sample from a subject; and (b) comparing the level of β-tryptase present in the sample to that of a control level, wherein an increased level of β-tryptase present in the sample from the subject is indicative of an increase likelihood of the subjecting having IBS.

In some embodiments, the method of determining the level of β-tryptase present in a sample from a subject comprises: (a) contacting a biological sample from the subject with a β-tryptase binding moiety under conditions suitable to transform β-tryptase present in the sample into a complex comprising β-tryptase and the β-tryptase binding moiety; and (b) determining the level of the complex, thereby determining the level of β-tryptase present in the sample.

In a specific embodiments, the method of determining the level of β-tryptase present in a sample from a subject comprises: (a) contacting a sample having β-tryptase contained therein under conditions suitable to transform the β-tryptase into a complex comprising β-tryptase and a capture anti-tryptase antibody; (b) contacting the complex with an enzyme labeled indicator antibody to transform the complex into a labeled complex; (c) contacting the labeled complex with a substrate for the enzyme; and (d) detecting the presence or level of β-tryptase in the sample.

An exemplary embodiment of a method for determining the level of β-tryptase present in a sample from a subject is described in U.S. Pat. No. 8,114,616, the disclosure of which is herein incorporated by reference in its entirety for all purposes.

In preferred embodiments, β-tryptase, histamine, and/or PGE2 are detected from the same sample, although in certain instances the biomarkers may be detected in samples taken from the same individual, for example, at the same time or at different times. In certain embodiments, the biomarkers are detected in separate assays performed with different aliquots of a blood or serum sample from a subject. In other embodiments, the biomarkers are detected in a single multiplex detection assay, for example, in a Luminex xAMP assay.

2. Histamine

In a specific embodiment, the present invention provides a method to aid in the diagnosis of IBS, the method comprises: (a) contacting a sample having histamine contained therein under conditions suitable to transform the acetylated histamine into a complex comprising histamine and a capture anti-histamine antibody; (b) contacting the complex with an enzyme labeled indicator antibody to transform the complex into a labeled complex; (c) contacting the labeled complex with a substrate for the enzyme; and (d) detecting the level of histamine in the sample.

An exemplary embodiment of the assay is a histamine enzyme immunoassay such as the EIA Histamine Assay (Cat. No. IM2015, ImmunoTech). Briefly, histamine present in the sample, calibrator or control is acetylated by admixing 25 µl of acylation buffer, 100 µl of samples, calibrators or controls, and 25 µl of acylation reagent, and vortexing immediately. 50 µl of the acylated samples, calibrators or controls are added to the anti-histamine antibody coated wells of the microtiter assay plate. Then, 200 µl of alkaline phosphatase-histamine conjugate is added to the plate. The plate is incubated for 2 hours at 2-8° C. with shaking. The wells are washed with wash solution, and 200 µl of chromogenic substrate is added to the wells. The plate is incubated for 30 minutes at 18-25° C. in the dark with shaking. Then, 50 µl of reaction stop solution is added before reading the luminescence with a luminescence plate reader. The Relative Luminescent Unit (RLU) and the histamine concentration of the calibrators are plotted using graphing software such as Graphpad (Prism). The levels of histamine in the sample and control are calculated by interpolation from a calibrator curve that is performed in the same assay as the sample.

3. Prostaglandin E2

In a specific embodiment, the present invention provides a method to aid in the diagnosis of IBS, the assay comprising: (a) contacting a sample having prostaglandin E2 contained therein under conditions suitable to transform the prostaglandin E2 into a complex comprising prostaglandin E2 and a capture anti-prostaglandin E2 antibody; (b) contacting the complex with an enzyme labeled indicator antibody to transform the complex into a labeled complex; (c) contacting the labeled complex with a substrate for the enzyme; and (d) detecting the level of prostaglandin E2 in the sample.

An exemplary embodiment of the assay is a PGE2 competitive enzyme immunoassay such as the Prostaglandin E2 EIA Kit-Monoclonal (Cat. No. 514010, Cayman Chemical). Briefly, 50 µl of calibrator (standard) or sample is added to wells of a precoated goat anti-mouse IgG microtiter assay plate. 50 µl of PGE2 tracer (covalently conjugated PGE2 and acetylcholinesterase) is added, and then 50 µl of anti-PGE2 mouse IgG. The plate is incubated for 18 hours at 4° C. with shaking. The plate is washed 5 times with wash buffer. 200 µl of developing reagent (e.g., Ellman's reagent) is added to the wells. The plate is incubated for 60-90 minutes in the dark with shaking. Luminescence is read at 405 nm with a luminescence plate reader. The Relative Luminescent Unit (RLU) and the prostaglandin E2 concentration of the calibrators are plotted using graphing software such as GraphPad Prism (GraphPad Software, La Jolla, Calif.). The levels of prostaglandin E2 in the sample and control are calculated by interpolation from a calibrator curve that is performed in the same assay as the sample.

D. Bile Acid Malabsorption Markers

In some embodiments, bile acid malabsorption (BAM) markers for use in the present invention are selected from a group consisting of bile acid, FXR, cholesterol, 7α-hydroxy-4-cholesten-3-one (C4), FGF19, CYP7A, and a combination thereof.

In some embodiments, level of a BAM marker such as 7α-hydroxy-4-cholesten-3-one and FGF19 is detected by a competitive enzyme immunoassay. In some instances, an antibody against 7α-hydroxy-4-cholesten-3-one is used. In some instances, an antibody against FGF19 is used. Assays for measuring 7α-hydroxy-4-cholesten-3-one are described in, e.g., PCT Application No. PCT/IB2014/061634, filed May 27, 2014. Other methods for measuring 7α-hydroxy-4-cholesten-3-one include high pressure liquid chromatography, tandem mass spectrometry (HPLC-MS/MS) described in, e.g., Camilleri et al., *Neurogastroenterol* i, 2009, 21(7):734-e43 or electrospray ionization liquid chromatography-tandem mass spectrometry (ESI-LC-MS/MS) described in, e.g., Honda et al., *J Lipid Research,* 2007, 48:458-464.

E. Serotonin Markers

In some embodiments, the serotonin markers for use in the present invention are selected from a group consisting of serotonin (5-HT), 5-hydroxyindoleacetic acid (5-HIAA), serotonin-O-sulfate, serotonin-O-phosphate, and a combination thereof. The level of one or more of the serotonin markers can be measured using a competitive enzyme immunoassay. In some instances, a derivative or analog of the serotonin marker is used in the assay. In other instances, an antibody against serotonin or a metabolite thereof can be used to detect the serotonin marker in a biological sample from an individual. Assays for measuring serotonin and metabolites thereof are described in, e.g., PCT Application No. PCT/IB2014/061634, filed May 22, 2014.

Levels of serotonin and metabolites thereof can be measured by other methods such liquid chromatography, e.g., HPLC/MS, or immunological methods such as using commercially available serotonin-specific antibodies from, for example, Abcam (Cambridge, Mass.), Dako (Carpinteria, Calif.), and Santa Cruz Biotechnology (Santa Cruz, Calif.).

In some embodiments, the sample is derivatized to increase the stability of serotonin and metabolites thereof prior to measuring their levels. For instance, the sample can be mixed with a derivatization mix, such as one containing 0.1M CAPS buffer (pH 11.0), 0.1M p-(aminomethyl)benzyl compound, 0.05 m potassium hexacyanoferrate (III), and methanol at a ratio of 10:11:22:23 (v:v:v:v).

F. Kynurenine Markers

Irregularities of serotonin function in IBS may be due to changes in the metabolism of the serotonin precursor L-tryptophan. Tryptophan is an essential amino acid that serves as a precursor to serotonin but which can alternatively be metabolized along the kynurenine pathway. This, in turn, leads to the production of other neuroactive agents. It has been shown that kynurenine levels and the kynurenine:tryptophan ratio are increased in IBS.

In some embodiments, the kynurenine markers for use in the present invention are selected from a group consisting of kynurenine (K), kynurenic acid (KyA), anthranilic acid (AA), 3-hydroxykynurenine (3-HK), 3-hydroxyanthranilic acid (3-HAA), xanthurenic acid (XA), quinolinic acid (QA), tryptophan, 5-hydroxytryptophan (5-HTP), and a combination thereof. The level of one or more of the kynurenine markers can be measured using a competitive enzyme immunoassay. In some instances, a derivative or analog of the kynurenine marker is used in the assay. In other instances, an antibody against kynurenine or a metabolite thereof can be used to detect the kynurenine marker in a biological sample from an individual. Assays for measuring tryptophan, kynurenine and metabolites thereof are described in, e.g., PCT Application No. PCT/IB2014/061634. Levels of the kynurenine markers can also be measured by other methods such liquid chromatography, e.g., HPLC, HPLC/MS, and the like.

G. Inflammatory Markers

A variety of inflammatory markers, including biochemical markers, serological markers, protein markers, and other clinical characteristics, are suitable for use in the methods of the present invention for diagnosing IBS and/or subtypes thereof. In certain aspects, the methods described herein utilize the application of an algorithm (e.g., statistical analysis) to the presence, concentration level, and/or genotype determined for one or more of the inflammatory markers to aid or assist in predicting that a subject has IBS and/or a subtype thereof.

Non-limiting examples of inflammatory markers include: biochemical, serological, and protein markers such as, e.g., cytokines including interleukins, acute phase proteins, cellular adhesion molecules, and combinations thereof.

1. Cytokines

The determination of the presence or level of at least one cytokine in a sample is particularly useful in the present invention. As used herein, the term "cytokine" includes any of a variety of polypeptides or proteins secreted by immune cells that regulate a range of immune system functions and encompasses small cytokines such as chemokines. The term "cytokine" also includes adipocytokines, which comprise a group of cytokines secreted by adipocytes that function, for example, in the regulation of body weight, hematopoiesis, angiogenesis, wound healing, insulin resistance, the immune response, and the inflammatory response.

In certain aspects, the presence or level of at least one cytokine including, but not limited to, TNF-α, TNF-related weak inducer of apoptosis (TWEAK), osteoprotegerin (OPG), IFN-α, IFN-β, IFN-γ, IL-1α, IL-1β, IL-1 receptor antagonist (IL-1ra), IL-2, IL-4, IL-5, IL-6, soluble IL-6 receptor (sIL-6R), IL-7, IL-8, IL-9, IL-10, IL-12, IL-13, IL-15, IL-17, IL-23, and IL-27 is determined in a sample. In certain other aspects, the presence or level of at least one chemokine such as, for example, CXCL1/GRO1/GROα, CXCL2/GRO2, CXCL3/GRO3, CXCL4/PF-4, CXCL5/ENA-78, CXCL6/GCP-2, CXCL7/NAP-2, CXCL9/MIG, CXCL10/IP-10, CXCL11/I-TAC, CXCL12/SDF-1, CXCL13/BCA-1, CXCL14/BRAK, CXCL15, CXCL16, CXCL17/DMC, CCL1, CCL2/MCP-1, CCL3/MIP-1α, CCL4/MIP-1β, CCL5/RANTES, CCL6/C10, CCL7/MCP-3, CCL8/MCP-2, CCL9/CCL10, CCL11/Eotaxin, CCL12/MCP-5, CCL13/MCP-4, CCL14/HCC-1, CCL15/MIP-5, CCL16/LEC, CCL17/TARC, CCL18/MIP-4, CCL19/MIP-3β, CCL20/MIP-3α, CCL21/SLC, CCL22/MDC, CCL23/MPIF1, CCL24/Eotaxin-2, CCL25/TECK, CCL26/Eotaxin-3, CCL27/CTACK, CCL28/MEC, CL1, CL2, and CX$_3$CL1 is determined in a sample. In certain further aspects, the presence or level of at least one adipocytokine including, but not limited to, leptin, adiponectin, resistin, active or total plasminogen activator inhibitor-1 (PAI-1), visfatin, and retinol binding protein 4 (RBP4) is determined in a sample. Preferably, the presence or level of TNFα, IL-6, IL-1β, IFN-γ, and/or IL-10 is determined.

In certain instances, the presence or level of a particular cytokine is detected at the level of mRNA expression with an assay such as, for example, a hybridization assay or an amplification-based assay. In certain other instances, the presence or level of a particular cytokine is detected at the level of protein expression using, for example, an immunoassay (e.g., ELISA) or an immunohistochemical assay. Suitable ELISA kits for determining the presence or level of a cytokine such as IL-6, IL-1β, or TWEAK in a serum, plasma, saliva, or urine sample are available from, e.g., R&D Systems, Inc. (Minneapolis, Minn.), Neogen Corp. (Lexington, Ky.), Alpco Diagnostics (Salem, N.H.), Assay Designs, Inc. (Ann Arbor, Mich.), BD Biosciences Pharmingen (San Diego, Calif.), Invitrogen (Camarillo, Calif.), Calbiochem (San Diego, Calif.), CHEMICON International, Inc. (Temecula, Calif.), Antigenix America Inc. (Huntington Station, N.Y.), QIAGEN Inc. (Valencia, Calif.), Bio-Rad Laboratories, Inc. (Hercules, Calif.), and/or Bender MedSystems Inc. (Burlingame, Calif.).

2. Acute Phase Proteins

The determination of the presence or level of one or more acute-phase proteins in a sample is also useful in the present invention. Acute-phase proteins are a class of proteins whose plasma concentrations increase (positive acute-phase proteins) or decrease (negative acute-phase proteins) in response to inflammation. This response is called the acute-phase reaction (also called acute-phase response). Examples of positive acute-phase proteins include, but are not limited to, C-reactive protein (CRP), D-dimer protein, mannose-binding protein, alpha 1-antitrypsin, alpha 1-antichymotrypsin, alpha 2-macroglobulin, fibrinogen, prothrombin, factor VIII, von Willebrand factor, plasminogen, complement factors, ferritin, serum amyloid P component, serum amyloid A (SAA), orosomucoid (alpha 1-acid glycoprotein, AGP), ceruloplasmin, haptoglobin, and combinations thereof. Non-limiting examples of negative acute-phase proteins include albumin, transferrin, transthyretin, transcortin, retinol-binding protein, and combinations thereof. Preferably, the presence or level of CRP and/or SAA is determined.

In certain instances, the presence or level of a particular acute-phase protein is detected at the level of mRNA expression with an assay such as, for example, a hybridization assay or an amplification-based assay. In certain other instances, the presence or level of a particular acute-phase protein is detected at the level of protein expression using, for example, an immunoassay (e.g., ELISA) or an immunohistochemical assay. For example, a sandwich colorimetric ELISA assay available from Alpco Diagnostics (Salem, N.H.) can be used to determine the level of CRP in a serum, plasma, urine, or stool sample. Similarly, an ELISA kit available from Biomeda Corporation (Foster City, Calif.) can be used to detect CRP levels in a sample. Other methods for determining CRP levels in a sample are described in, e.g., U.S. Pat. Nos. 6,838,250 and 6,406,862; and U.S. Patent Publication Nos. 20060024682 and 20060019410. Additional methods for determining CRP levels include, e.g., immunoturbidimetry assays, rapid immunodiffusion assays, and visual agglutination assays. Suitable ELISA kits for determining the presence or level of SAA in a sample such as serum, plasma, saliva, urine, or stool are available from, e.g., Antigenix America Inc. (Huntington Station, N.Y.), Abazyme (Needham, Mass.), USCN Life (Missouri City, Tex.), and/or U.S. Biological (Swampscott, Mass.).

C-reactive protein (CRP) is a protein found in the blood in response to inflammation (an acute-phase protein). CRP is typically produced by the liver and by fat cells (adipocytes). It is a member of the pentraxin family of proteins. The human CRP polypeptide sequence is set forth in, e.g., Genbank Accession No. NP_000558. The human CRP mRNA (coding) sequence is set forth in, e.g., Genbank Accession No. NM_000567. One skilled in the art will appreciate that CRP is also known as PTX1, MGC88244, and MGC149895.

Serum amyloid A (SAA) proteins are a family of apolipoproteins associated with high-density lipoprotein (HDL) in plasma. Different isoforms of SAA are expressed constitutively (constitutive SAAs) at different levels or in response to inflammatory stimuli (acute phase SAAs). These proteins are predominantly produced by the liver. The conservation of these proteins throughout invertebrates and vertebrates suggests SAAs play a highly essential role in all animals. Acute phase serum amyloid A proteins (A-SAAs) are secreted during the acute phase of inflammation. The human SAA polypeptide sequence is set forth in, e.g., Genbank Accession No. NP_000322. The human SAA mRNA (coding) sequence is set forth in, e.g., Genbank Accession No. NM_000331. One skilled in the art will appreciate that SAA is also known as PIG4, TP53I4, MGC111216, and SAA1.

3. Cellular Adhesion Molecules (IgSF CAMs)

The determination of the presence or level of one or more immunoglobulin superfamily cellular adhesion molecules in a sample is also useful in the present invention. As used herein, the term "immunoglobulin superfamily cellular adhesion molecule" (IgSF CAM) includes any of a variety of polypeptides or proteins located on the surface of a cell that have one or more immunoglobulin-like fold domains, and which function in intercellular adhesion and/or signal transduction. In many cases, IgSF CAMs are transmembrane proteins. Non-limiting examples of IgSF CAMs include Neural Cell Adhesion Molecules (NCAMs; e.g., NCAM-120, NCAM-125, NCAM-140, NCAM-145, NCAM-180, NCAM-185, etc.), Intercellular Adhesion Molecules (ICAMs, e.g., ICAM-1, ICAM-2, ICAM-3, ICAM-4, and ICAM-5), Vascular Cell Adhesion Molecule-1 (VCAM-1), Platelet-Endothelial Cell Adhesion Molecule-1 (PECAM-1), L1 Cell Adhesion Molecule (L1CAM), cell adhesion molecule with homology to L1CAM (close homolog of L1) (CHL1), sialic acid binding Ig-like lectins (SIGLECs; e.g., SIGLEC-1, SIGLEC-2, SIGLEC-3, SIGLEC-4, etc.), Nectins (e.g., Nectin-1, Nectin-2, Nectin-3, etc.), and Nectin-like molecules (e.g., Necl-1, Necl-2, Necl-3, Necl-4, and Necl-5). Preferably, the presence or level of ICAM-1 and/or VCAM-1 is determined.

ICAM-1 is a transmembrane cellular adhesion protein that is continuously present in low concentrations in the membranes of leukocytes and endothelial cells. Upon cytokine stimulation, the concentrations greatly increase. ICAM-1 can be induced by IL-1 and TNFα and is expressed by the vascular endothelium, macrophages, and lymphocytes. In IBD, proinflammatory cytokines cause inflammation by upregulating expression of adhesion molecules such as ICAM-1 and VCAM-1. The increased expression of adhesion molecules recruit more lymphocytes to the infected tissue, resulting in tissue inflammation (see, Goke et al., *J., Gastroenterol.*, 32:480 (1997); and Rijcken et al., *Gut*, 51:529 (2002)). ICAM-1 is encoded by the intercellular adhesion molecule 1 gene (ICAM1; Entrez GeneID:3383; Genbank Accession No. NM_000201) and is produced after processing of the intercellular adhesion molecule 1 precursor polypeptide (Genbank Accession No. NP_000192).

VCAM-1 is a transmembrane cellular adhesion protein that mediates the adhesion of lymphocytes, monocytes, eosinophils, and basophils to vascular endothelium. Upregulation of VCAM-1 in endothelial cells by cytokines occurs as a result of increased gene transcription (e.g., in response to Tumor necrosis factor-alpha (TNFα) and Interleukin-1 (IL-1)). VCAM-1 is encoded by the vascular cell adhesion molecule 1 gene (VCAM1; Entrez GeneID:7412) and is produced after differential splicing of the transcript (Genbank Accession No. NM_001078 (variant 1) or NM_080682 (variant 2)), and processing of the precursor polypeptide splice isoform (Genbank Accession No. NP_001069 (isoform a) or NP_542413 (isoform b)).

In certain instances, the presence or level of an IgSF CAM is detected at the level of mRNA expression with an assay such as, for example, a hybridization assay or an amplification-based assay. In certain other instances, the presence or level of an IgSF CAM is detected at the level of protein expression using, for example, an immunoassay (e.g., ELISA) or an immunohistochemical assay. Suitable antibodies and/or ELISA kits for determining the presence or level of ICAM-1 and/or VCAM-1 in a sample such as a tissue sample, biopsy, serum, plasma, saliva, urine, or stool are available from, e.g., Invitrogen (Camarillo, Calif.), Santa Cruz Biotechnology, Inc. (Santa Cruz, Calif.), and/or Abcam Inc. (Cambridge, Mass.).

H. Diagnostic Model

In some embodiments of the present invention, a diagnostic model is established using a retrospective cohort with known outcomes of a clinical subtype of IBS and healthy controls. In some instances, the diagnostic model comprises an oxidative stress score, a mast cell score, a serotonin score, a BAM score, a microbiome score, and a inflammatory score. The diagnostic model is generated by applying the retrospective data on individuals with IBS and healthy controls to statistical algorithms. In some embodiments, the oxidative stress score is derived by applying logistic regression analysis to the level of one or more kynurenine markers determined in a retrospective cohort. In some embodiments, the mast cell score is derived by applying logistic regression analysis to the level of one or more mast cell markers determined in a retrospective cohort. In some embodiments, the serotonin score is derived by applying logistic regression analysis to the level of one or more serotonin markers determined in a retrospective cohort. In some embodiments, the bile acid malabsorption score is derived by applying logistic regression analysis to the level of one or more bile acid malabsorption markers determined in a retrospective cohort. In some embodiments, the microbiome score is derived by applying logistic regression analysis to the level of one or more bacterial antigen antibody markers determined in a retrospective cohort. In some embodiments, the inflammatory score is derived by applying logistic regression analysis to the level of one or more inflammatory markers determined in a retrospective cohort. For instance, a diagnostic model was generated using retrospective data of kynurenine markers, mast cell markers, serotonin markers, BAM markers, bacterial antigen antibody markers and inflammatory markers, in combination with a logistic regression machine learning algorithm.

I. Statistical Analysis

In certain instances, the statistical algorithm or statistical analysis is a learning statistical classifier system. In one aspect, the algorithm can be trained with known samples and thereafter validated with samples of known identity. As used herein, the term "learning statistical classifier system" includes a machine learning algorithmic technique capable of adapting to complex data sets (e.g., panel of markers of interest and/or list of IBS-related symptoms) and making decisions based upon such data sets. The learning statistical classifier system can be selected from the group consisting of a random forest (RF), classification and regression tree (C&RT), boosted tree, neural network (NN), support vector machine (SVM), general chi-squared automatic interaction detector model, interactive tree, multiadaptive regression spline, machine learning classifier, and combinations thereof. Preferably, the learning statistical classifier system is a tree-based statistical algorithm (e.g., RF, C&RT, etc.) and/or a NN (e.g., artificial NN, etc.). Additional examples of learning statistical classifier systems suitable for use in the present invention are described in U.S. Patent Application Publication Nos. 2008/0085524, 2011/0045476 and 2012/0171672. In certain embodiments, the methods comprise classifying a sample from the subject as an IBS sample or non-IBS sample (e.g., sample from a healthy control).

In certain instances, the statistical algorithm is a single learning statistical classifier system. Preferably, the single learning statistical classifier system comprises a tree-based statistical algorithm such as a RF or C&RT. As a non-limiting example, a single learning statistical classifier system can be used to classify the sample as an IBS sample or non-IBS sample (e.g., healthy control) based upon a prediction or probability value and the presence or level of at least one diagnostic marker (i.e., diagnostic marker profile comprising a bacterial antigen antibody marker profile and/or a mast cell marker profile), alone or in combination with the presence or severity of at least one symptom (i.e., symptom profile). The use of a single learning statistical classifier system typically classifies the sample as an IBS sample with a sensitivity, specificity, positive predictive value, negative predictive value, and/or overall accuracy of at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%. As such, the classification of a sample as an IBS sample or non-IBS sample is useful for aiding in the diagnosis of IBS in a subject.

In certain other instances, the statistical algorithm is a combination of at least two learning statistical classifier systems. Preferably, the combination of learning statistical classifier systems comprises a RF and a NN, e.g., used in tandem or parallel. As a non-limiting example, a RF can first be used to generate a prediction or probability value based upon the diagnostic marker profile, alone or in combination with a symptom profile, and a NN can then be used to classify the sample as an IBS sample or non-IBS sample based upon the prediction or probability value and the same or different diagnostic marker profile or combination of profiles. Advantageously, the hybrid RF/NN learning statistical classifier system of the present invention classifies the sample as an IBS sample with a sensitivity, specificity, positive predictive value, negative predictive value, and/or overall accuracy of at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%. In a particularly preferred embodiment, the statistical algorithm is a random forest classifier or a combination of a random forest classifier and a neural network classifier.

In some instances, the data obtained from using the learning statistical classifier system or systems can be processed using a processing algorithm. Such a processing algorithm can be selected, for example, from the group consisting of a multilayer perceptron, backpropagation network, and Levenberg-Marquardt algorithm. In other instances, a combination of such processing algorithms can be used, such as in a parallel or serial fashion.

The various statistical methods and models described herein can be trained and tested using a cohort of samples from healthy individuals and IBS patients. For example, samples from patients diagnosed by a physician, and preferably by a gastroenterologist, as having IBS or a clinical subtype thereof using a biopsy, colonoscopy, or an immunoassay as described in, e.g., U.S. Pat. Publication No. 2010/0094560, are suitable for use in training and testing the statistical methods and models of the present invention. Samples from patients diagnosed with IBS can also be stratified into IBS subtypes using an immunoassay as described in, e.g., U.S. Pat. No. 8,463,553 and U.S. Pat. Publication Nos. 2010/0094560 and 2008/0085524. Samples from healthy individuals can include those that were not identified as IBS samples. One skilled in the art will know of additional techniques and diagnostic criteria for obtaining a cohort of patient samples that can be used in training and testing the statistical methods and models of the present invention.

J. Methods of Predicting Celiac Disease (CD)

In some embodiments, the sample from the subject is assayed to determine if it is a celiac disease sample or a non-celiac disease sample. If it is predicted to be a non-celiac disease sample, it progresses to the next module where it is determined if the sample is an inflammatory bowel disease (IBD) sample or a non-IBD sample In some embodiments, the method for determining whether a sample is a CD sample or a non-CD sample includes measuring the level of one or more CD markers, such as, but not limited to, an anti-gliadin IgA antibody, an anti-gliadin IgG antibody, an anti-tissue transglutaminase (tTG) antibody, an anti-endomysial antibody (EMA) and combinations thereof. In other embodiments, the methods includes measuring the level of each of the following CD markers: an anti-gliadin IgA antibody, an anti-gliadin IgG antibody, an anti-tissue transglutaminase (tTG) antibody, and an anti-endomysial antibody (EMA).

In certain instances, the presence or absence of markers of CD is determined using an immunoassay or an immunohistochemical assay. A non-limiting example of an immunoassay suitable for use in the methods of the present invention includes an enzyme-linked immunosorbent assay (ELISA). Examples of immunohistochemical assays suitable for use in the methods of the present invention include, but are not limited to, immunofluorescence assays such as direct fluorescent antibody assays, indirect fluorescent antibody (IFA) assays, anticomplement immunofluorescence assays, and avidin-biotin immunofluorescence assays. Other types of immunohistochemical assays include immunoperoxidase assays. Preferably, the presence or absence of anti-gluten antibodies, anti-tTG antibodies, and anti-endomysial antibodies is each independently determined using an immunoassay (e.g., ELISA) or immunohistochemical assay (e.g., IFA).

In some embodiments, the identification of subjects with CD or non-CD is based upon the presence or absence of markers of CD in conjunction with a statistical algorithm. A detailed description of useful statistical algorithms is provided above.

In some embodiments, the presence of EMA and anti-tTG antibodies is predictive of CD. In other embodiments, the presence of either EMA or anti-tTG antibodies in the absence of anti-gliadin IgA antibodies and anti-gliadin IgG antibodies is predictive of CD. In yet other embodiments, the presence of anti-gliadin IgA antibodies or anti-gliadin IgG antibodies in the absence of EMA and anti-tTG antibodies is predictive of non-CD. In some embodiments, the absence of EMA, anti-tTG antibodies, anti-gliadin IgA antibodies, and anti-gliadin IgG antibodies is predictive of non-CD.

If the subject's sample is determined to be non-CD, the sample is assayed in the IBD module to predict if it is an inflammatory bowel disease sample (IBD) or a non-IBD sample.

K. Methods of Predicting Inflammatory Bowel Disease (IBD)

In some embodiments, the method for determining whether a sample is an IBD sample or a non-IBD sample includes measuring the level of one or more IBD markers, such as, but not limited to, an anti-neutrophil cytoplasmic antibody (ANCA), an anti-*Saccharomyces cerevisiae* immunoglobulin G (ASCA-IgA), an anti-*Saccharomyces cerevisiae* immunoglobulin G (ASCA-IgG), an anti-outer membrane protein C (anti-OmpC) antibody, an anti-flagellin antibody, a perinuclear anti-neutrophil cytoplasmic antibody (pANCA), an anti-I2 antibody, an anti-Fla2 antibody, an anti-FlaX antibody, an anti-CBir antibody, ICAM-1, VCAM-1, VEGF, C-reactive protein (CRP), SAA, and combinations thereof. Additional IBD markers include lactoferrin, anti-lactoferrin antibodies, elastase, calprotectin, hemoglobin, NOD2/CARD 15, and combinations thereof. In other embodiments, the method also includes determining the genotype of each of the genetic markers ATG16L1, ECM1, NKX2-3, and STAT3. In some instances, genotyping each of the genetic markers includes detecting the presence or absence of a single nucleotide polymorphism (SNP) in each of the genetic markers, such as rs2241880 for ATG16L1, rs3737240 for ECM1, rs10883365 for NKX2-3, and/or rs744166 for STAT3.

In certain instances, the presence or level of at least one marker is determined using an immunoassay or an immunohistochemical assay. A non-limiting example of an immunoassay suitable for use in the method of the present invention includes an enzyme-linked immunosorbent assay (ELISA). Examples of immunohistochemical assays suitable for use in the method of the present invention include, but are not limited to, immunofluorescence assays such as direct fluorescent antibody assays, indirect fluorescent antibody (IFA) assays, anticomplement immunofluorescence assays, and avidin-biotin immunofluorescence assays. Other types of immunohistochemical assays include immunoperoxidase assays.

Detailed description of methods for predicting inflammatory bowel disease are found in, e.g., U.S. Pat. Nos. 7,873, 479; 8,315,818; and 8,715,943 and U.S. Patent Publication No. 2013/0225439, the disclosures of which are hereby incorporated by reference for all purposes.

IV. Examples

The following examples are offered to illustrate, but not to limit, the claimed invention.

Example 1. Diagnostic Method for Predicting Irritable Bowel Syndrome (IBS)

IBS is a heterogeneous disease with a vast mix of pathophysiology. To accurately diagnose IBS it is necessary to assay biomarker levels from the following seven classes: inflammatory bowel disease biomarkers (e.g., ANCA, ASCA, Cbir1, FlaX, etc.), mast cell markers (e.g., β-tryptase, PGE2 and histamine), microbiome markers (e.g., antibodies against, for example, Fla1, Fla2, FlaA, FliC, FliC2, FliC3, EcFliC, EcOFliC, SeFljB, CjFlaA, CjFlaB, SfFliC, CjCgtA, Cjdmh, CjGT-A, EcYidX, EcEra, EcFrvX, EcGabT, EcYedK, EcYabN, EcYhgN, RtMaga, RbCpaF, RgPilD, LaFrc, LaEno, LjEFtu, BfOmpA, PrOmpA, Cp10bA, CpSpA, EfSant, LmOsp, SfET-2, Cpatox, Cpbtox, etc.), markers of the kynurenine pathway (e.g., KA, 3-OHK, QA, and 3-OHAA), markers of the serotonin pathway (e.g., 5-HT, 3-HIAA, 5-HTP and 3-HK), markers of the bile acid malabsorption pathway (e.g., 7α-hydroxy-4-cholesten-3-one, and FGF19), and inflammatory markers (e.g., CRP, ICAM, VCAM, SAA, etc.).

This example illustrates a method for predicting IBS in an individual based on the biomarker scores of several diagnostic biomarker modules. See, FIG. 5. Each score is algorithmically derived from the presence or level (e.g., concentration) of at least one biomarker in a sample from the individual. The IBS diagnostic method uses measurements from at least 6 biomarker modules to compute an IBS score based on a statistical algorithm (e.g., decision tree method or random forest algorithm) for predicting IBD vs. non-IBD.

A first random model is used to determine if a patient's sample is a celiac disease (CD) or a non-celiac disease sample (105). If the score is higher (greater) than the CD vs. non-CD cut-off, the sample is predicted to be from a patient having CD, i.e., a CD sample (108). Otherwise, the sample is predicted to be from a patient having non-CD (110). The non-CD samples proceed to the next step of the algorithm, e.g., predicting IBD vs. non-IBD (120). The CD score utilized measurements of CD markers such as anti-gliadin IgA antibody, anti-gliadin IgG antibody, anti-tissue transglutaminase (tTG) antibody, and anti-endomysial antibody.

Another random model is used to determine if a patient's sample is an IBD or a non-IBD sample (120). The inflammatory bowel disease (IBD) score uses measurements of serology markers such as ANCA, ASCA-A, ASCA-G, FlaX, Fla2, pANCA, OmpC, CBir1, and combinations thereof. If the score is higher (greater) than the IBD vs. non-IBD cut-off, the sample is predicted to be from a patient having IBD, i.e., an IBD sample (123). Otherwise, the sample is predicted to be from a patient having non-IBD (125).

Samples predicted to have non-IBD, proceed to the next step of the algorithm, which is a decision tree or set of rules designed to rule in IBS (130). The IBS rules are based on one or more of 6 biomarker modules, including the kynurenine (140), mast cell (150), serotonin (160), bile acid malabsorption (170), microbiome (180) and inflammatory modules (190). The oxidative stress score (145) uses measurements from the kynurenine pathway, the tryptophan pathway and metabolites thereof, such as kynurenine (K), kynurenic acid (KA), 3-hydroxykynurenine (3-OHK or 3-HK), 3-hydroxyanthranilic acid (3-OHAA), quinolinic acid (QA), anthranilic acid (AA), 5-hydroxytryptophan (5-HTP) and 3-hydroxykynurenine (3-HK). The mast cell score (155) is based on the level of mast cell markers such as β-tryptase, prostaglandin E2, and histamine. The serotonin score (165) uses measurements from the serotonin pathway and metabolites thereof, including serotonin (5-HT), 5-hydroxyindole acetic acid (5-HIAA), serotonin-O-sulfate, and serotonin-O-phosphate. The bile acid malabsorption (BAM) score (175) is derived from the level (e.g., concentration) of BAM markers such as 7-α-hydroxycholestan-3-one and FGF19. The microbiome score (185) is determined from measurements of bacterial antigen antibodies including those against bacterial antigens, such as Fla1, Fla2, FlaA, FliC, FliC2, FliC3, YBaN1, ECFliC, EcOFliC, SeFljB, CjFlaA, CjFlaB, SfFliC, CjCgtA, Cjdmh, CjGT-A, EcYidX, EcEra, EcFrvX, EcGabT, EcYedK, EcYbaN, EcYhgN, RtMaga, RbCpaF, RgPilD, LaFrc, LaEno, LjEFtu, BfOmpa, PrOmpA, Cp10bA, CpSpA, EfSant, LmOsp, SfET-2, Cpatox, Cpbtox, EcSta2, EcOStx2A, CjcdtB/C, CdtcdA/B, and combinations thereof. The inflammatory score (195) uses measured levels of inflammatory markers such as acute phase proteins, e.g., CRP and SAA, and immunoglobulin proteins, e.g., ICAM-1, VCAM-1.

If the sample matches the pattern for the IBS rules, the algorithm predicts that the sample is IBS. Otherwise, the sample is predicted to be from a healthy patient. In other words, if the score is less than the IBS vs. healthy cut-off, the algorithm predicts the sample as having non-IBS. If the score is greater than the cut-off, the algorithm predicts the sample as having IBS. The IBS score can also be used to classify the sample as an IBS-constipation (IBS-C), IBS-diarrhea (IBS-D), IBS-mixed (IBS-M), IBS-alternating (IBS-A), or post-infectious IBS (IBS-PI) sample.

This method integrates expression data from different biomarker modules including the IBD score, oxidative stress (kynurenine) score, mast cell score, serotonin score, bile acid malabsorption (BAM) score, microbiome score, and inflammatory score to generate a predictive index (profile, score, and the like) that can be compared to a standardized diagnostic scale or look-up table.

Example 2. Calculating a Microbiome Score

This example illustrates a method for identifying predictive bacterial antigen antibody biomarkers (e.g., microbiome markers) that are indicative of IBS. This example also shows that these biomarkers can be used to determine if a sample is from a patient having IBS. Additionally, the example illustrates a method for calculating a microbiome score.

In this study, the level of antibodies against bacterial antigens was measured in samples from healthy controls and patients diagnosed as having IBS (e.g., IBS-D/M). The bacterial antigen antibodies included antibodies against bacterial antigen such as, EcFliC, EcOFlic, SeFljB, CjFlaA, CjFlaB, SfFliC, CjCgtA, Cjdmh, CjGT-A, EcYidX, EcEra, EcFrvX, EcGabT, EcYedK, EcYabN, EcYhgN, RtMaga, RbCpaF, RgPilD, LaFrc, LaEno, LjEFtu, BfOmpA, PrOmpA, Cp10bA, CpSpA, EfSant, LmOsp, SfET-2, Cpatox, and Cpbtox. There were approximately 200 healthy control samples and 200 IBS-D/M samples analyzed. The level of at least one inflammatory marker and at least one mast cell marker also measured. The presence or level (e.g., concentration) of the biomarkers were determined using methods such as amplification-based assays, such as PCR, hybridization assays, such as an ELISA, competitive ELISA, and CEER™ or immunohistochemical assay, or mobility assays such as separation chromatography, HPLC, or HMSA. Detailed descriptions of useful assays are found in, e.g., U.S. Pat. Nos. 8,278,057 and 8,114,616; U.S. Patent Publication Nos. 2012/0244558 and 2012/0315630.

A logistic regression model was used to identify markers that showed a statistically significant difference between healthy control and IBS patients. Table 2 shows the results.

TABLE 2

|  | Estimate | Std. Error | z value | Pr(>\|z\|) |  |
|---|---|---|---|---|---|
| Intercept | 1.6916 | 0.4957 | 3.4123 | 0.0006 | *** |
| CjFlaA | −1.1594 | 0.5771 | −2.0091 | 0.0445 | * |
| CjFlaB | 0.8389 | 0.4305 | 1.9484 | 0.0514 |  |
| CjGT.A | −0.7189 | 0.3188 | −2.2549 | 0.0241 | * |
| EcEra | 3.9686 | 0.7035 | 5.6417 | 0.0000 | *** |
| EcGabT | −4.4100 | 0.7601 | −5.8015 | 0.0000 | *** |
| EcOFliC | −1.5502 | 0.2244 | −6.9073 | 0.0000 | *** |
| EcYbaN | 2.8258 | 0.6672 | 4.2352 | 0.0000 | *** |
| SeFljB | −1.4180 | 0.5912 | −2.3987 | 0.0165 | * |
| SfFlic | 1.0425 | 0.2151 | 4.8472 | 0.0000 | *** |

Figure 6A:
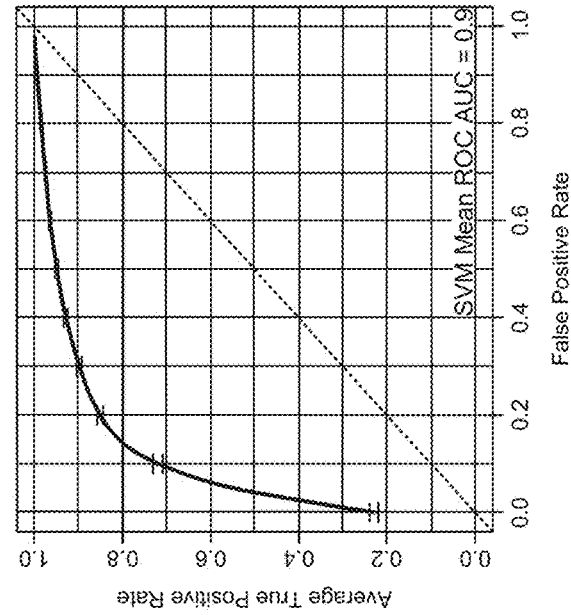
FIGS. 6A and 6B show exemplary embodiments of the statistical analysis of the biomarkers described herein.
Figure 6B:
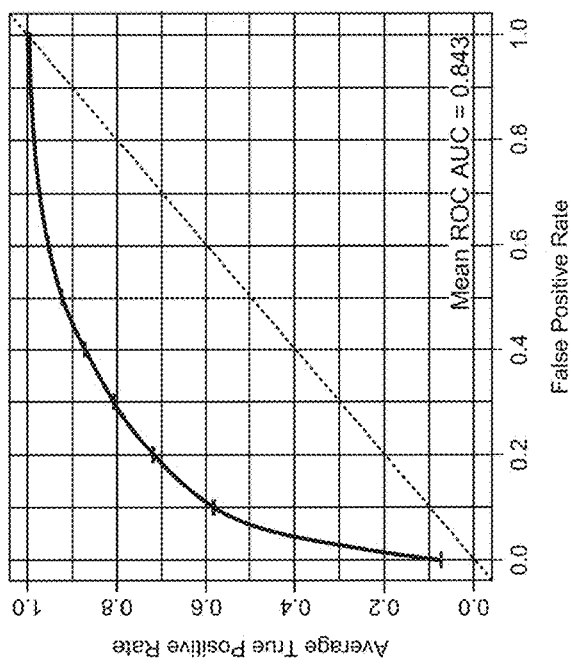

Of the 1000 iterations that were run, ⅔ were for the training set and ⅓ were for the validation set. FIG. 6A shows a ROC AUC of 0.843 when bacterial antigen markers and an inflammatory marker were analyzed. FIG. 6B shows a ROC AUC of 0.9 when bacterial antigen markers, an inflammatory marker and a mast cell marker were evaluated. The data shows that microbiome markers in combination with at least one inflammatory marker are predictive of IBS. Furthermore, the addition of at least one mast cell marker is also predictive of IBS over healthy control.

Figure 7:
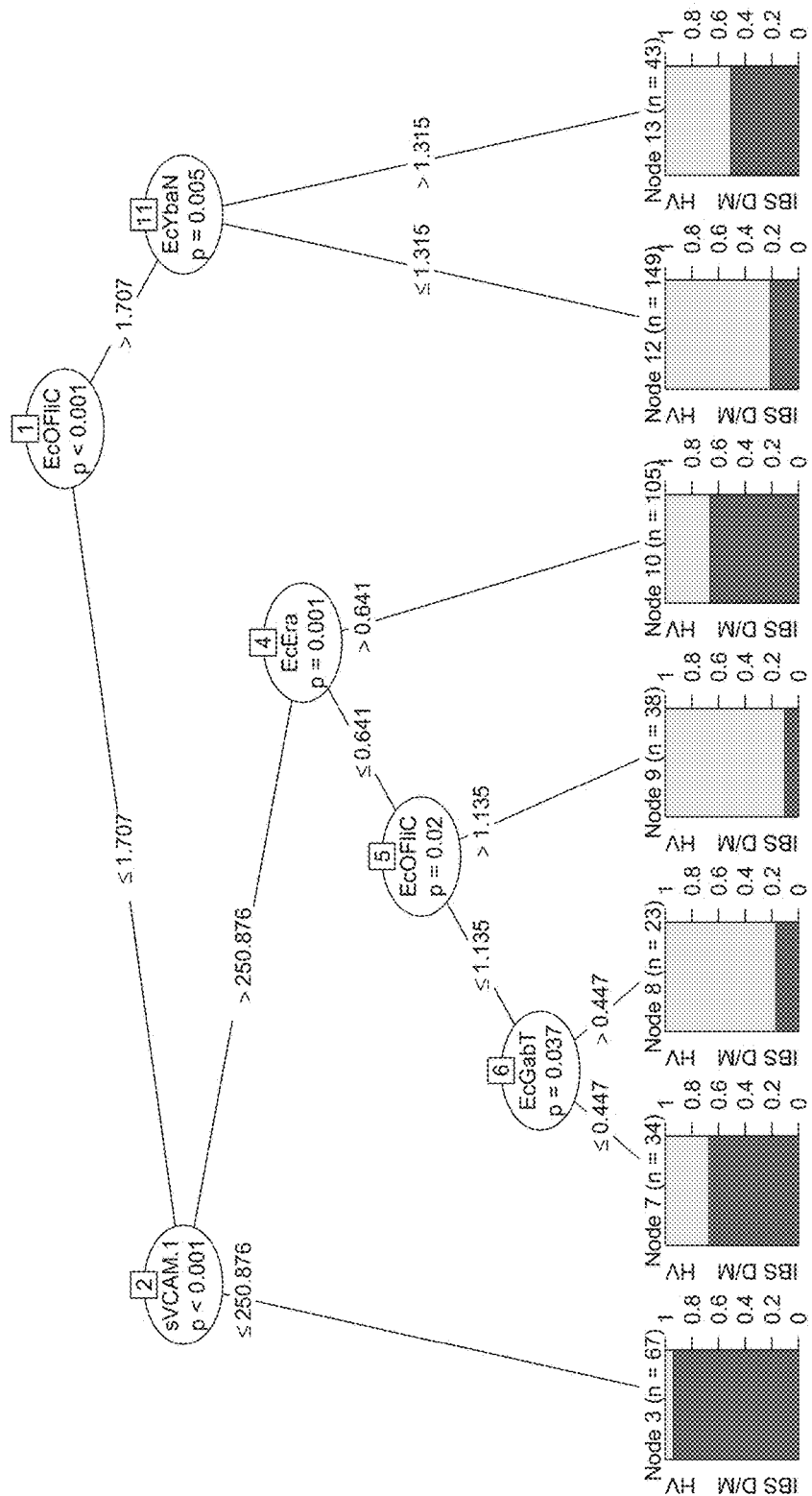
FIG. 7 shows the tree-building process with one inflammatory marker (sVCAM1), and several microbiome markers (EcGabT, EcOFliC, EcEra, and EcYbaN).

To understand the interactions between markers and biomarker classes in the model algorithm, decision trees were used. The steps of the tree-building process included 1) identifying a marker that best differentiates IBS patients from healthy controls, for instance, by lowest p-value; 2) identifying a marker cut-off value that best separates (distinguishes) IBS patients from healthy controls, and then moving on to the next node of the decision tree and repeating steps 1 and 2 (FIG. 7).

A microbiome score and percentile score were calculated for the patients diagnosed as having IBS and healthy controls. The levels of antibodies against the following bacterial antigens were measured: EcEra, EcFliC, EcFrvX, EcGabT, EcYedK, EcYbaN, EcOFliC, CjFlaA, CjFlaB, CjGTA, CjCgtA, Cjdmh, SeFljB and SfFliC (FIG. 8A-8N).

Figure 9A:
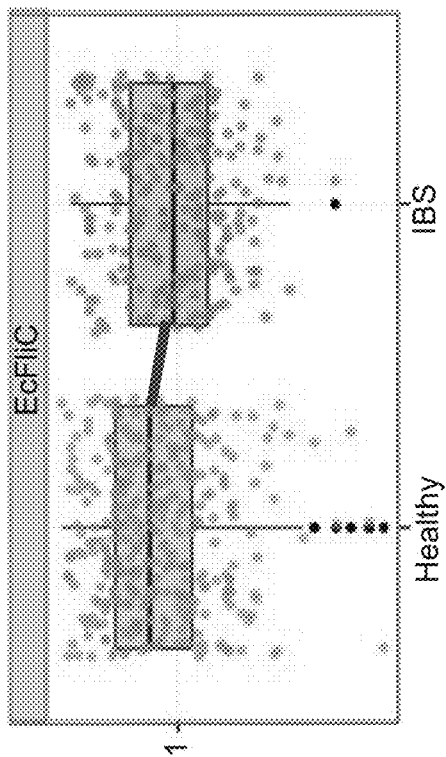
FIGS. 9A-9C show graphs used to calculated a biomarker score and a score percentile.
Figure 9B:
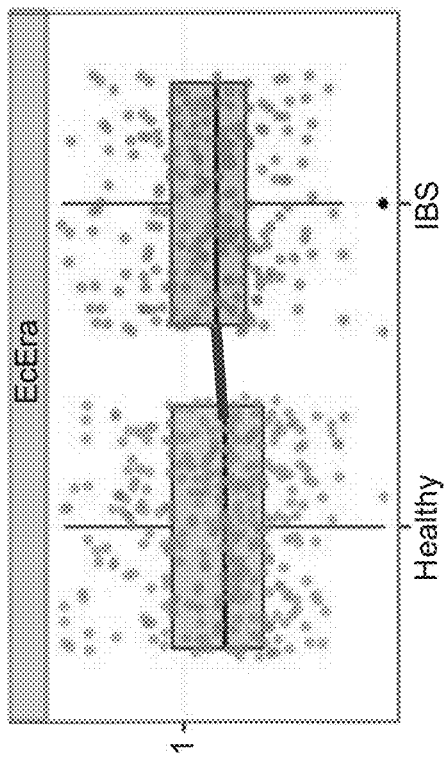
Figure 9C:
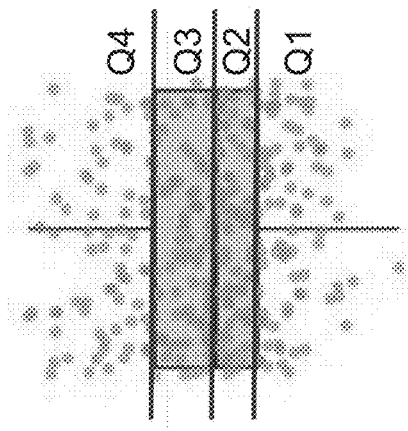

The individual's score was calculated by generating a weighted quartile sum score. Using a logistic regression model of disease status such as healthy versus IBS for all the markers, the coefficients from regression or slope were determined. A positive slope shows that the marker is predictive of IBS and a negative slope indicates that the marker is predictive of healthy status (FIGS. 9A and 9B, respectively). The coefficients were adjusted for the presence of other markers. Healthy controls were used to obtain quartile cut-offs (FIG. 9C). For each individual, the microbiome score=Σβ*quartile over all markers analyzed, wherein β represents the coefficients from the regression or slope between the disease cohorts (FIG. 9C).

Figure 10B:
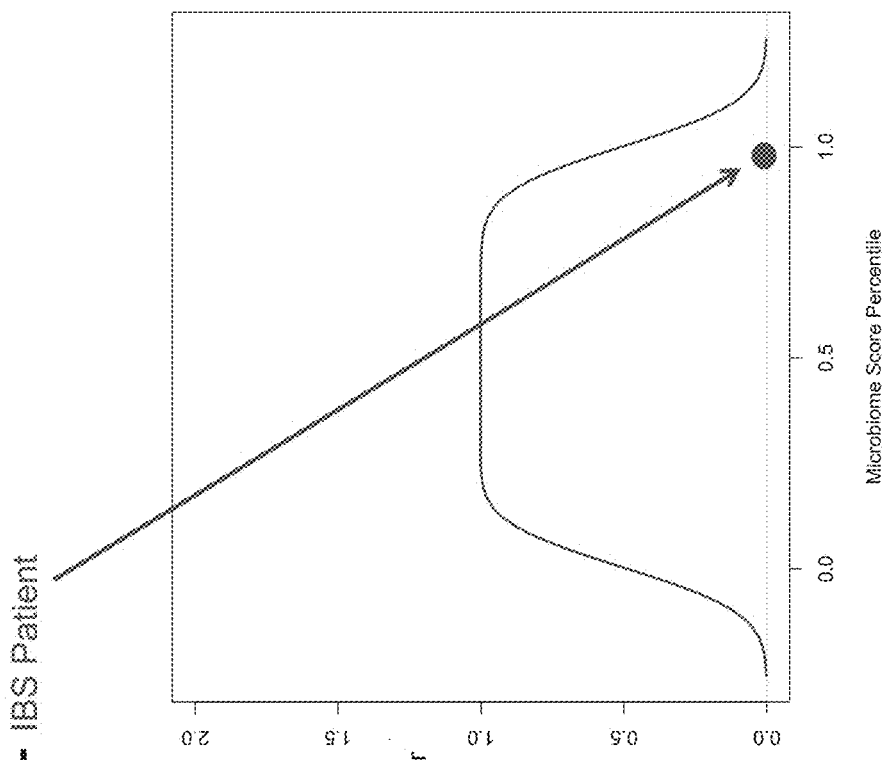
FIGS. 10A and 10B show graphs of the microbiome scores (FIG. 10A) and the microbiome score percentiles (FIG. 10B) for the subjects in the healthy control cohort. The graphs also show the microbiome score for one representative IBS patient relative to the healthy controls.
Figure 10A:
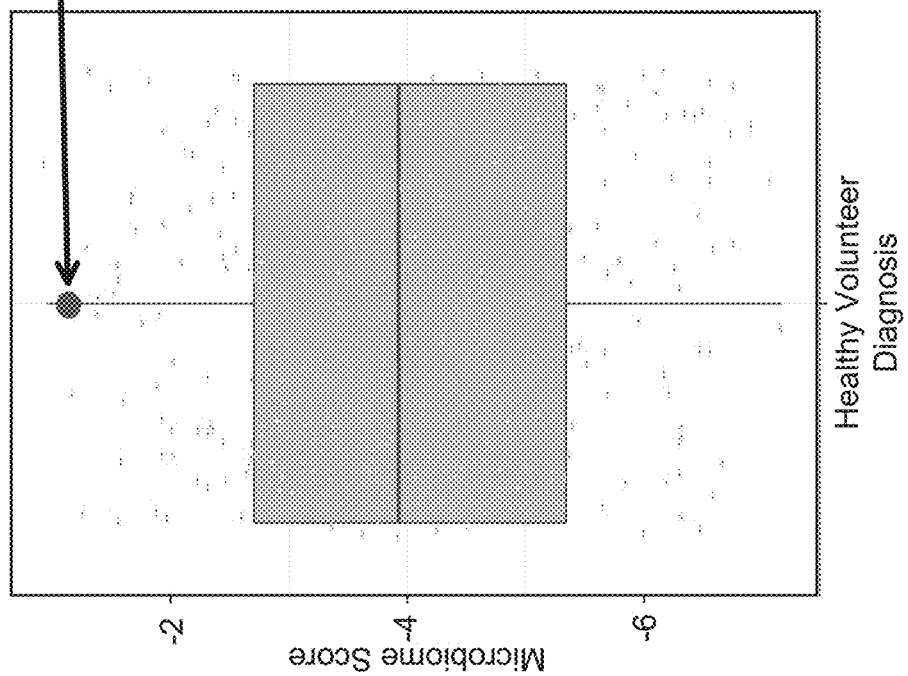

FIGS. 10A and B show graphs of the microbiome score (FIG. 10A) and microbiome score percentile (FIG. 10B) for the healthy control cohort. The graphs also show the microbiome score of one representative IBS patient relative to the control cohort.

Figure 11B:
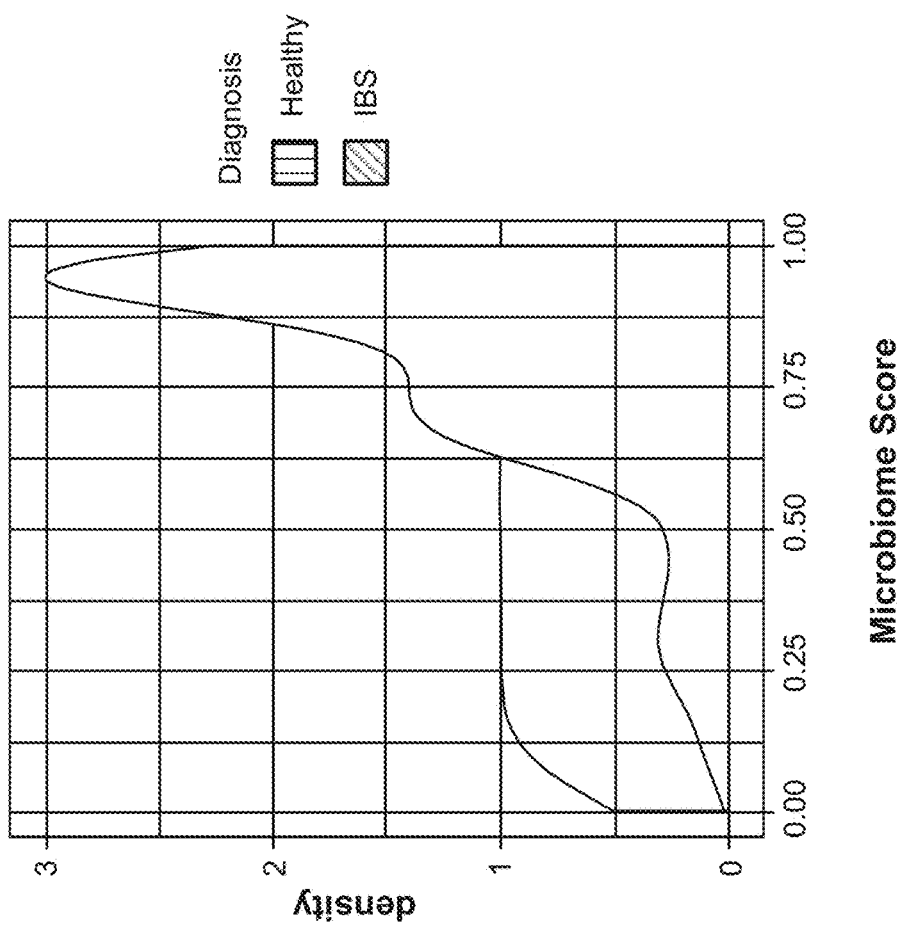
FIGS. 11A and 11B show graphs of the microbiome scores (FIG. 11A) in healthy controls and IBS-D/M patients and the distribution of the scores (FIG. 11B).
Figure 11A:
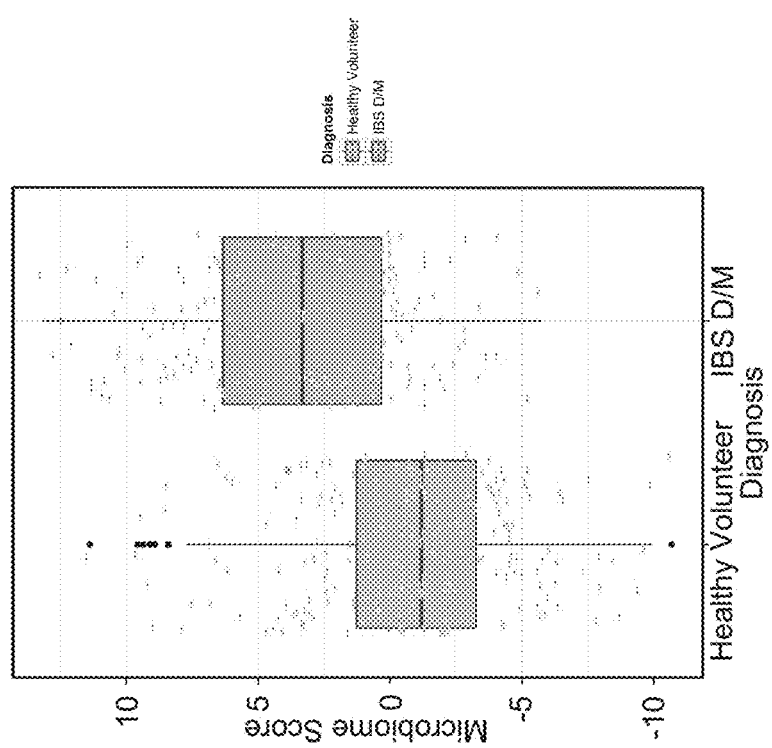

FIGS. 11A and B show graphs of the microbiome score (FIG. 11A) and microbiome score percentile (FIG. 11B) for the healthy control cohort and the IBS-DIM patient cohort. The results show that IBS-D/M patients have a higher microbiome score than healthy controls.

The method described herein for calculating a microbiome score and establishing quartiles can be used as an exemplary model for determining other module scores, e.g., an IBD score, oxidative stress score, mast cell score, serotonin score, BAM score, and inflammatory score.

Example 3. Predictive Microbiome Markers for IBS

This example shows that microbiome markers (e.g., antibodies against bacterial antigens) are predictive of IBS. The example provides a comparison of biomarker levels in healthy controls and patients with IBS-D/M.

Serum samples from healthy controls and patients with IBS-D/M were obtained and levels of antibodies against the bacterial antigens listed in Table 1 (see, above) were measured using an ELISA method.

Figure 12A:
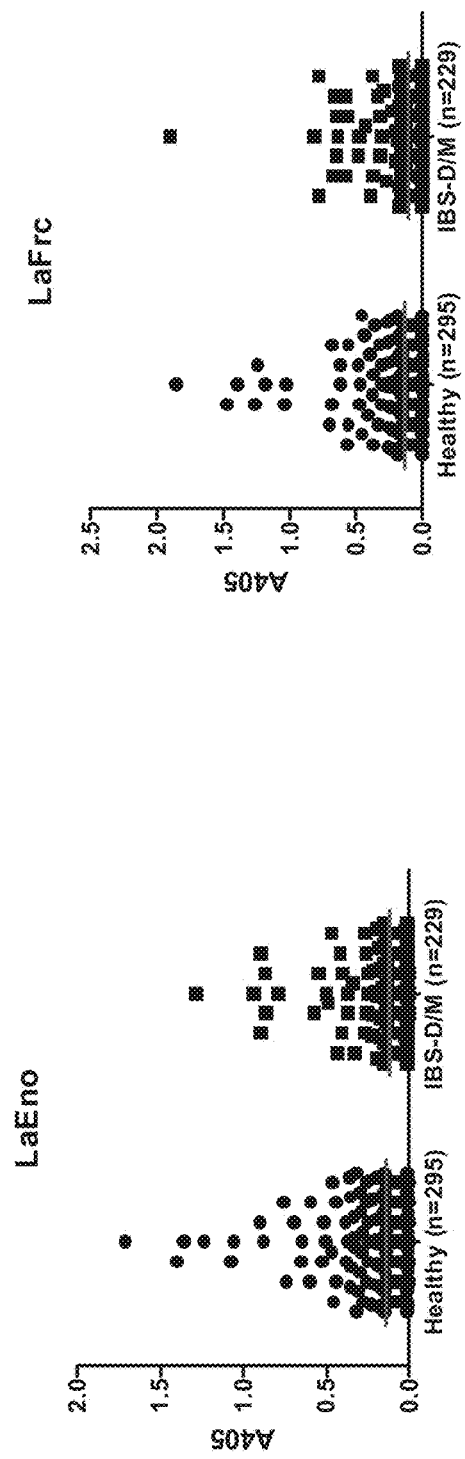
FIGS. 12A-12E show the level of different bacterial antigen antibody markers in cohort #1 containing healthy controls and IBS-D/M patients. The markers shown are LaEno (FIG. 12A), LaFrc (FIG. 12B), LjEFtu (FIG. 12C), BfOmpA (FIG. 12D), and PrOmpA (FIG. 12E).
Figure 12B:
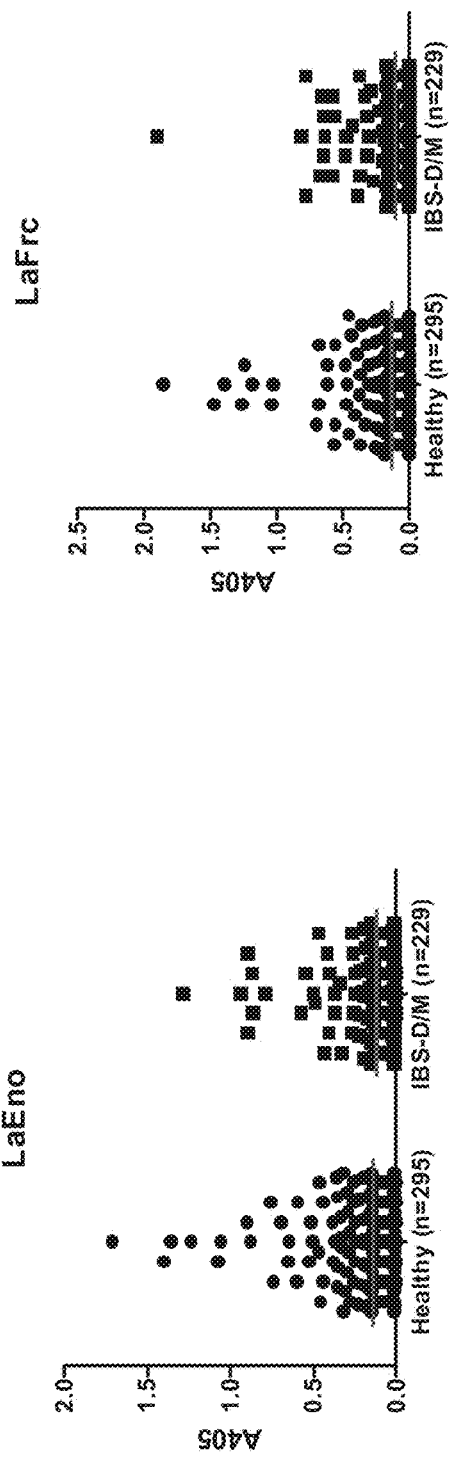
Figure 12C:
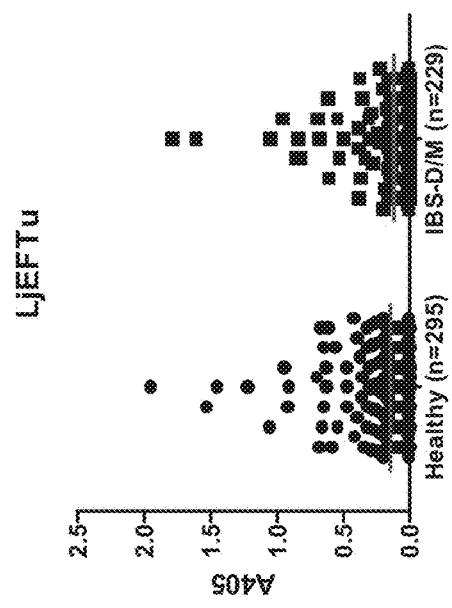
Figure 12E:
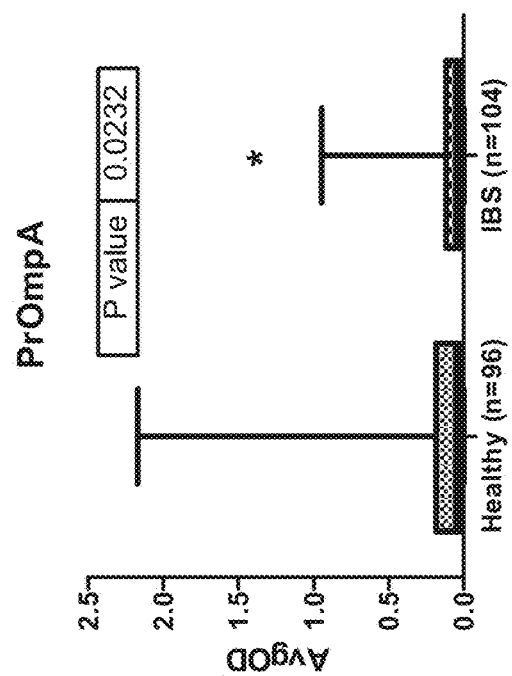
Figure 12D:
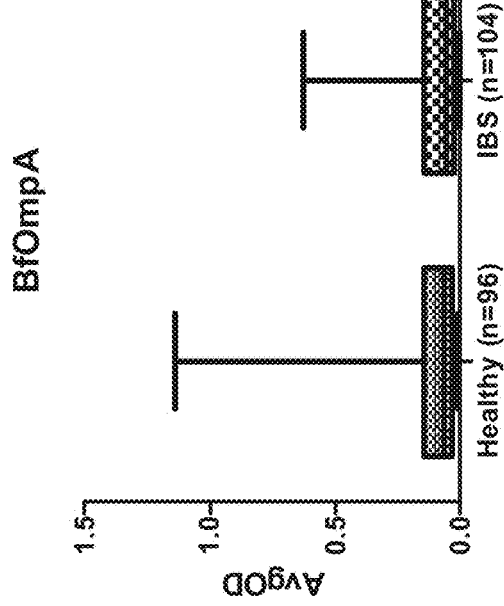
Figure 14B:
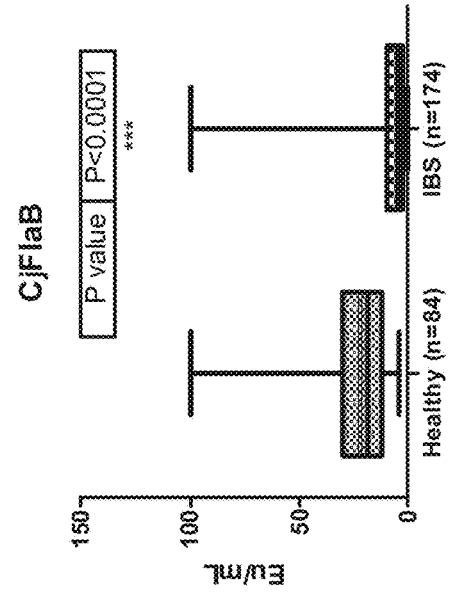
FIGS. 14A-14G show the level of different bacterial antigen antibody markers in cohort #3 which includes healthy controls and IBS patients. The markers shown are SfFliC (FIG. 14A), CjFlaB (FIG. 14B), CjFlaA (FIG. 14C), EcFliC (FIG. 14D), EcGabT (FIG. 14E), EcEra (FIG. 14F), and EcOFliC (FIG. 14G).
Figure 14D:
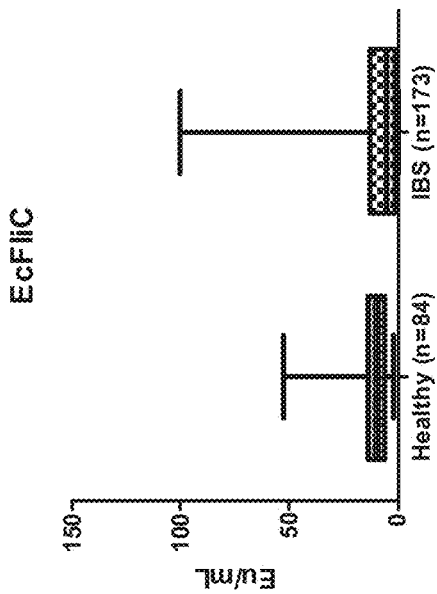
Figure 14A:
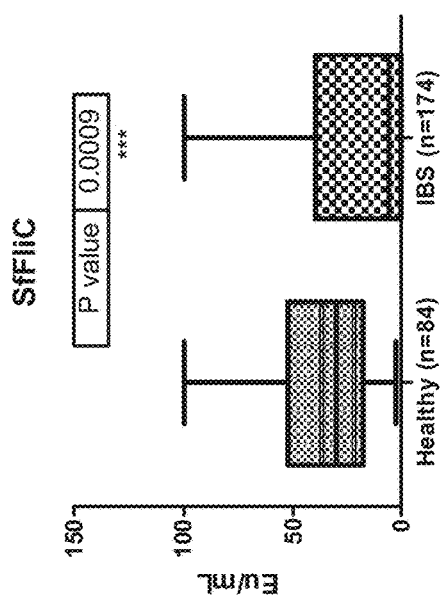
Figure 14C:
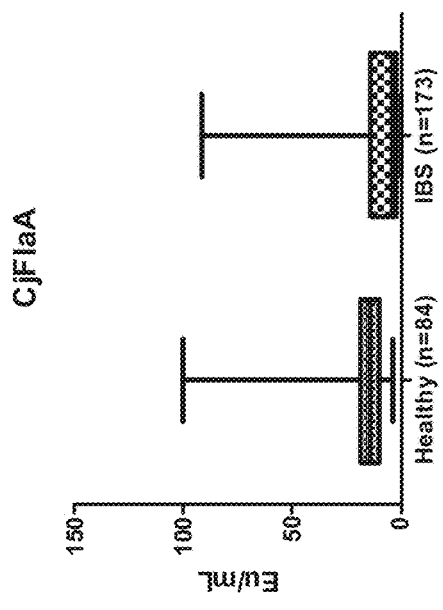
Figure 14F:
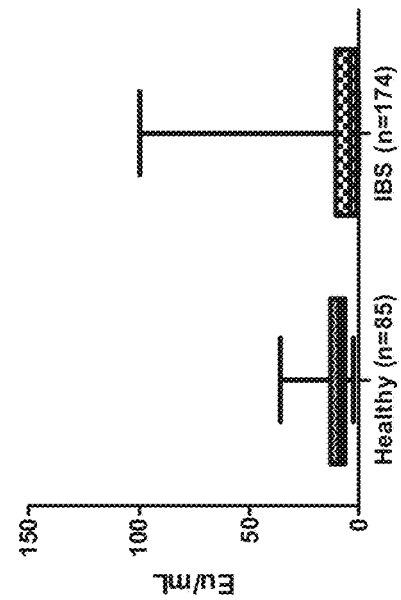
Figure 14E:
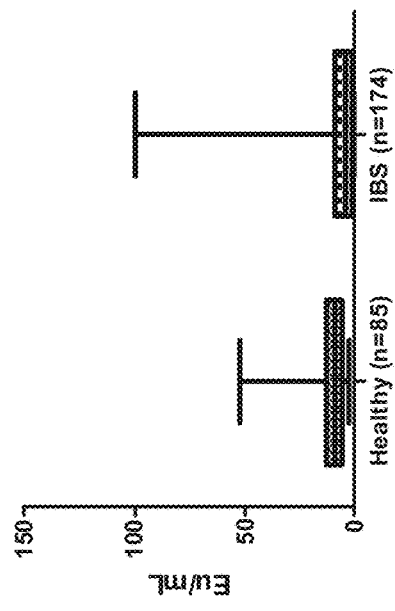
Figure 14G:
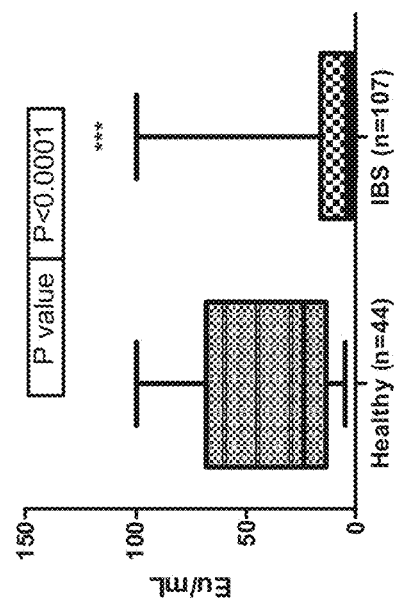

Microbiome markers were analyzed in 3 patient cohorts (#1-3). For cohort #1, there was no difference in the levels of anti-LaEno antibody (FIG. 12A), anti-LaFrc antibody (FIG. 12B), and anti-LjEFTu antibody (FIG. 12C) in the healthy controls (n=295) vs. the IBS-D/M patients (n=229). The level of anti-BfOmpA antibody (FIG. 12D) was also similar between the healthy controls (n=96) and the IBS patients (n=104). For anti-PrOmpA antibody, there was a difference between the two groups (p<0.0232; FIG. 12E). In particular, the IBS patients had a lower level of the PrOmpA marker. For cohort #2, the levels of anti-EcGabT antibody (FIG. 13A), anti-EcEra antibody (FIG. 13B), anti-SfFliC antibody (FIG. 13D) and anti-CjFlaB antibody (FIG. 13E) were higher in the IBS group. No difference was detected for the anti-EcOFliC (FIG. 13C), anti-CjFlaA (FIG. 13F), anti-EcFliC, (FIG. 13G), anti-RtMaga (FIG. 13H), anti-RgPilD (FIG. 13I), anti-RbCpaF (FIG. 13J) antibodies. There was a statistical difference in anti-RbCpaF antibody levels if the healthy control or IBS-C patients was compared to the IBS-D patients (FIG. 13K). With this marker, the IBS-D patients had higher levels. For cohort #3, both groups had similar levels of the anti-CjFlaA (FIG. 14C), anti-EcFliC (FIG. 14D), anti-EcGabT (FIG. 14E), and anti-EcEra (FIG. 14F) antibodies. The level of anti-SfFliC (FIG. 14A), anti-CjFlaB (FIG. 14B), and anti-EcOFliC (FIG. 14G) antibodies were lower in IBS patients compared to healthy controls.

This example shows that microbiome markers (e.g., antibodies against bacterial antigens) can be used to distinguish an IBS patient from a healthy control. Thus, these markers can be used in a method for diagnosing IBS.

Example 4. Detecting Serotonin Dysfunction in IBS Patients

This example shows that patients with IBS have higher levels of serotonin compared to healthy controls. Serotonin levels were measured using HPLC and a novel serotonin competitive ELISA which is described in detail in PCT application no. PCT/IB2014/061634, entitled "Pathway Specific Assays for Predicting Irritable Bowel Syndrome Diagnosis," filed May 22, 2014, the disclosure of which is hereby incorporated by reference in its entirety for all purposes.

Serum samples from healthy controls and patients with IBS-diarrhea (IBD-D) were obtained and derivatized to stabilize serotonin and metabolites thereof. Briefly, 50 µl of the sample was incubated with 50 µl of derivatization mix at 37° C. for 30 minutes. The derivatization mix contained 0.1 M CAPS buffer (pH11.0), 0.1 M p-(aminomethyl)benzyl compound, 0.05 M potassium hexacyanoferrate (III), and methanol at a ratio of 10:11:22:23 (v:v:v:v). After the derivatization reaction, the sample was deproteinated with acetonitrile (ACM) (e.g., 1:2 v/v serum:ACN). The deproteinated sample was then centrifuged at 14,000 rpm for 20 minutes. Afterwards, it was filtered through a 0.2 µm filter and then injected into the HPLC column which was a reverse phase, C18 column. For the method, the mobile phase included 15 mM sodium acetate, pH 4.5 with 1 mM octane sulfonic acid, sodium salt. The gradient was generated using acetonitrile as solvent B and the conditions were as follows: 20% solvent B at 0 min, 26% solvent B at 2 min, 28% solvent B at 12 min, 80% solvent B at 12.5 min, 80% solvent B at 14.5 min, 0% solvent B at 15 min, 0% solvent B at 16.5 min. 20% solvent B at 17.5 min, and 20% solvent B at 20 min. The fluorescence detection was with an excitation of 345 nm and an emission of 480 nm. Derivatized serotonin and its derivatized metabolites were detected and separated by HPLC. In particular, derivatized 5-HTP, 3-HK, 5-HT, 5-HIAA, and 5-HI were resolved into distinct, separate peaks (FIG. 15B).

Figure 15A:
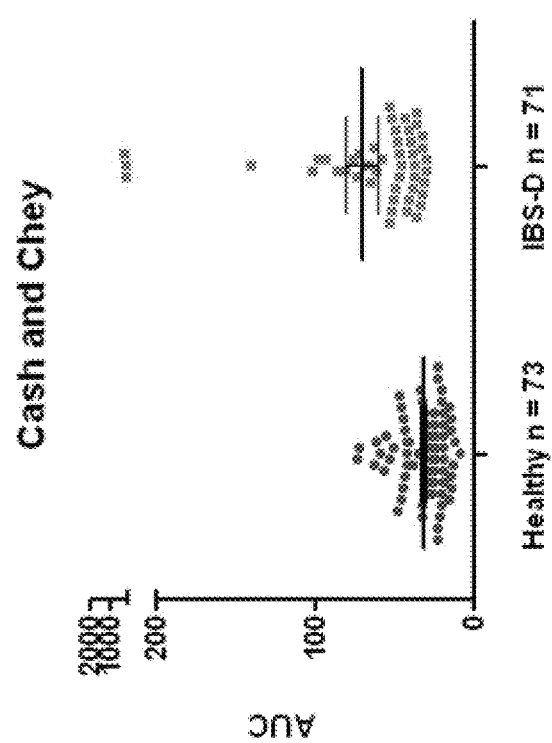
Figure 15B:
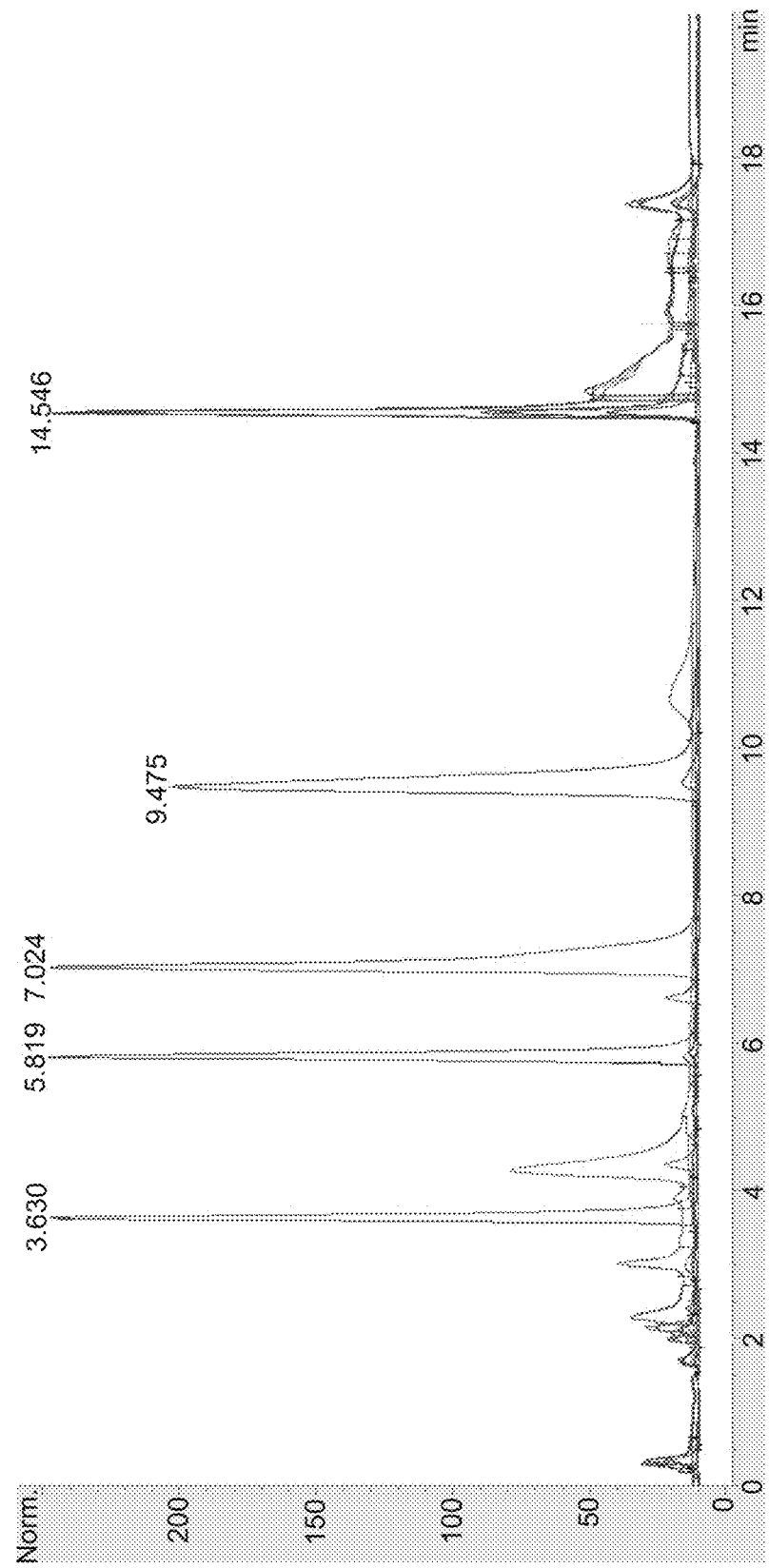

Serotonin levels were higher in patients with IBS-D compared to healthy controls (FIG. 15A). The mean level was 55±10 nM serotonin in IBS-D and 33±10 nM serotonin in healthy. Quartile analysis revealed that patients in quartile 3 (Q3) and quartile 4 (Q4) had significantly higher levels of serotonin (64.9 nM and 140.6 nM, respectively). Unlikely healthy controls, these IBS-D patients displayed serotonin dysfunction.

Figure 16B:
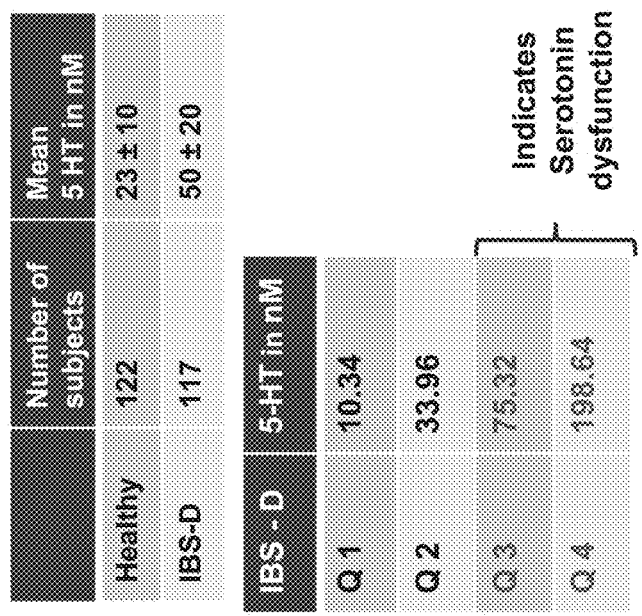
FIGS. 16A-16B show the level of serotonin in healthy controls and IBS-D patients as determined by a novel competitive ELISA.
Figure 16A:
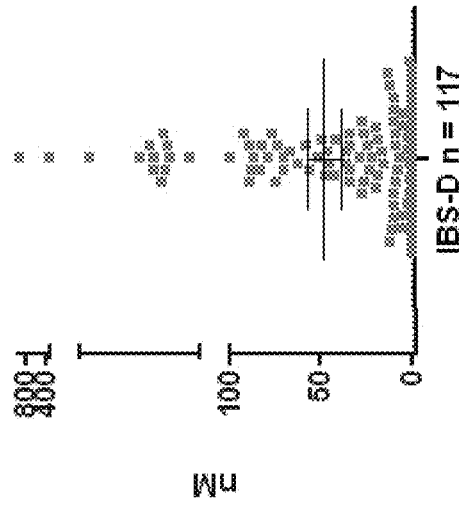

Serotonin levels were also measured using a competitive ELISA. A biotinylated, derivatized serotonin (e.g., Ser-D) analog was coated onto a streptavidin plate. The serum sample was derivatized as described above and incubated with a novel anti-Ser-D antibody generated in rabbits (see, PCT application no. PCT/IB2014/061634, entitled "Pathway Specific Assays for Predicting Irritable Bowel Syndrome Diagnosis," filed May 22, 2014. The sample mixture was added to the plate and incubated for 1 hour at RT. The plate was washed several times with wash buffer. A goat anti-rabbit antibody-HRP conjugate solution was added and incubated for 1 hour at RT. The plate was washed several times in wash buffer. A color substrate was added for the colorimetric reaction and stop solution was added prior to reading the plate at 405 nm. Serotonin levels from IBS-D patients are shown in FIG. 16A. The mean amount of serotonin in the IBS-D patients was 50±20 nM compared to 23±10 nM in healthy controls (FIG. 16B). Quartile analysis also showed that patients in quartiles 3 and 4 had significantly high levels compared to the healthy controls. The ELISA data supports the findings of the HPLC method. The experiments demonstrate that patients with IBD-D experience serotonin dysfunction. Thus, serotonin and metabolites thereof can serve as predictive indicators of IBS-D.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for determining irritable bowel syndrome (IBS) in a subject from a microbiome score and treating the subject in need thereof, the method comprising:
   (a) detecting in a sample from said subject a panel of markers comprising one or more antibodies against a bacterial antigen selected from the group consisting of EcOFlic, CjFlaB, SfFliC, EcEra, EcGabT, RbCpaF, PrOmpA and combinations thereof;
   (b) calculating a microbiome score based upon the presence or level of said panel of markers using a statistical algorithm to determine if the subject has IBS; and
   (c) administering to the subject having IBS a therapeutic drug to treat IBS.

2. The method of claim 1, wherein the panel of markers include antibodies against a bacterial antigen selected from the group consisting of EcEra, EcGabT, EcOFliC, CjFlaB, and combinations thereof.

3. The method of claim 1, wherein the therapeutic drug is directed to the serotonin pathway.

4. The method of claim 1, wherein the therapeutic drug changes the subject's gut microbiome community.

5. The method of claim 1, wherein the sample is a non-celiac disease sample.

6. The method of claim 1, wherein the sample is a non-Inflammatory Bowel Disease sample.

7. The method of claim 1, wherein the sample is selected from the group consisting of whole blood, plasma, serum, saliva, urine, stool, tears, any other bodily fluid, a tissue sample, and a cellular extract thereof.

8. The method of claim 7, wherein the sample is serum.

9. The method of claim 1, wherein the method comprises classifying the sample with a diagnosis of IBS.

10. The method of claim 9, wherein IBS is further classified as IBS-constipation (IBS-C), IBS diarrhea (IBS-D), IBS-mixed (IBS-M), IBS alternating (IBS-A), or post-infectious (IBS-PI).

11. The method of claim 1, wherein the method further comprises measuring an additional member selected from the group consisting of a mast cell score, an inflammatory score, a bile acid malabsorption score, an oxidative stress score, and a serotonin score.

12. The method of claim 11, wherein at least two members selected from the following group are measured: a mast cell score, an inflammatory score, a bile acid malabsorption score, an oxidative stress score, and a serotonin score.

13. The method of claim 11, wherein at least three members selected from the following group are measured: a mast cell score, an inflammatory score, a bile acid malabsorption score, an oxidative stress score, and a serotonin score.

14. The method of claim 11, wherein at least four members selected from the following group are measured: a mast cell score, an inflammatory score, a bile acid malabsorption score, an oxidative stress score, and a serotonin score.

15. The method of claim 11, wherein all members of the following group are measured: a mast cell score, an inflammatory score, a bile acid malabsorption score, an oxidative stress score, and a serotonin score.

* * * * *